(12) United States Patent
Roux et al.

(10) Patent No.: US 12,297,464 B2
(45) Date of Patent: *May 13, 2025

(54) MODIFIED PLANTS CONTAINING COMBINATION OF APYRASE GENES AND METHOD FOR MAKING MODIFIED PLANTS WITH COMBINATION OF APYRASE GENES

(71) Applicant: Board of Regents, The University of Texas System, Austin, TX (US)

(72) Inventors: Stanley J. Roux, Austin, TX (US); Gregory B. Clark, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 436 days.

This patent is subject to a terminal disclaimer.

(21) Appl. No.: 17/507,281

(22) Filed: Oct. 21, 2021

(65) Prior Publication Data

US 2022/0106577 A1 Apr. 7, 2022

Related U.S. Application Data

(63) Continuation of application No. 15/775,339, filed as application No. PCT/US2016/061640 on Nov. 11, 2016, now Pat. No. 11,203,745.

(60) Provisional application No. 62/360,210, filed on Jul. 8, 2016, provisional application No. 62/254,558, filed on Nov. 12, 2015, provisional application No. 62/254,552, filed on Nov. 12, 2015, provisional application No. 62/254,543, filed on Nov. 12, 2015.

(51) Int. Cl.
C12N 9/14 (2006.01)
C12N 9/16 (2006.01)
C12N 15/82 (2006.01)

(52) U.S. Cl.
CPC ............... *C12N 9/14* (2013.01); *C12N 9/16* (2013.01); *C12N 15/8261* (2013.01); *C12N 15/8273* (2013.01); *C12Y 306/01005* (2013.01)

(58) Field of Classification Search
None
See application file for complete search history.

(56) References Cited

U.S. PATENT DOCUMENTS

| | | | |
|---|---|---|---|
| 6,350,447 B1 | 2/2002 | Chadwick et al. | |
| 6,448,472 B1 | 9/2002 | Thomas et al. | |
| 11,203,745 B2 | 12/2021 | Roux et al. | |
| 2002/0019995 A1 | 2/2002 | Etzler et al. | |
| 2002/0077365 A1 | 6/2002 | Windsor et al. | |
| 2002/0103082 A1 | 8/2002 | Windsor et al. | |
| 2002/0160915 A1* | 10/2002 | Windsor .............. | A01N 37/30 504/116.1 |
| 2002/0173031 A1 | 11/2002 | Thomas et al. | |
| 2003/0008369 A1 | 1/2003 | Windsor et al. | |
| 2003/0233670 A1 | 12/2003 | Edgerton et al. | |
| 2006/0265779 A1 | 11/2006 | Thomas et al. | |
| 2011/0283419 A1 | 11/2011 | Roux et al. | |
| 2013/0232642 A1 | 9/2013 | Allen et al. | |
| 2014/0123342 A1 | 5/2014 | Roux et al. | |

FOREIGN PATENT DOCUMENTS

| JP | 2001017176 A | 1/2001 |
|---|---|---|
| WO | WO 2007/019616 | 2/2007 |

OTHER PUBLICATIONS

Timmermans et al. "Geminiviruses and their uses as extrachromosomal replicons." Annual review of plant biology 45.1 (1994): 79-112. (Year: 1994).*
Steinebrunner et al., Molecular and biochemical comparison of two different apyrases from *Arabidopsis thaliana*, Plant Physiology and Biochemistry, 38(12), 913-922, 2000.
International Search Report and Written Opinion regarding International Application No. PCT/US2016/061640, dated Jun. 26, 2017.
Cho et al., "Functional Mechanism of Calmodulin for Cellular Responses in Plants," Journal of Life Science 19 (1):129-137, 2009.
Govindarajulu et al., "GS52 Ecto-Apyrase Plays a Critical Role during Soybean Nodulation," Plant Physiology 149:994-1004, 2009.
Hsieh et al, "Regulation of a recombinant pea nuclear apyrase by calmodulin and casein kinase II," Biochimica et Biophysica Acta 1494:248-255, 2000.
Thomas et al., "Apyrase Functions in Plant Phosphate Nutrition and Mobilizes Phosphate from Extracellular ATP," Plant Physiology 119:543-551, 1999.
Windsor et al., "Multiherbicide tolerance conferred by AtPgp1 and apyrase overexpression in *Arabidopsis thaliana*," Nature Biology 21:428-433, 2003.
Wu et al., "Apyrases (NTPDases) Play Key Role in Growth Control in *Arabidopsis*," Plant Physiology 114:961-975, 2007.
Wu, "Transformation of *Solanum lycopersicum* (tomatoes) with a growth regulating protein apyrase," Ph.D. Dissertation, University of Texas at Austin, 2010.
O'Neil et al., "How calmodulin binds its targets: sequence independent recognition of amphiphilic α-helices," Trends Biochem. Sci. 15:59-64, 1990.

(Continued)

*Primary Examiner* — Charles Logsdon
(74) *Attorney, Agent, or Firm* — Dentons US LLP

(57) ABSTRACT

The present disclosure is directed to a modified plant cell, plant tissue, plantlet, plant part, plant, and progeny thereof containing a combination of apyrase genes, including at least one modified gene and/or at least one additional apyrase gene. The disclosure is also directed to a method of making a modified plant with a modified apyrase gene and/or an additional apyrase gene. The modified plant generally exhibits at least one improved characteristic over the plant line from which it was derived. The disclosure also relates to a recombinant DNA molecule comprising a nucleotide sequence encoding an apyrase enzyme as disclosed.

5 Claims, 48 Drawing Sheets

Specification includes a Sequence Listing.

(56) References Cited

OTHER PUBLICATIONS

Snedden et al., "Calmodulin, calmodulin-related proteins and plant responses to the environment," Trends in Plant Science, 3(8):299-304, 1998.
Extended European Search Report regarding Europe Application No. 16865138, dated Mar. 25, 2019.
Virdi et al., "Abiotic stress responses in plants: roles of calmodulin-regulated proteins," Frontiers in Plant Science vol. 6, Oct. 14, 2015.
EBI Accession No. UNIPROT:P52914, Sep. 16, 2015.
Massalski, et al. (PloS one 10.3 (2015): e0115832). (Year: 2015).
UniProt Accession P52914, entered Jan. 10, 1996. (Year: 1996).

* cited by examiner

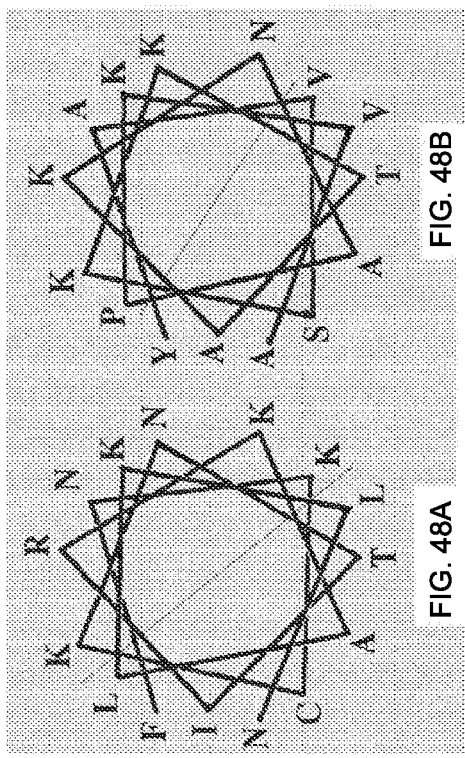
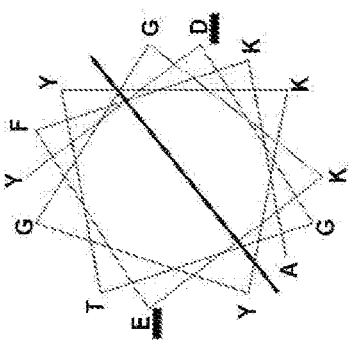
FIG. 48A
FIG. 48B
298 YDGTYKYGGKEFKA 311
FIG. 48C
FIG. 48

MODIFIED PLANTS CONTAINING COMBINATION OF APYRASE GENES AND METHOD FOR MAKING MODIFIED PLANTS WITH COMBINATION OF APYRASE GENES

CROSS-REFERENCE TO RELATED APPLICATIONS

This application is a continuation of U.S. patent application Ser. No. 15/775,339, filed May 10, 2018, which is a 371 National Stage Application of International Application No. PCT/US2016/061640, filed Nov. 11, 2016, which claims the benefit of U.S. Provisional Application No. 62/254,558, filed Nov. 12, 2015, U.S. Provisional Application No. 62/254,552, filed Nov. 12, 2015, U.S. Provisional Application No. 62/254,543, filed Nov. 12, 2015, and U.S. Provisional Application No. 62/360,210, filed Jul. 8, 2016, each of the disclosures of which are herein incorporated by reference in their entireties.

STATEMENT OF FEDERALLY FUNDED RESEARCH

Not applicable.

INCORPORATION-BY-REFERENCE OF SEQUENCE LISTING

The present application includes a Sequence Listing which has been submitted in ASCII format via EFS-Web and is hereby incorporated by reference in its entirety. Said Sequence Listing, created on Nov. 11, 2016, is named UTTA005WO_ST25.txt and is 11.9 kilobytes in size.

TECHNICAL FIELD OF THE INVENTION

The present disclosure relates in general to the fields of apyrase genes, genetically modified plants, and expression of apyrase genes in plants in a manner not found in nature. The disclosure further relates to methods for designing and making modified apyrase genes and plants that express apyrase genes in a manner not found in nature.

BACKGROUND ART

Apyrases (nucleoside triphosphate diphosphohydrolases) are enzymes that can remove the terminal phosphate from NTPs and NDPs, but not from nucleotide monophosphates. They play diverse roles in the physiology of both animals (Knowles, 2011) and plants (Clark et al., 2014). Early studies indicating that certain apyrases could regulate certain aspects of plant growth were published by Thomas et al. (1999) and by Wu et al. (2007). These studies narrowly showed in a particular model that constitutive expression of certain apyrases could promote vegetative growth, and suppression of these apyrases could inhibit growth. However, these studies only examined vegetative growth of roots and shoots in young seedlings grown on agar plates, and they did not test whether these effects would have any impact on later stages of plant growth and seed productivity. Often factors that promote vegetative growth have little or no effect on reproductive growth, or, in some cases, can even inhibit reproductive growth (Barker, 2010). Moreover, the early studies were restricted to the effects of apyrase expression on the growth of only one small weedy plant, *Arabidopsis thaliana*. Thus, these early studies could not predict whether constitutive expression of apyrase would have any impact on the seed productivity of important crop plants such as soybean.

The same seedling studies that reported the apyrase-enhanced vegetative growth of *Arabidopsis* seedlings also reported that the constitutive expression of a certain apyrase could enhance the uptake of phosphate by those seedlings (Thomas et al., 1999). However, this enhancement was observed only at a very high phosphate concentration (2 mM), which is significantly higher than what is found in solution in most soils or in commercial fertilizers (Smith et al., 2015). Thus it seemed, based on this early laboratory result, that the constitutive expression of apyrase would have little or no effect on phosphate uptake under field conditions before or after fertilizer use, and thus would have little practical value.

SUMMARY OF THE INVENTION

In one embodiment, the present disclosure is directed to a modified apyrase gene. The disclosure is further directed to a method of designing and making a modified apyrase gene. In certain embodiments, the modified apyrase gene is a modified psNTP9, a modified apyrase gene encoding the amino acid sequence of SEQ ID NO:2, or a modified apyrase gene comprising the DNA sequence of SEQ ID NO:4. In a further embodiment, the present disclosure provides a method of modifying an apyrase enzyme to improve calmodulin binding, comprising plotting an amino acid sequence of the apyrase enzyme on a helical wheel plot, determining a portion of the helical wheel plot comprising predominately hydrophobic amino acid residues and a portion of the helical wheel plot comprising predominately basic amino acid residues, and replacing at least a first non-hydrophobic amino acid residue in the portion of the helical wheel plot comprising predominately hydrophobic amino acid residues with a more hydrophobic amino acid residue or at least a first non-basic amino acid residue in the portion of the helical wheel plot comprising predominately basic amino acid residues with a more basic amino acid residue.

In another embodiment, the disclosure is directed to a plant cell, plant tissue, a plantlet, a plant part, a plant, and their progeny containing a modified apyrase gene and methods of making such a plant cell, plant tissue, plantlet, plant part, plant, and their progeny containing a modified apyrase gene. In further embodiments the plant part is a cell, a seed, a root, a stem, a leaf, a head, a flower, or pollen. In yet another embodiment, the modified apyrase gene is a modified psNTP9, a modified apyrase gene encoding the amino acid sequence of SEQ ID NO:2, or a modified apyrase gene comprising the DNA sequence SEQ ID NO:4.

The disclosure is further directed to a plant part, a plant and their progeny modified to contain and express at least one additional apyrase gene, e.g., by extrachromosomal expression or insertion in its genome, compared to the plant line from which it was derived, and methods of making such a plant part, plant, and their progeny containing at least one additional apyrase gene, and methods of making such plants, plant parts and progeny plants. In certain embodiments, the additional apyrase gene is a naturally-occurring apyrase gene. In other embodiments, the additional apyrase gene is an exogenous apyrase gene or a modified apyrase gene. In particular embodiments the additional apyrase gene is a pea apyrase gene or an *Arabidopsis* apyrase gene, or a pea apyrase gene comprising the DNA sequence of SEQ ID NO:3 or a pea apyrase gene encoding the amino acid sequence of SEQ ID NO:1. In various embodiments, the modified plant has increased yield over the plant line from which it was derived.

The disclosure is further directed to a plant cell, plant tissue, a plantlet, a plant part, a plant, and their progeny containing a combination of at least one modified apyrase gene and at least one additional apyrase gene compared to the plant line from which it was derived, and methods of making such a plant cell, plant tissue, plantlet, plant part, plant, and their progeny containing at least one modified gene and at least one additional apyrase gene. In some embodiments, the modified apyrase gene is a modified psNTP9, a modified apyrase gene encoding the amino acid sequence of SEQ ID NO:2, or a modified apyrase gene comprising the DNA sequence of SEQ ID NO:4. In other embodiments, the additional apyrase gene is a naturally-occurring apyrase gene. In another embodiment, the additional apyrase gene is an exogenous apyrase gene, for example a pea apyrase gene or an *Arabidopsis* apyrase gene, a pea apyrase gene comprising the DNA sequence of SEQ ID NO:3 or a pea apyrase gene encoding the amino acid sequence of SEQ ID NO:1.

The modified plant according to each embodiment of the disclosure generally exhibits one or more improvements over the plant line from which it was derived, selected from at least one of: increased yield, phosphate uptake, drought resistance, disease resistance, fungal resistance, nutrient uptake, water uptake, average primary root length, average number of lateral roots, average root hair density and length, average number and size of root nodules in legumes, average number of seed pods, average seed pod size, average seed size, average seed weight, seed germination, seed survival, average number of siliques, average silique size, average leaf length, average leaf area, or average plant height. The modified plant according to various embodiments of the disclosure exhibits better performance in one or more of those characteristics over the plant line from which it was derived when placed under stress, including drought or osmotic stress.

The additional apyrase gene can be any known apyrase gene. The modified apyrase gene can be derived from any known apyrase gene. There are many known and published apyrase genes. (See e.g., Clark et al, 2014, relevant portions incorporated herein by reference). Different apyrase genes can be found in different plants, and even within the same plant species there can be multiple known apyrase genes. Many of the apyrase genes share a very similar DNA sequence. The source apyrase gene can be modified such that the amino acid sequence encoded by the modified gene is the same or different than the amino acid sequence encoded by the source apyrase gene. In certain embodiments, the modified apyrase gene encodes the same amino acid sequence as the source apyrase gene. In another embodiment, the modified apyrase gene encodes a different amino acid sequence than the source apyrase gene. In a further embodiment, the modified apyrase gene encodes an amino acid sequence that contains 1, 2, 3 or more amino acid changes relative to the amino acid sequence encoded by the source apyrase gene. A plant modified to contain the modified apyrase gene generally exhibits one or more improved characteristics over the plant line from which it was derived. In some embodiments, the apyrase gene is a pea apyrase gene or an *Arabidopsis* apyrase gene.

The additional apyrase gene or modified apyrase gene can be added to the genome of a plant by transformation, such as by *Agrobacterium*-mediated transformation. Alternatively, an additional apyrase gene or modified apyrase gene can be incorporated into a plant by conventional breeding techniques, e.g., crossing a plant line with another plant line that contains the additional apyrase gene and/or modified apyrase gene. In a further embodiment, a plant line containing a modified apyrase gene can be crossed with a plant line containing an additional apyrase gene, resulting in a plant containing a combination of a modified apyrase gene and an additional apyrase gene. In another embodiment, a modified apyrase gene and/or an additional apyrase gene are transferred into the genome of a plant by a genetic engineering technique, e.g., via *Agrobacterium* transformation. Alternatively, the apyrase or modified apyrase gene can be an exogenous apyrase or modified gene. In another alternative, the apyrase or modified apyrase gene can be expressed extrachromosomally.

The present disclosure also provides a modified apyrase enzyme comprising the amino acid sequence of SEQ ID NO:2 and a modified apyrase gene comprising the nucleotide sequence of SEQ ID NO:4. Another aspect of the disclosure is a recombinant, double-stranded DNA molecule comprising in sequence: a promoter capable of causing expression of a structural DNA sequence in a plant; a structural DNA sequence of an apyrase gene that encodes an apyrase, for example, a modified apyrase having an amino acid sequence comprising the sequence of SEQ ID NO:2; and a 3' non-translated region which functions in plant cells to cause the addition of a stretch of polyadenyl nucleotides to the 3' end of the RNA sequence. Such a DNA molecule is generally capable of expressing the apyrase comprising an amino acid sequence such as SEQ ID NO:2 in a plant cell. The promoter may be a heterologous promoter. As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism. In some embodiments, the protein has at least about 85% sequence identity, at least about 90% sequence identity, at least 95% sequence identity, at least 96% sequence identity, at least 97% sequence identity, at least 98% sequence identity, or at least 99% sequence identity over its full coding length to a polypeptide sequence of SEQ ID NO:1 or SEQ ID NO:2. In certain embodiments, the promoter is a cauliflower mosaic virus (CaMV) promoter. Thus, the disclosure provides a recombinant DNA molecule comprising a heterologous promoter functional in a plant cell, operably linked to a nucleic acid sequence encoding a polypeptide that has at least 90% sequence identity, at least 95% sequence identity, at least 96% sequence identity, at least 97% sequence identity, at least 98% sequence identity, or at least 99% sequence identity over its full coding length to a polypeptide sequence of SEQ ID NO:1 or SEQ ID NO:2. In certain embodiments the DNA molecule comprises the nucleic acid sequence of SEQ ID NO:3 or SEQ ID NO:4.

The disclosure is further directed to a modified apyrase gene encoding an amino acid sequence of SEQ ID NO:2, a plant cell comprising the amino sequence of SEQ ID NO:2, a plant tissue comprising the amino sequence of SEQ ID NO:2, a plantlet comprising the amino sequence of SEQ ID NO:2, a plant part comprising the amino sequence of SEQ ID NO:2, a plant comprising the amino sequence of SEQ ID NO:2, and their progeny that contain and express the amino sequence of SEQ ID NO:2. The disclosure is also directed to an isolated DNA molecule that encodes an apyrase comprising the sequence of SEQ ID NO:2. In an alternative aspect, SEQ ID NO:2 can be expressed extrachromosomally.

The disclosure is further directed to the DNA sequence of SEQ ID NO:4 or a modified apyrase gene substantially comprising the sequence of SEQ ID NO:4. The disclosure is further directed to a plant cell, plant tissue, a plantlet, a plant part, a plant, and their progeny containing a DNA sequence comprising SEQ ID NO:4. In an alternative aspect, SEQ ID NO:4 can be expressed extrachromosomally.

In certain embodiments, the plant cell, plant tissue, plantlet, plant part, plant and their progeny according to the disclosure exhibit one or more improvements over the plant line from which they were derived of increased yield, phosphate uptake, drought resistance, disease resistance, fungal resistance, nutrient uptake, water uptake, average primary root length, average number of lateral roots, average number of seed pods, average seed pod size, average seed size, average seed weight, seed germination, seed survival, average number of siliques, average silique size, average leaf length, average leaf area, and average plant height. The modified plant according to the disclosure generally exhibits better performance in any of those characteristics over the plant line from which it was derived when placed under stress, including drought or osmotic stress.

The modified plant according to any of the embodiments of the disclosure can be a monocot plant or a dicot plant. In particular embodiments, the modified plant is a soybean, cotton (*Gossypium* sp. including for instance *G. hirsutum*), canola, potato, rice, wheat, sugar beet, or corn (maize) plant.

The disclosure is also directed to a method of designing a modification to an apyrase gene comprising plotting a translated sequence of an apyrase gene on a helical wheel plot, identifying a region that appears to be a calmodulin binding region, selecting at least one nucleotide for modification that would result in an amino acid modification to enhance the binding characteristics of the calmodulin binding region, preparing the modified gene, inserting the modified gene into plant tissue, wherein the resulting plant exhibits at least one improvement over the plant line from which it was derived. The disclosure is also directed to a modified apyrase amino acid sequence and a modified apyrase nucleotide sequence designed or modified by that technique.

BRIEF DESCRIPTION OF THE DRAWINGS

For a more complete understanding of the features and advantages of the present disclosure, reference is now made to the detailed description along with the accompanying figures.

FIG. 48A, FIG. 48B and FIG. 48C are helical wheel arrangements of sequences from pea apyrase (FIG. 48A and FIG. 48B) and *Arabidopsis* apyrase (FIG. 48C).

DETAILED DESCRIPTION OF THE INVENTION

Figure 1:
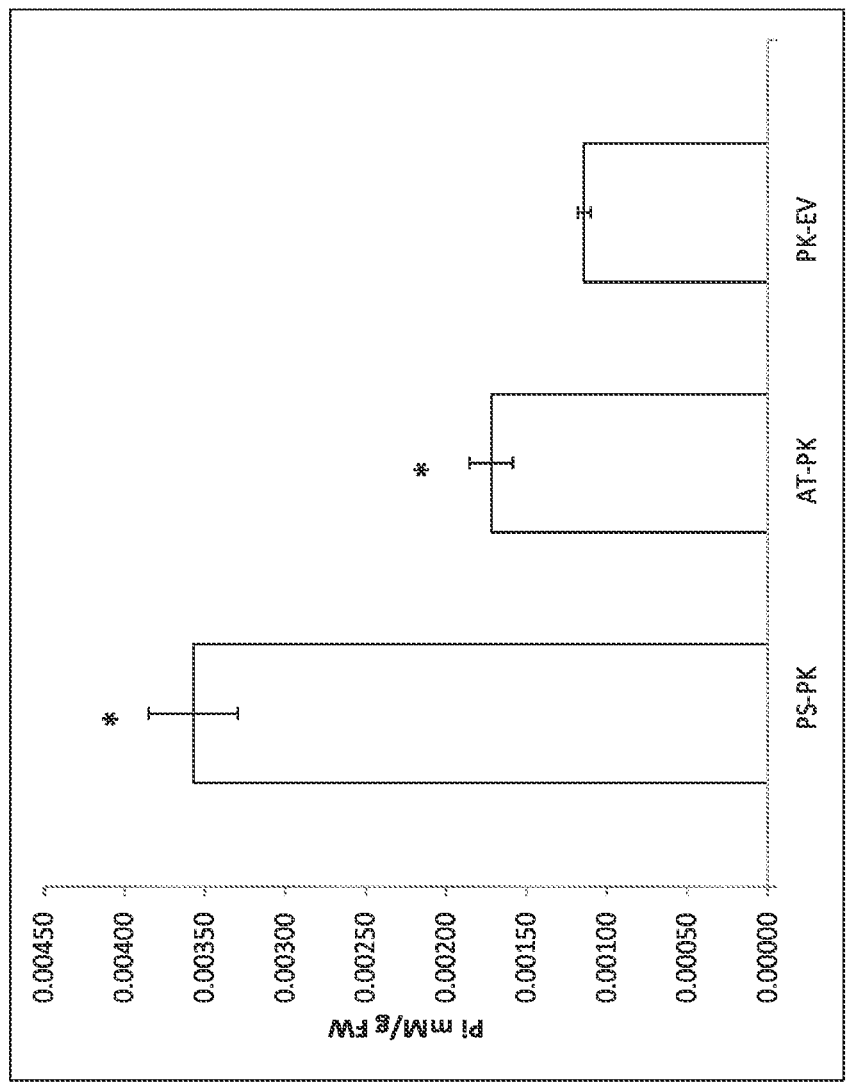
FIG. 1 is a bar chart showing phosphate uptake for cotton hairy root cultures transformed with pea apyrase psNTP9 (PS-PK), *Arabidopsis* apyrase AtAPY1 (AT-PK), and an empty vector control (PK-EV). Error bars represent standard error and asterisks above the bars indicate mean values that are statistically significantly different from one another (Student's t-test, P≤0.001; n≥6).

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of this disclosure, a number of terms are defined below. Terms defined herein have meanings as commonly understood by a person of ordinary skill in the areas relevant to the present disclosure. Terms such as "a," "an" and "the" are not intended to refer to only a singular entity, but include the general class of which a specific example may be used for illustration. The terminology herein is used to describe specific embodiments of the disclosure, but their usage does not delimit the disclosure, except as outlined in the claims.

For each embodiment according to the disclosure, the modified plant can be any monocot or dicot plant of interest, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Dicot plants for use in the present disclosure include, but are not limited to, canola, cotton, potato, quinoa, amaranth, buckwheat, safflower, soybean, sugarbeet, and sunflower. Monocots for use in the present disclosure include, but are not limited to, wheat, oat, barley, maize, rye, triticale, rice, ornamental and forage grasses, sorghum, millet, and sugarcane.

For each applicable embodiment according to the disclosure, the additional apyrase gene can be any known apyrase gene. The modified apyrase gene can be derived from any known apyrase gene. There are many known and published apyrase genes. (See e.g., Clark et al, 2014). Different apyrase genes can be found in different plants, and even within the same plant species there can be multiple known apyrase genes. Many of the apyrase genes share a very similar DNA sequence. The source apyrase gene can be modified such that the amino acid sequence encoded by the modified gene is the same or different than the amino acid sequence encoded by the source apyrase gene. In certain embodiments, the modified apyrase gene encodes the same amino acid sequence as the source apyrase gene. In another embodiment, the modified apyrase gene encodes a different amino acid sequence than the source apyrase gene. In a further embodiment, the modified apyrase gene encodes an amino acid sequence that contains 1, 2 or 3 amino acid changes relative to the amino acid sequence encoded by the source apyrase gene. Further, a plant modified to contain the modified apyrase gene generally exhibits one or more improved characteristics over the plant line from which it was derived. In various embodiments, the apyrase gene is a pea apyrase gene or an *Arabidopsis* apyrase gene.

In certain embodiments of the present disclosure, the modified plants and methods of making modified plants according to the disclosure generally have the feature of increased yield over the plant line from which it was derived. In another embodiment, the modified plant according to various embodiments of the disclosure exhibits an improvement over the plant line from which it was derived in one or more characteristics including increase in yield, phosphate uptake, drought resistance, disease resistance, fungal resistance, nutrient uptake, water uptake, average primary root length, average number of lateral roots, average number of seed pods, average seed pod size, average seed size, average seed weight, seed germination, seed survival, average number of siliques, average silique size, average leaf length, average leaf area, and average plant height.

In embodiments having an increase in yield, increase in phosphate uptake, increase in drought resistance, increase in disease resistance, increase in fungal resistance, increase in nutrient uptake, increase in water uptake, increase in primary root length, increase in average number of seed pods, increase in average seed pod size, increase in average seed size, increase in average seed weight, increase in average number of siliques, increase in average silique size, increase in average leaf length, increase in average leaf area, increase in average plant height, over the plant line from which it was derived is generally at least a 10% increase, at least a 20% increase, at least a 30% increase, at least a 50% increase, at least a 100% increase, or even at least a 200% increase. In further embodiments, the increase is about a 20-50% increase, a 50-100% increase, or a 100-200% increase.

EXAMPLES

Example 1

Two studies on crop plants revealed that constitutive expression of pea apyrase (psNTP9) can enhance the seed productivity of soybean and Arabidopsis grown on soil under conditions of normal or sub-normal fertilizer applications. Additionally, this enhanced apyrase expression can promote the uptake of phosphate into the roots of plants, even at concentrations of phosphate lower than 2 mM, such as those typically found in fertilizers. Finally a modified version of psNTP9 was generated that promotes phosphate uptake even more than the wild-type psNTP9.

Transformation: Arabidopsis WS and Col-0 ecotypes were transformed with psNTP9 using previously described methods (Zhang et al., 2006, relevant methods incorporated herein by reference). Soybean and cotton hairy root cultures were transformed with psNTP9 and modified versions of psNTP9 using previously described methods (Cho et al., 2000; Kim, 2013, relevant methods incorporated herein by reference). Soybean (*Glycine max* (L.) Merr.), genotype Williams 82, plants were transformed with psNTP9 and modified psNTP9 using previously described methods (Paz et al., 2006; Luth et al., 2015, relevant methods incorporated herein by reference).

Ten to 15 plants of *A. thaliana* ecotype Col-0 and WS were grown in 4-inch pots. The psNTP9 gene was cloned into a Gateway cloning vector pH7WG2, under the control of 35S CaMV promoter, and was introduced into the *A. tumefaciens* strain GV3101. *A. tumefaciens* stocks were grown on solidified LB medium with 50 mg/L gentamicin and 50 mg/L spectinomycin and incubated at 28° C. until colony formation. Liquid LB medium containing antibiotics was inoculated with a single colony and shaken at 250 rpm at 28° C. The *A. tumefaciens* culture was centrifuged and the pellets were re-suspended in the infiltration medium (containing 5% sucrose and 0.05% Silwet L-77, pH adjusted to 5.7) to a final $OD_{600}$=0.80 prior to use. The Arabidopsis plants were transformed by floral dip method, adapted from Clough and Bent (1998) and Zhang et al. (2006). The inoculum was added to a beaker, plants were inverted into this suspension such that all above-ground tissues were submerged, and plants were then removed after 3-5 seconds of gentle agitation. Plants were covered and left in a low light or dark location overnight and returned to the greenhouse the next day. Care was taken to keep the covered plants out of direct sunlight. Covers were removed approximately 12-24 hours after treatment and the plants were grown for 3-5 weeks until siliques were brown and dry, keeping the bolts from each pot together and separated from neighboring pots. Seeds for putative transformants were collected, surface sterilized, cold-treated for 3 days and plated on hygromycin selection plates and then grown for 7-10 days. Transformants were identified as hygromycin-resistant seedlings that produced green leaves and well-established roots within the selective medium. The transformants were grown to maturity by transplanting them to soil.

Soybean (*G. max*), genotype Williams 82, plants were transformed with psNTP9 and modified psNTP9 using the methods described by Paz et al. (2006) and Luth et al. (2015), relevant methods incorporated herein by reference, with slight modifications. The psNTP9 gene was cloned into a Gateway™ cloning vector pB7WG2 under the control of 35S CaMV promoter, and was then introduced into *A. tumefaciens* (strain EHA101). *A. tumefaciens* stocks of EHA101/pB7WG2-psNTP9 were grown on solidified YEP medium with 50 mg/L kanamycin and 50 mg/L spectinomycin and incubated at 28° C. until colony formation. Positive colonies were grown in 50 mL of liquid YEP medium containing antibiotics until $OD_{620}$=0.8-1.0 was reached. The *A. tumefaciens* culture was centrifuged and pellets were re-suspended in the infection medium containing 1/10 strength Gamborg B-5 media with 200 μM acetosyringone. Soybean seeds were surface sterilized using chlorine gas for 12 hours. Approximately 16 hours prior to the infection with *A. tumefaciens* culture, sterile $ddH_2O$ was added to the sterilized seeds until the seeds were 2/3 covered and then incubated overnight in the dark at 24° C. The seed coat was removed, and then a longitudinal cut along the hilum was made to separate two cotyledonary node explants. The primary shoot was subsequently removed and the cotyledonary node was wounded by cutting gently. Explants were infected with *Agrobacterium* suspension for 20-30 minutes at room temperature. After inoculation, the half seeds were transferred to a sterile paper towel with adaxial side up and then transferred to the Co-Cultivation Medium containing 1/10 strength Gamborg B-5 media with 400 mg/L cysteine, 154.2 mg/L DTT and 200 μM acetosyringone. The cultures were incubated at 24° C. for 5 days in the dark. After 5 days of co-cultivation, the explants were cultured onto shoot induction medium containing full-strength Gamborg B-5 media with 100 mg/L Timentin®, 100 mg/L cefotaxime, 50 mg/L vancomycin, and 8 mg/L ammonium glufosinate. The cultures were incubated at 24° C., 18:6 photoperiod 150 μM/m²/s for 14 days. The cultures were further transferred to the Shoot Elongation Medium containing full-strength MS Medium with Gamborg Vitamins with 50 mg/L asparagine, 100 mg/L L-pyroglutamic acid, 0.1 mg/L IAA, 0.5 mg/L $GA_3$, 1 mg/L ZR, 100 mg/L Timentin®, 100 mg/L cefotaxime, 50 mg/L vancomycin, and 8 mg/L ammonium glufosinate. After 8 weeks, when the elongated shoots were at least 3-4 cm long, shoots close to the shoot pads were excised and transferred to the Rooting Medium containing half-strength MS Medium with Gamborg Vitamins with 1 mg/L IBA and 3 mg/L ammonium glufosinate. After 2-3 weeks, the elongated shoots with healthy-appearing roots were gently removed from the rooting medium and transplanted into pots with soil mix (Redi-Earth® Peat-Lite®). Plantlets were then watered 1/4 strength 20-20-20 (N-P-K) liquid plant fertilizer. The plantlets were grown at 24° C. and 16:8 hour photoperiods. Positive $T_0$ plants with bar gene resistance were confirmed by applying ammonium glufosinate herbicide solution. Eight seeds from positive T₀ plants were planted in soil and tested again for bar gene resistance. Three of the four transgenic soybean lines were stably inherited in a 3:1 segregation ratio in the $T_1$ progeny.

Growth assays-primary root length and leaf area in *Arabidopsis*: Modified Murashige and Skoog (MS) with no sugar and no phosphate (pH 5.7) containing 0.8% agar medium was used as growth medium. All chemicals used were from Sigma Aldrich.

Wild-type *A. thaliana* (Ecotypes Columbia and Wassilewskija) and transgenics were sterilized and stratified (72 hours). The seeds were grown on modified MS medium with no phosphate in a growth chamber at 22-24° C. Plants were grown vertically under continuous light 130-150 μM/m²/s for 3 weeks.

The primary root length and leaf-area were analyzed using ImageJ 1997, Software (e.g. Abramoff et al., 2004).

Growth assays in *Arabidopsis* using different amount of fertilizer: Wild-type *A. thaliana* (Ecotype Columbia) and the transgenic seeds sterilized and stratified (72 hours) were grown in soil with half fertilizer and full fertilizer. The soil mix containing 75% Pro-Mix® Biofungicide and wetting agent, with 25% Profile™ Field and Fairway™ Calcined Clay (0.2-0.5 cm granules) was used. Fourteen grams (g) and 28 g of Osmocote® 14-14-14 (polymer resin coated granular slow release fertilizer, 3-4 months) was used as half and full fertilizer respectively.

The plants were grown at 22° C. with 16 hours light/8 hours dark conditions. The number of siliques was counted from individual plants after 5-6 weeks (once the plants stopped flowering completely and the siliques were still green). The plants were further allowed to dry for 3-4 weeks, and the seeds were harvested and collected from individual plant and the seed weight was measured.

Additional growth assays in *Arabidopsis* using different amount of fertilizer: wild-type seeds (Col-0), homozygous T3 transgenic seeds (OE-4 and OE-5 are highly expressing lines; OE-1, OE-2, OE-3 and OE-6 are moderately expressing lines) and empty vector controls (EV-1 and EV-2) were grown in 3:1 Pro-Mix® Biofungicide and Profile™ Field and Fairway™ calcined clay (0.2-0.5 cm diameter) and watered regularly with Gnatrol® to prevent gnats. The plants were observed for the morphological characters and the silique number was counted after 7 weeks of planting (when the plants are just done with silique formation). After approximately 8-9 weeks, the plants were no longer watered and the siliques were allowed to dry within the plants. The seeds were harvested from the siliques from individual plants, and weighed separately. For full fertilizer: 75% Pro-Mix® Biofungicide and wetting agent; 25% Profile™ Field and Fairway™ calcined clay (0.2-0.5 cm granules) and Osmocote™ 14-14-14: 28 ml/9 L of the soil mix. For half fertilizer: 75% Pro-Mix® Biofungicide and wetting agent; 25% Profile™ Field and Fairway™ calcined clay (0.2-0.5 cm granules) and Osmocote® 14-14-14: 14 ml/10 L of the soil mix. For no fertilizer: 75% Pro-Mix® Biofungicide and wetting agent; 25% Profile™ Field and Fairway™ calcined clay (0.2-0.5 cm granules). Osmocote® Classic (total nitrogen (N)=14% (8.2% ammonical nitrogen; 5.8% nitrate nitrogen); available phosphate ($P_2O_5$)=14%; soluble potash ($K_2O$)=14%) is a slow release fertilizer and there is no additional fertilizer added during watering.

Phosphate Content Assay: Pi content was analyzed as described by Ren et al., 2012. Fresh hairy root tissue was weighed and frozen with liquid nitrogen and homogenized with the extraction buffer (10 mM Tris, 1 mM EDTA, 100 mM NaCl, 1 mM β-mercaptoethanol and 1 mM Pefabloc®, pH 8.0) at a ratio of 1 mg of sample (fresh weight) to 10 μL of extraction buffer. A total of 100 μL of homogenized sample was mixed with 900 μL of 1% glacial acetic acid, and incubated at 42° C. for 30 minutes. The solution was then centrifuged at 10,500 rpm for 5 minutes, and 300 μL of the supernatant aliquot was used in Pi assay. The reaction containing 700 μL of assay solution (0.35% ammonium orthomolybdate, 0.86 N $H_2SO_4$, and 1.4% ascorbic acid) and 300 μL of sample was incubated at 42° C. for 30 minutes. Pi content was measured at $A_{820}$.

FIG. 1 is a bar chart showing phosphate uptake for cotton hairy root cultures transformed with one of pea apyrase psNTP9 (PS-PK), *Arabidopsis* apyrase AtAPY1 (AT-PK), and an empty vector control (PK-EV). Phosphate uptake is statistically significantly increased in cotton hairy root cultures transformed with psNTP9 (PS-PK) or *Arabidopsis* apyrase AtAPY1, (AT-PK) compared to empty vector control (PK-EV).

Figure 2:
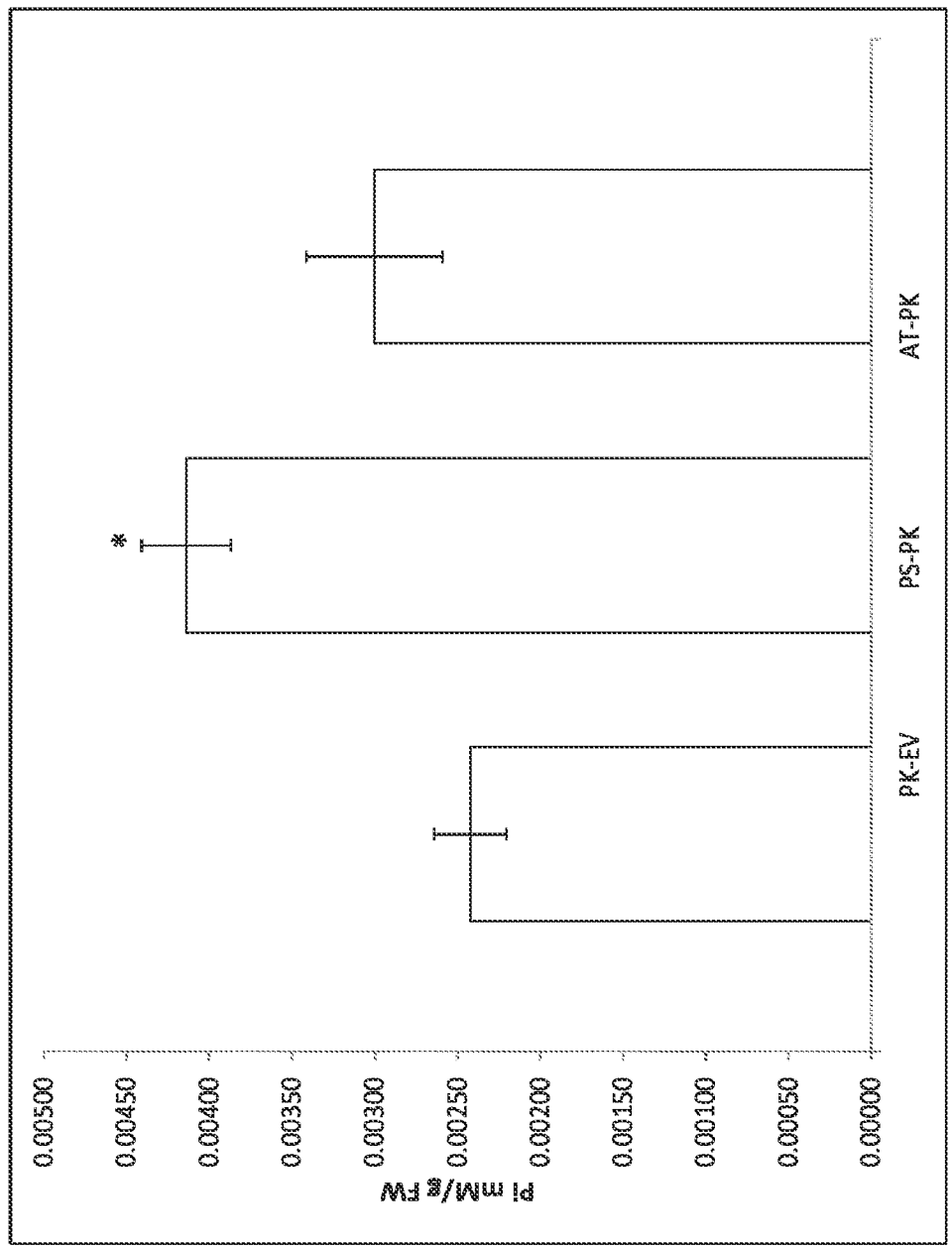
FIG. 2 is a bar chart showing phosphate uptake for soybean hairy root cultures transformed with pea apyrase psNTP9 (PS-PK), *Arabidopsis* apyrase AtAPY1 (AT-PK), and an empty vector control (PK-EV). Error bars represent standard error and asterisks above the bars indicate mean values that are statistically significantly different from one another (Student's t-test, P≤0.001; n≥10).

FIG. 2 is a bar chart showing phosphate uptake for soybean hairy root cultures transformed with pea apyrase psNTP9 (PS-PK), *Arabidopsis* apyrase AtAPY1 (AT-PK), or an empty vector control (PK-EV). Phosphate uptake is statistically significantly increased in soybean hairy root cultures transformed with psNTP9 (PS-PK) compared to cultures transformed with *Arabidopsis* apyrase, AtAPY1, (AT-PK) and the empty vector control (PK-EV).

Figure 3:
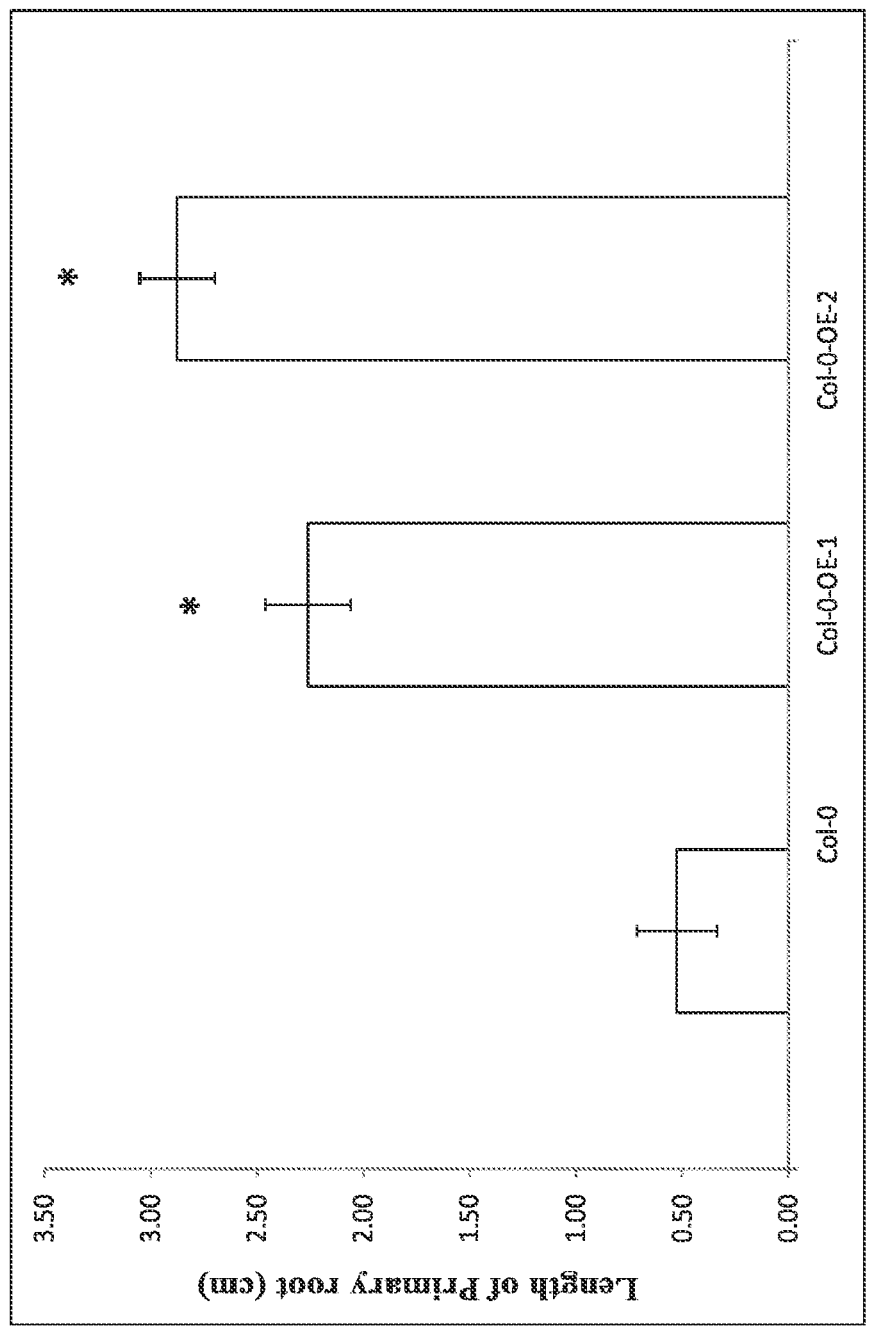
FIG. 3 is a bar chart showing primary root length for 3-week old *Arabidopsis* seedlings transformed with pea apyrase psNTP9 (Col-0-OE-1 and Col-0-OE-2) compared to Col-0 wild-type control (Col-0) when grown in the absence of phosphate. Error bars represent standard error and asterisks above the bars indicate mean values that are statistically significantly different from one another (Student's t-test, P≤0.001; n≥4).

FIG. 3 is a bar chart showing primary root length for 3-week old *Arabidopsis* seedlings transformed with pea apyrase psNTP9 (Col-0-OE-1 and Col-0-OE-2) compared to Col-0 wild-type control (Col-0) when grown in the absence of phosphate. Primary root length is statistically significantly longer in 3-week old seedlings transformed with psNTP9 (Col-0-OE-1 and Col-0-OE-2) compared to Col-0 wild-type control (Col-0).

Figure 4:
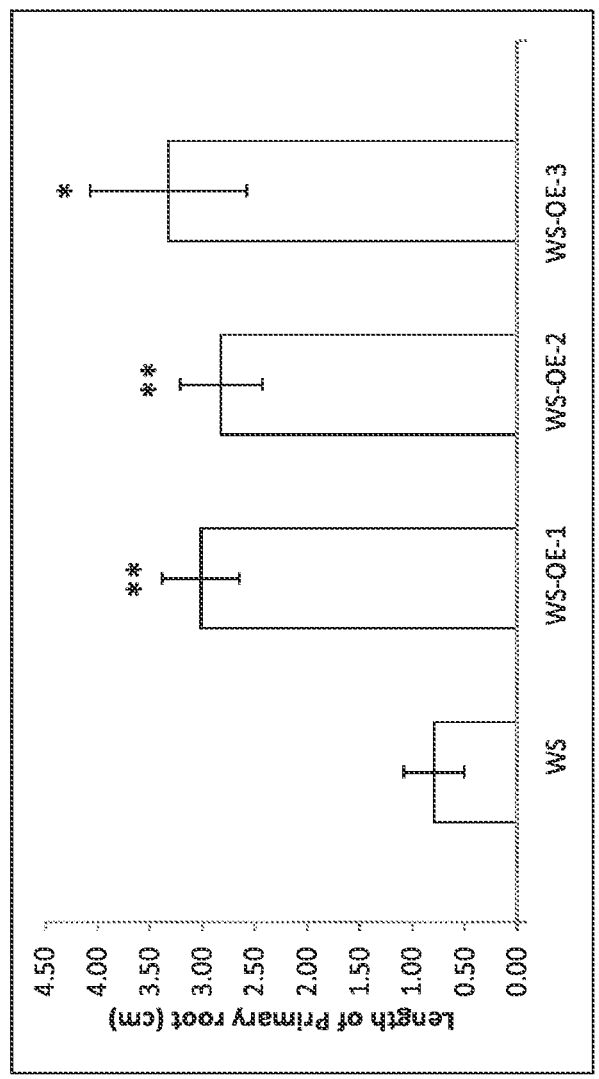
FIG. 4 is a bar chart showing primary root length for 3-week old *Arabidopsis* seedlings for three independent lines transformed with pea apyrase psNTP9 (WS-OE-1, WS-OE-2 and WS-OE-3) compared to wild-type control (WS) when grown in the absence of phosphate. Error bars represent standard error and asterisks above the bars indicate mean values that are statistically significantly different from one another (Student's t-test, ** indicates P≤0.005; * indicates P≤0.05; n≥2).

FIG. 4 is a bar chart showing primary root length for 3-week old *Arabidopsis* seedlings for three independent lines transformed with pea apyrase psNTP9 (WS-OE-1, WS-OE-2 and WS-OE-3) compared to wild-type control (WS) when grown in the absence of phosphate. Primary root length is statistically significantly longer in 3-week old seedlings for all three independent lines transformed with psNTP9 (WS-OE-1, WS-OE-2 and WS-OE-3) compared to WS wild-type control (WS).

Figure 5:
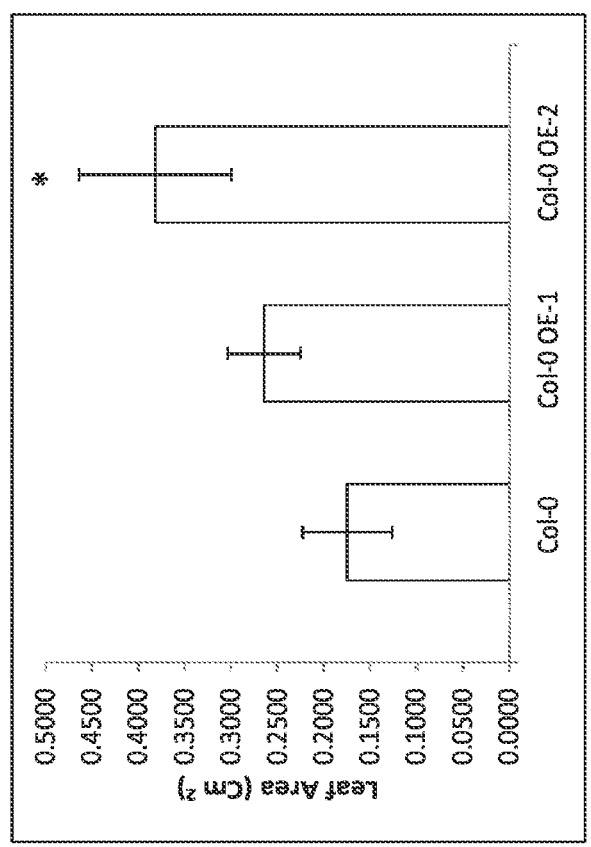
FIG. 5 is a bar chart showing leaf area for 3-week old *Arabidopsis* seedlings grown in the absence of phosphate for two independent lines transformed with psNTP9 (Col-0-OE-1 and Col-0-OE-2) compared to Col-0 wild-type control (Col-0) when grown in the absence of phosphate. Error bars represent standard error and asterisks above the bars indicate mean values that are statistically significantly different from one another (Student's t-test, * indicates P≤0.07; n≥5).

FIG. 5 is a bar chart showing leaf area for 3-week old *Arabidopsis* seedlings grown in the absence of phosphate for two independent lines transformed with psNTP9 (Col-0-OE-1 and Col-0-OE-2) compared to Col-0 wild-type control (Col-0) when grown in the absence of phosphate. Leaf area is statistically significantly larger in 3-week old seedlings grown in the absence of phosphate for one independent line transformed with psNTP9 (Col-0-OE-2) compared to Col-0 wild-type control (Col-0) when grown in the absence of phosphate.

Figure 6:
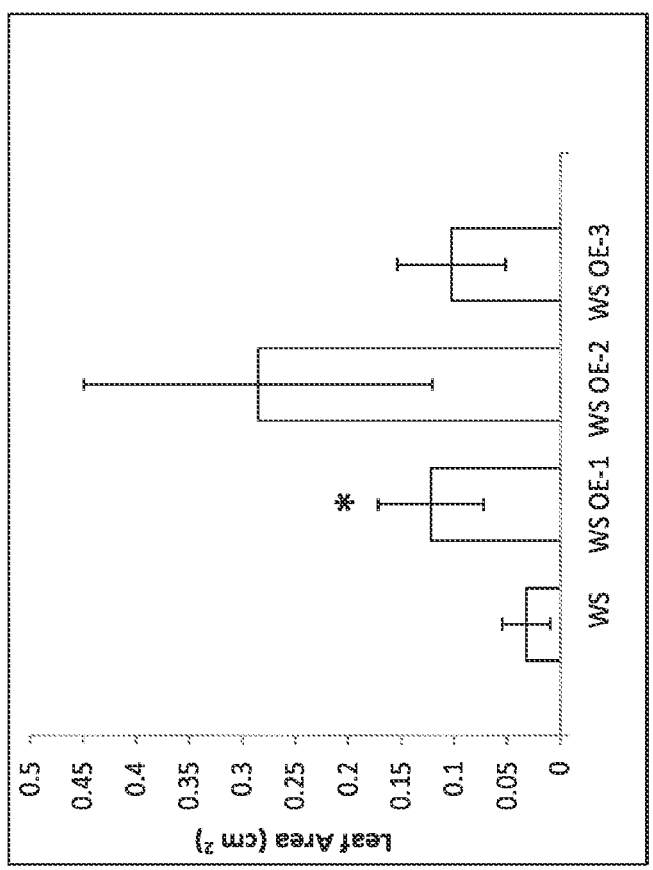
FIG. 6 is a bar chart showing leaf area for 3-week old *Arabidopsis* seedlings grown in the absence of phosphate for three independent lines transformed with psNTP9 (WS-OE-1, WS-OE-2 and WS-OE-3) compared to WS wild-type control (WS) when grown in the absence of phosphate. Error bars represent standard error and asterisks above the bars indicate mean values that are statistically significantly different from one another (Student's t-test, * indicates P≤0.01; n≥2).

FIG. 6 is a bar chart showing leaf area for 3-week old *Arabidopsis* seedlings grown in the absence of phosphate for three independent line transformed with psNTP9 (WS-OE-1, WS-OE-2 and WS-OE-3) compared to WS wild-type control (WS) when grown in the absence of phosphate. Leaf area is statistically significantly larger in 3-week old seedlings grown in the absence of phosphate for one independent line transformed with psNTP9 (WS OE-1) compared to WS wild-type control (WS) when grown in the absence of phosphate.

Figure 7:
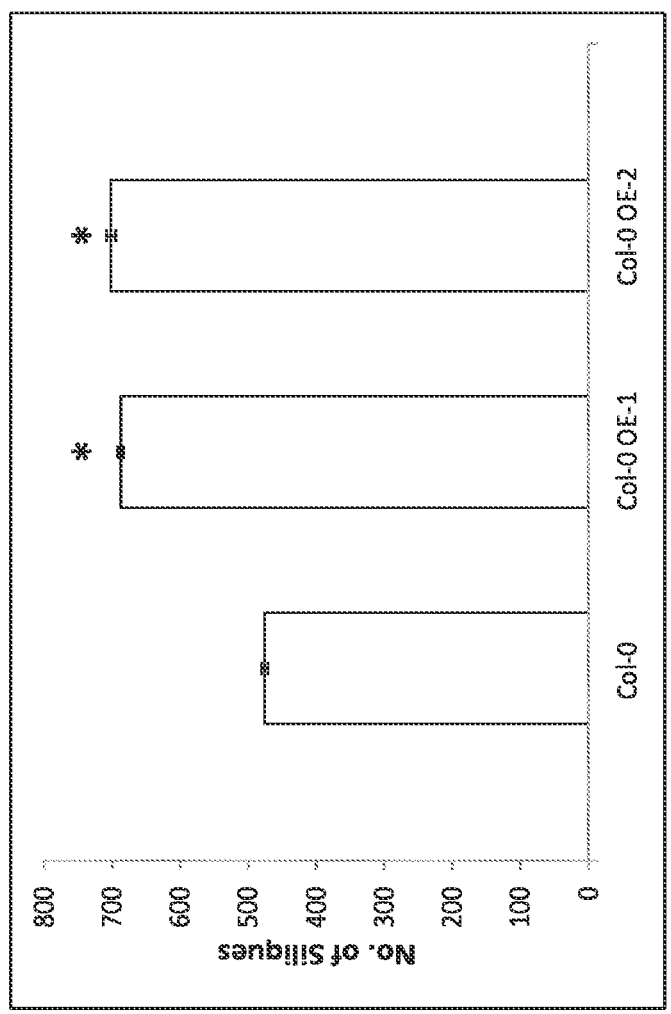
FIG. 7 a bar chart showing the silique (seed pod) number produced by mature *Arabidopsis* plants for two independent lines transformed with psNTP9 (Col-0-OE-1 and Col-0-OE-2) compared to Col-0 wild-type control (Col-0). Error bars represent standard error and asterisks above the bars indicate mean values that are statistically significantly different from one another (Student's t-test, *=P≤0.02; n≥9).

FIG. 7 a bar chart showing the silique (seed pod) number produced by mature *Arabidopsis* plants for two independent lines transformed with psNTP9 (Col-0-OE-1 and Col-0-OE-2) compared to Col-0 wild-type control (Col-0). The silique number produced by mature *Arabidopsis* plants is statistically significantly higher in both lines transformed with psNTP9 (Col-0-OE1 and Col-0 OE2) compared to wild-type control plants (Col-0) when grown under full fertilizer conditions.

Figure 8:
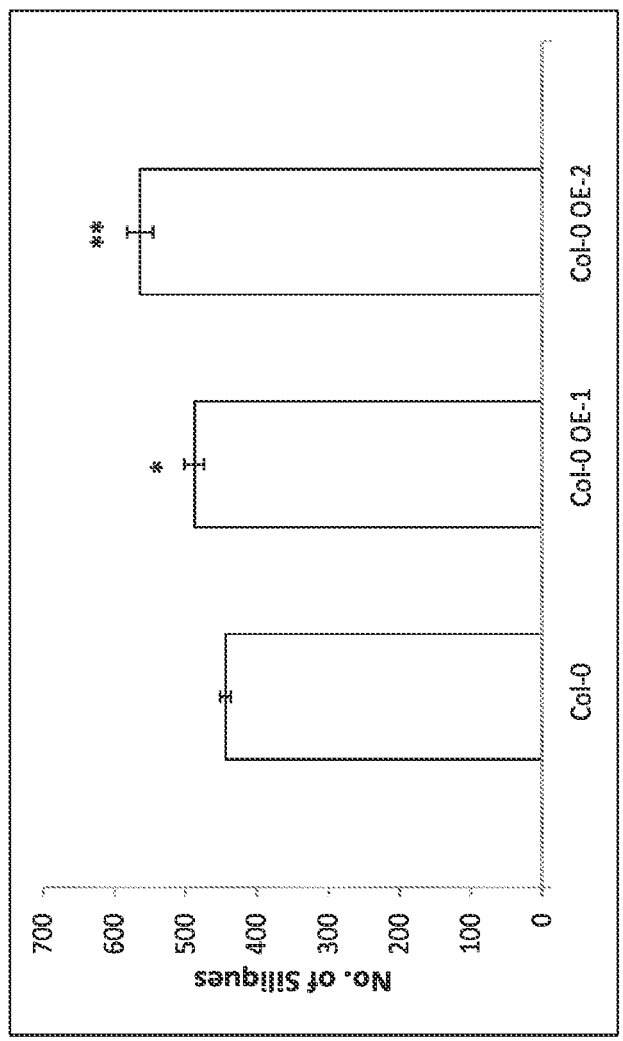
FIG. 8 is a bar chart showing the silique number produced by mature *Arabidopsis* plants for two independent lines transformed with psNTP9 (Col-0-OE-1 and Col-0-OE-2) compared to Col-0 wild-type control (Col-0). Error bars represent standard error and asterisks above the bars indicate mean values that are statistically significantly different from one another (Student's t-test, * P≤0.05; ** P≤0.005 n≥8).

FIG. 8 is a bar chart showing the silique number produced by mature *Arabidopsis* plants for two independent lines transformed with psNTP9 (Col-0-OE-1 and Col-0-OE-2) compared to Col-0 wild-type control (Col-0). Silique number produced by mature *Arabidopsis* plants is statistically significantly higher in both lines transformed with psNTP9 (Col-0-OE1 and Col-0 OE2) compared to wild-type control plants (Col-0) when grown under half fertilizer conditions.

Figure 9:
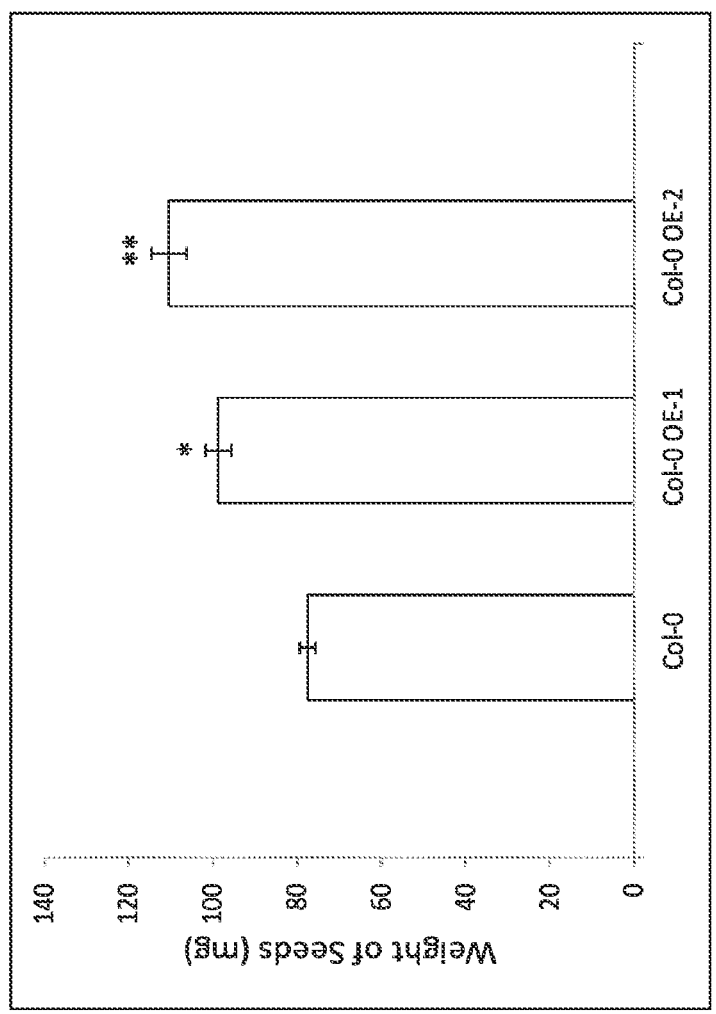
FIG. 9 is a bar chart showing average seed weight produced by mature *Arabidopsis* plants for two independent lines transformed with psNTP9 (Col-0-OE-1 and Col-0-OE-2) compared to Col-0 wild-type control (Col-0). Error bars represent standard error and asterisks above the bars indicate mean values that are statistically significantly different from one another (Student's t-test, *=P≤0.0001; **=P≤0.000002; n≥8).

FIG. 9 is a bar chart showing average seed weight produced by mature *Arabidopsis* plants for two independent lines transformed with psNTP9 (Col-0-OE-1 and Col-0-OE-2) compared to Col-0 wild-type control (Col-0). Average seed weight produced by mature *Arabidopsis* plants is statistically significantly higher in both lines transformed with psNTP9 (Col-0-OE1 and Col-0 OE2) compared to wild-type control plants (Col-0) when grown under full fertilizer conditions.

Figure 10:
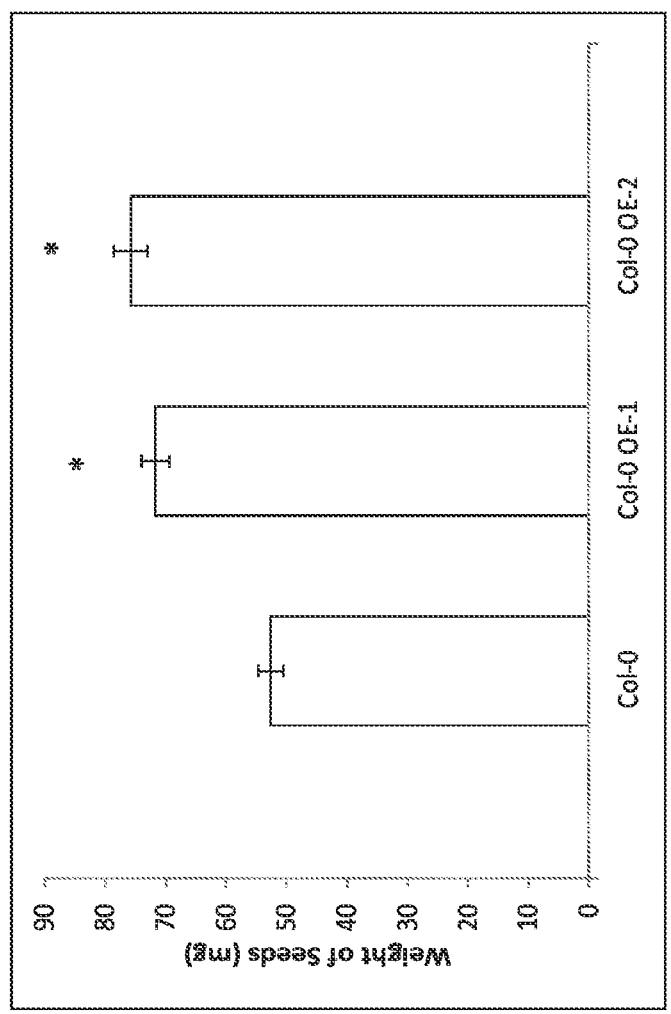
FIG. 10 is a bar chart showing average seed weight produced by mature *Arabidopsis* plants for two independent lines transformed with psNTP9 (Col-0-OE-1 and Col-0-OE-2) compared to Col-0 wild-type control (Col-0). Error bars represent standard error and asterisks above the bars indicate mean values that are statistically significantly different from one another (Student's t-test, *=P≤0.000005; n≥8).

FIG. 10 is a bar chart showing average seed weight produced by mature *Arabidopsis* plants for two independent lines transformed with psNTP9 (Col-0-OE-1 and Col-0-OE-2) compared to Col-0 wild-type control (Col-0). Average seed weight produced by mature *Arabidopsis* plants is statistically significantly higher in both lines transformed with psNTP9 (Col-0-OE1 and Col-0 OE2) compared to wild-type control plants (Col-0) when grown under half fertilizer conditions.

Figure 11:
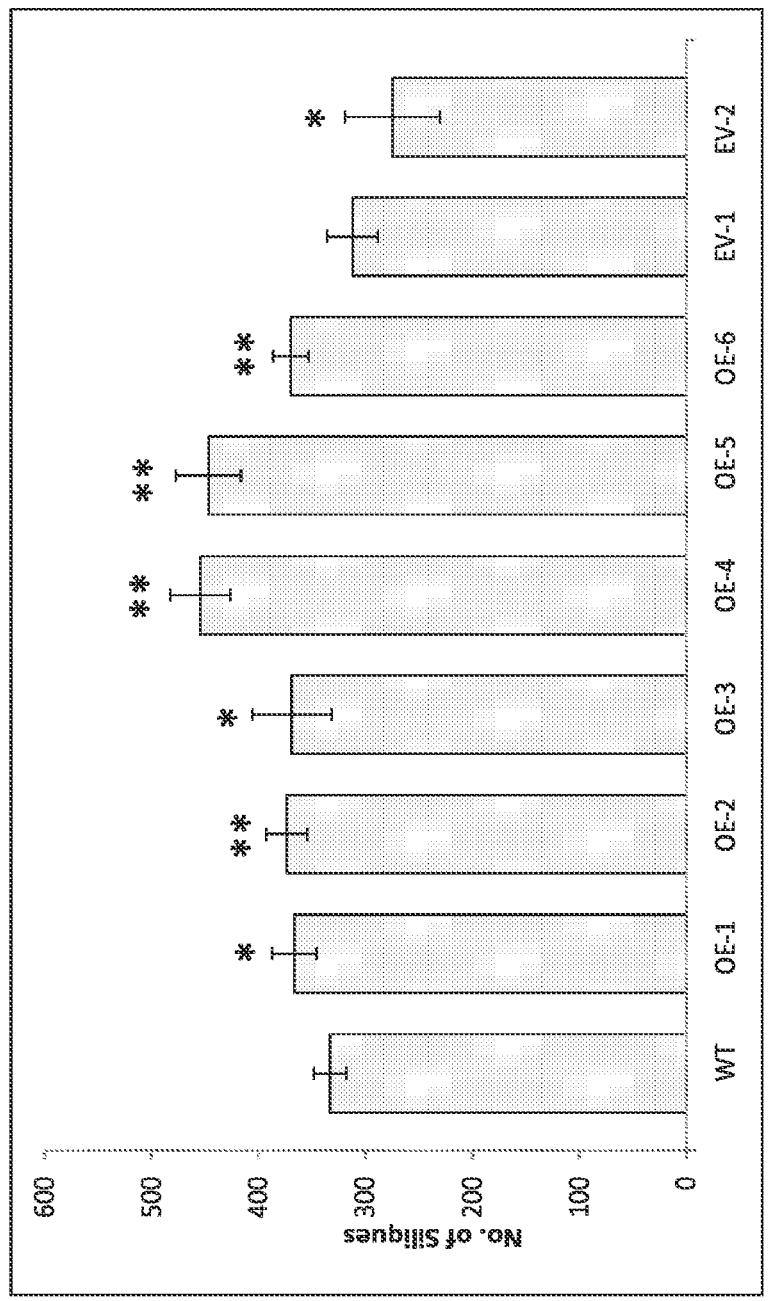
FIG. 11 is a bar chart showing the silique number produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in no fertilizer. Error bars represent standard deviation and asterisks above the bars indicate mean values that are statistically significantly different from one another (Student's t-test, * P≤0.05; ** P≤0.005; n=6).

FIG. 11 is a bar chart showing the silique number produced by mature *Arabidopsis* plants grown in no fertilizer. Silique number produced by mature *Arabidopsis* plants when grown with no fertilizer is statistically significantly higher in lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 12:
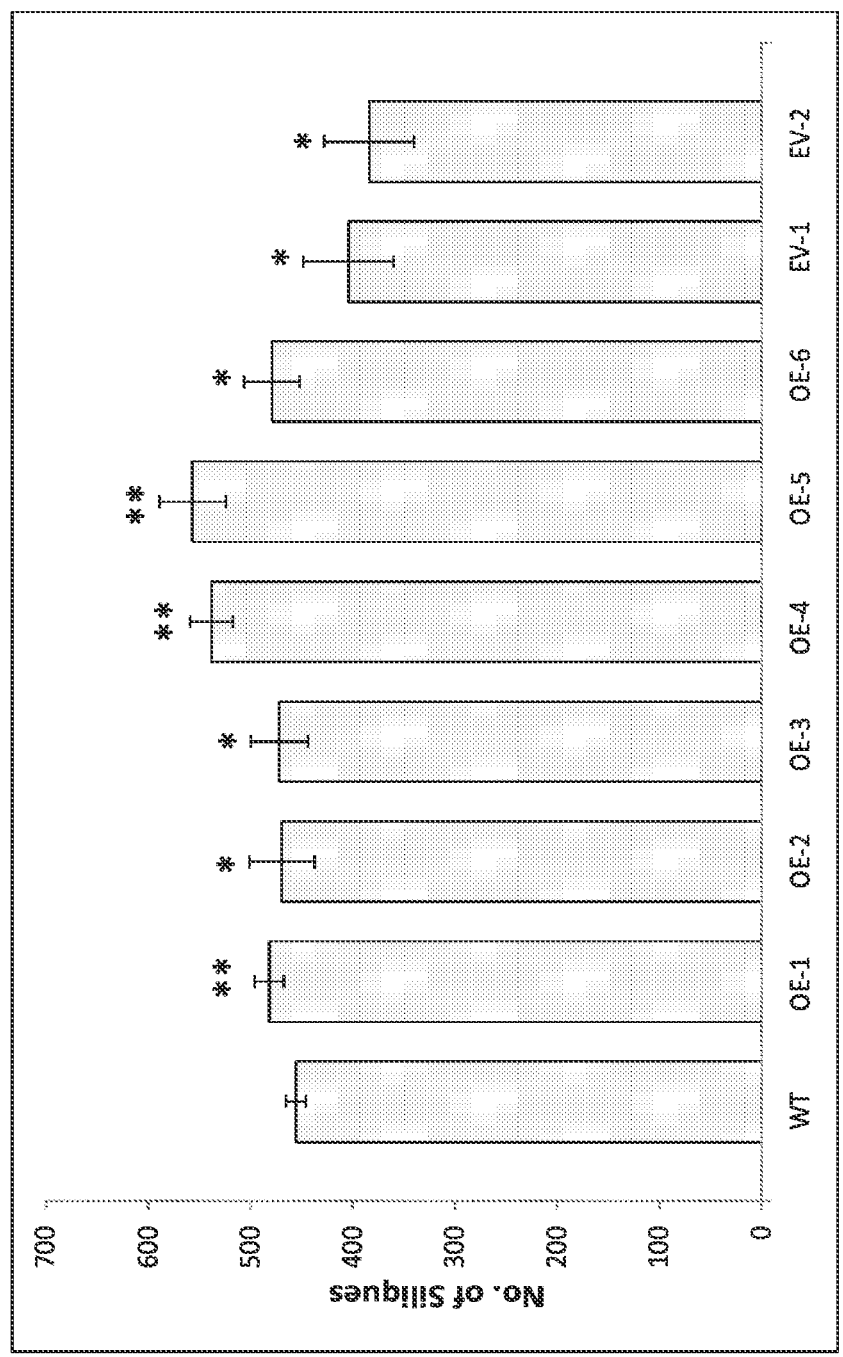
FIG. 12 is a bar chart showing the silique number produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in half fertilizer. Error bars represent standard deviation and asterisks above the bars indicate mean values that are statistically significantly different from one another (Student's t-test, * P≤0.05; ** P≤0.005; n=6).

FIG. 12 is a bar chart showing the silique number produced by mature *Arabidopsis* plants grown in half fertilizer. Silique number produced by mature *Arabidopsis* plants when grown with half fertilizer is statistically significantly higher in lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 13:
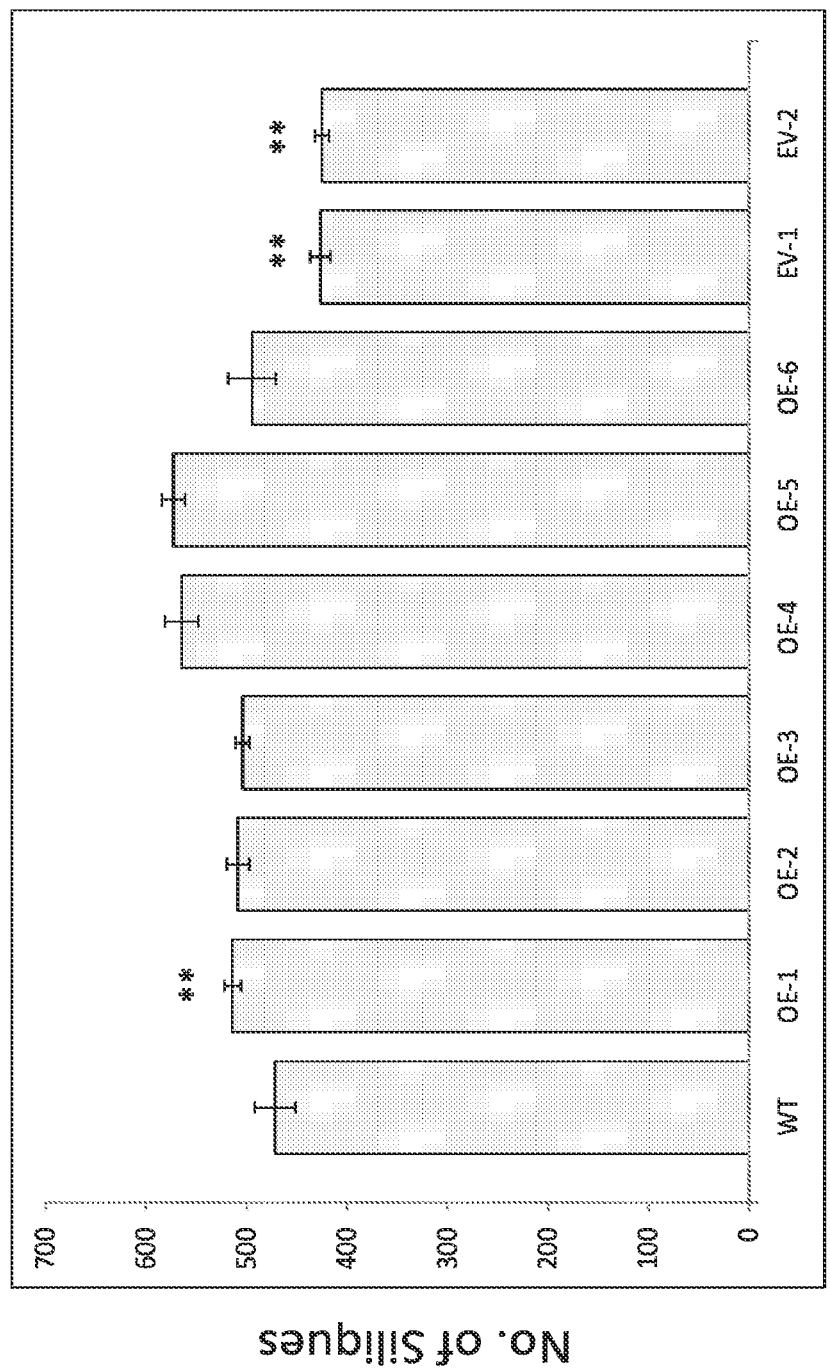
FIG. 13 is a bar chart showing the silique number produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in full fertilizer. Error bars represent standard deviation and asterisks above the bars indicate mean values that are statistically significantly different from one another (Student's t-test, * P≤0.05; ** P≤0.005; n=6).

FIG. 13 is a bar chart showing the silique number produced by mature *Arabidopsis* plants grown in full fertilizer. Silique number produced by mature *Arabidopsis* plants when grown with full fertilizer is statistically significantly higher in most of the lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 14:
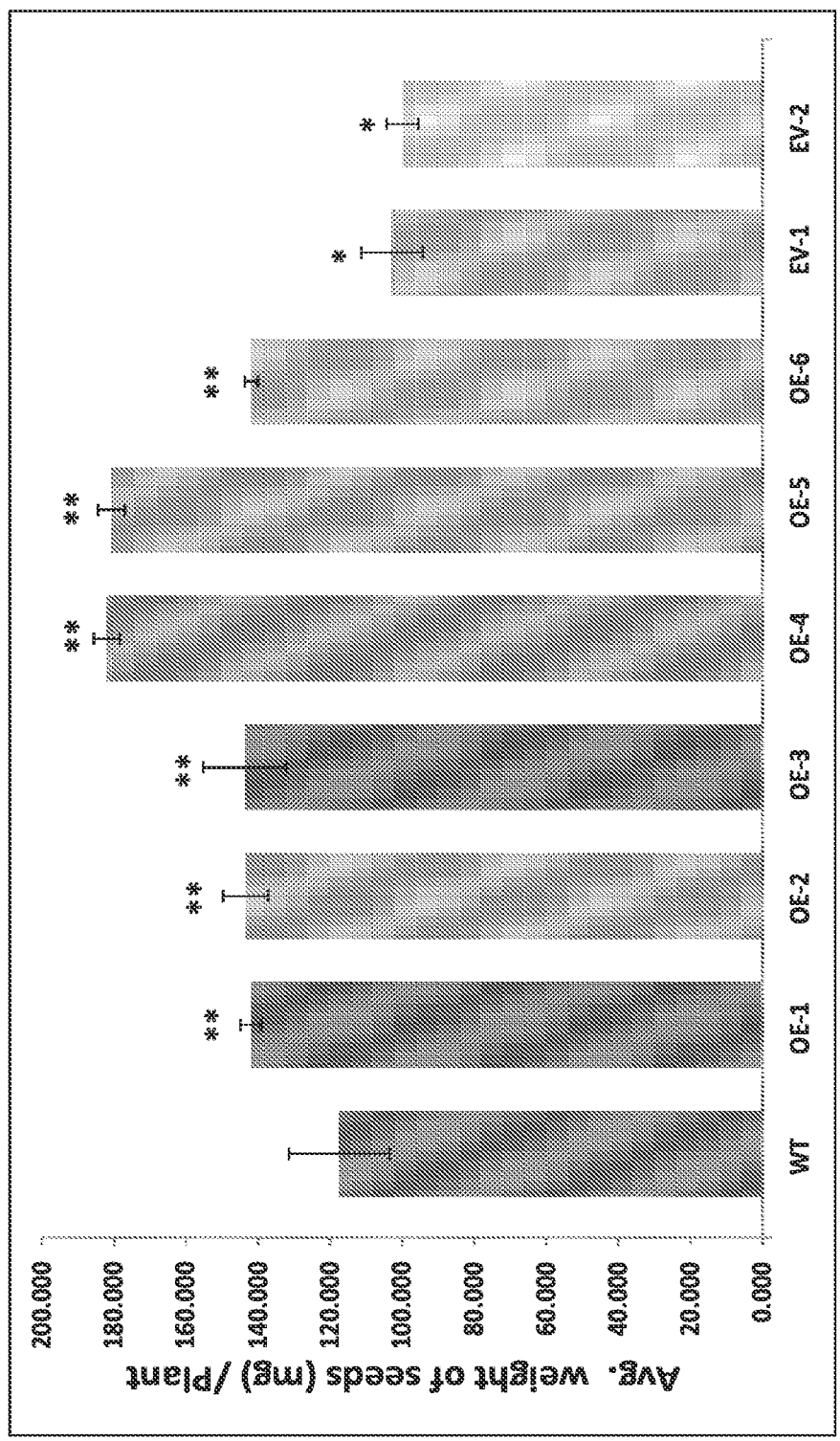
FIG. 14 is a bar chart showing average seed weight (mg/plant) produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in no fertilizer. Error bars represent standard deviation and asterisks above the bars indicate mean values that are statistically significantly different from one another (Student's t-test, * P≤0.05; ** P≤0.0005; n=6).

FIG. 14 is a bar chart showing average seed weight (mg/plant) produced by mature *Arabidopsis* plants grown in no fertilizer. Seed weight produced by mature *Arabidopsis* plants when grown with no fertilizer is statistically significantly higher in lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 15:
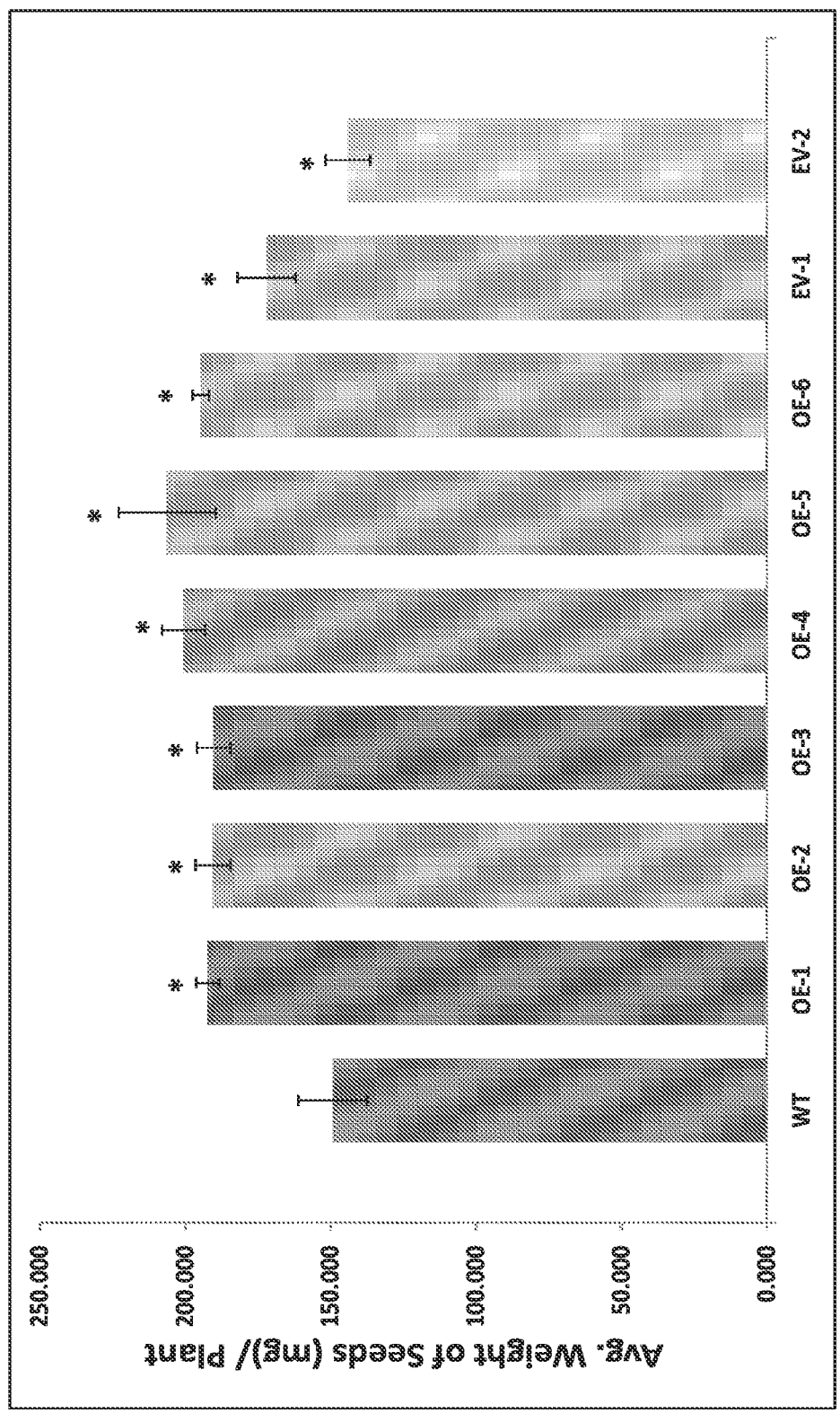
FIG. 15 is a bar chart showing average seed weight (mg/plant) produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in half fertilizer. Error bars represent standard deviation and asterisks above the bars indicate mean values that are statistically significantly different from one another (Student's t-test, * P≤0.05; ** P≤0.0005; n=6).

FIG. 15 is a bar chart showing average seed weight (mg/plant) produced by mature *Arabidopsis* plants grown in half fertilizer. Seed weight produced by mature *Arabidopsis* plants when grown with half fertilizer is statistically significantly higher in lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 16:
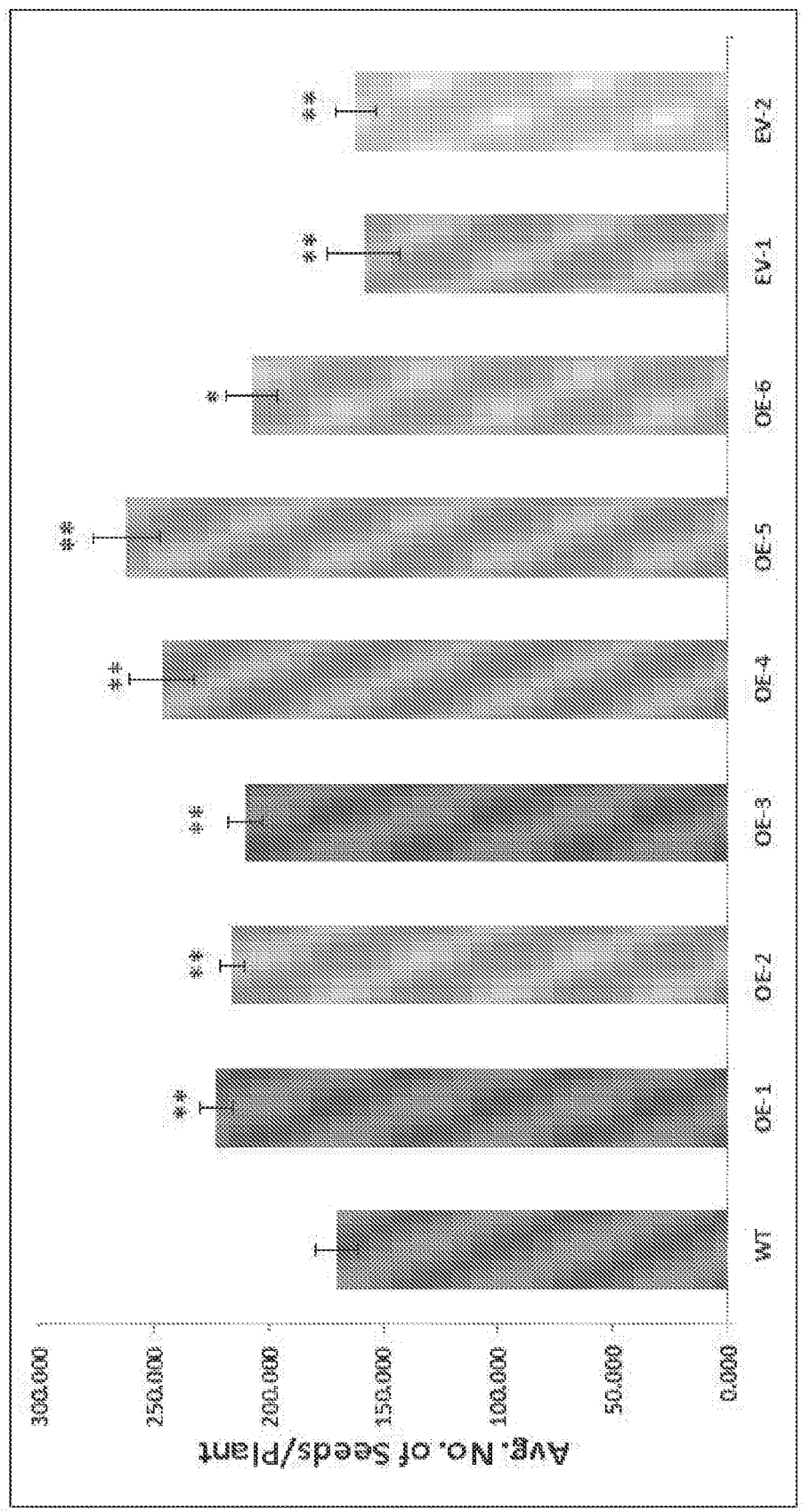
FIG. 16 is a bar chart showing average seed weight (mg/plant) produced by mature wild-type (WT), psNTP9 transformed (OE-4 and OE-5=highly expressing lines; OE-1, OE-2, OE-3 and OE-6=moderately expressing lines), and empty vector control (EV-1 and EV-2) *Arabidopsis* plants grown in full fertilizer. Error bars represent standard deviation and asterisks above the bars indicate mean values that are statistically significantly different from one another (Student's t-test, * P≤0.05; ** P≤0.0005; n=6).

FIG. 16 is a bar chart showing average seed weight (mg/plant) produced by mature *Arabidopsis* plants grown in full fertilizer. Seed weight produced by mature *Arabidopsis* plants when grown with full fertilizer is statistically significantly higher in lines transformed with psNTP9 (OE-4 and OE-5=highly expressing lines; OE-1, OE-2, OE-3 and OE-6=moderately expressing lines) compared to Col-0 wild-type control (WT) and empty vector (EV-1 and EV-2) control plants.

Figure 17:
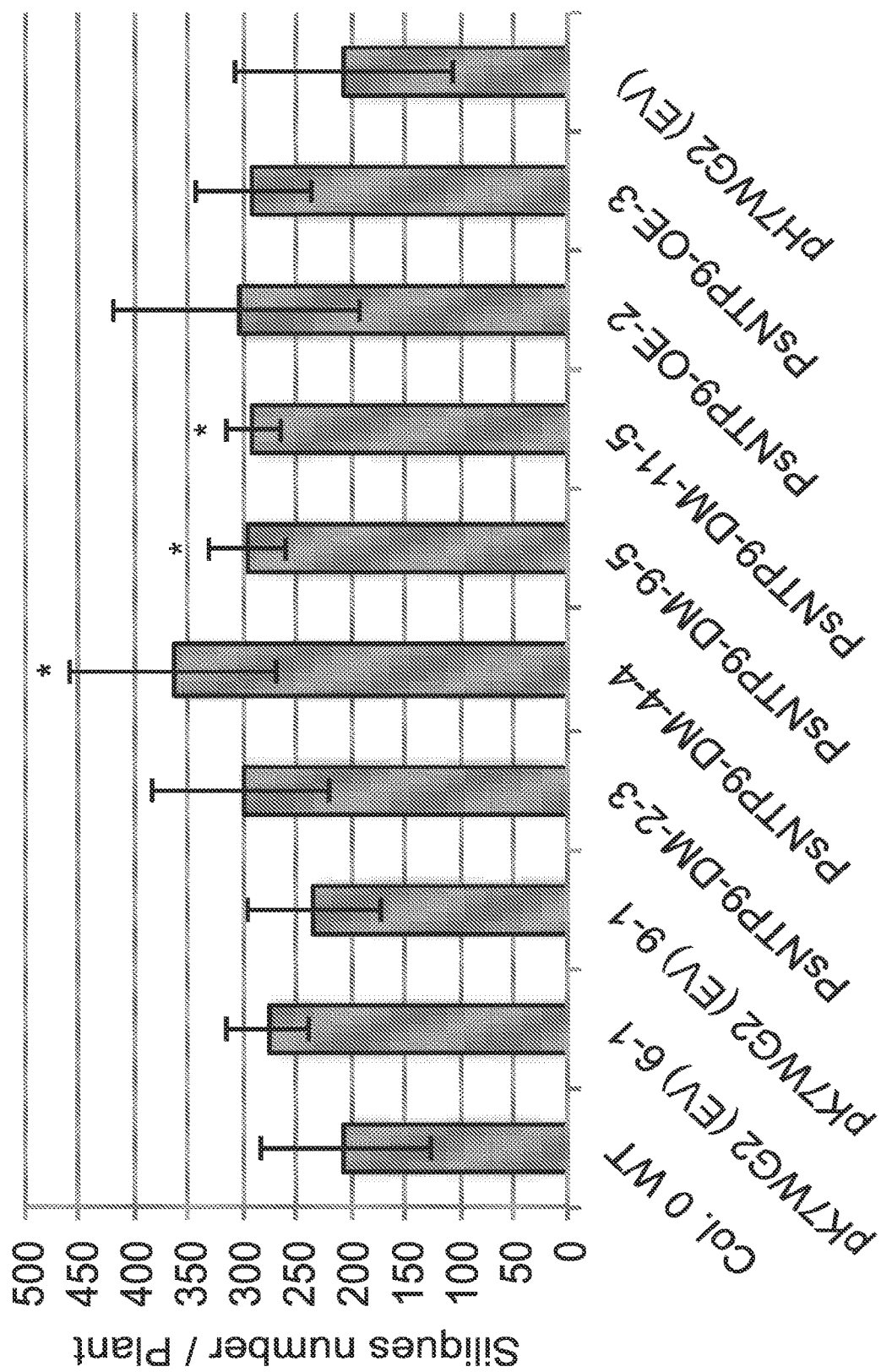
FIG. 17 is a bar chart showing the silique number produced by mature *Arabidopsis* plants transformed with modified pea apyrase psNTP9 (psNTP9-DM2, psNTP9-DM4, psNTP9-DM9 and psNTP9-DM11), psNTP9 (OE-2 and OE-3=moderately expressing lines), Col-0 wild-type (WT) and empty vector (EV) controls. Error bars represent standard deviation and asterisks above the bars indicate mean values that are statistically significantly different from one another (Student's t-test, * P≤0.05; n=5).

FIG. 17 is a bar chart showing the silique number produced by mature *Arabidopsis* plants. Silique number produced by mature *Arabidopsis* plants is statistically significantly higher in transgenic lines transformed with modified pea apyrase psNTP9 (psNTP9-DM4, psNTP9-DM9 and psNTP9-DM11) compared to Col-0 wild-type (WT), empty vector (EV) control and transgenic lines transformed with psNTP9 (OE-2 and OE-3=moderately expressing lines) plants.

Figure 18:
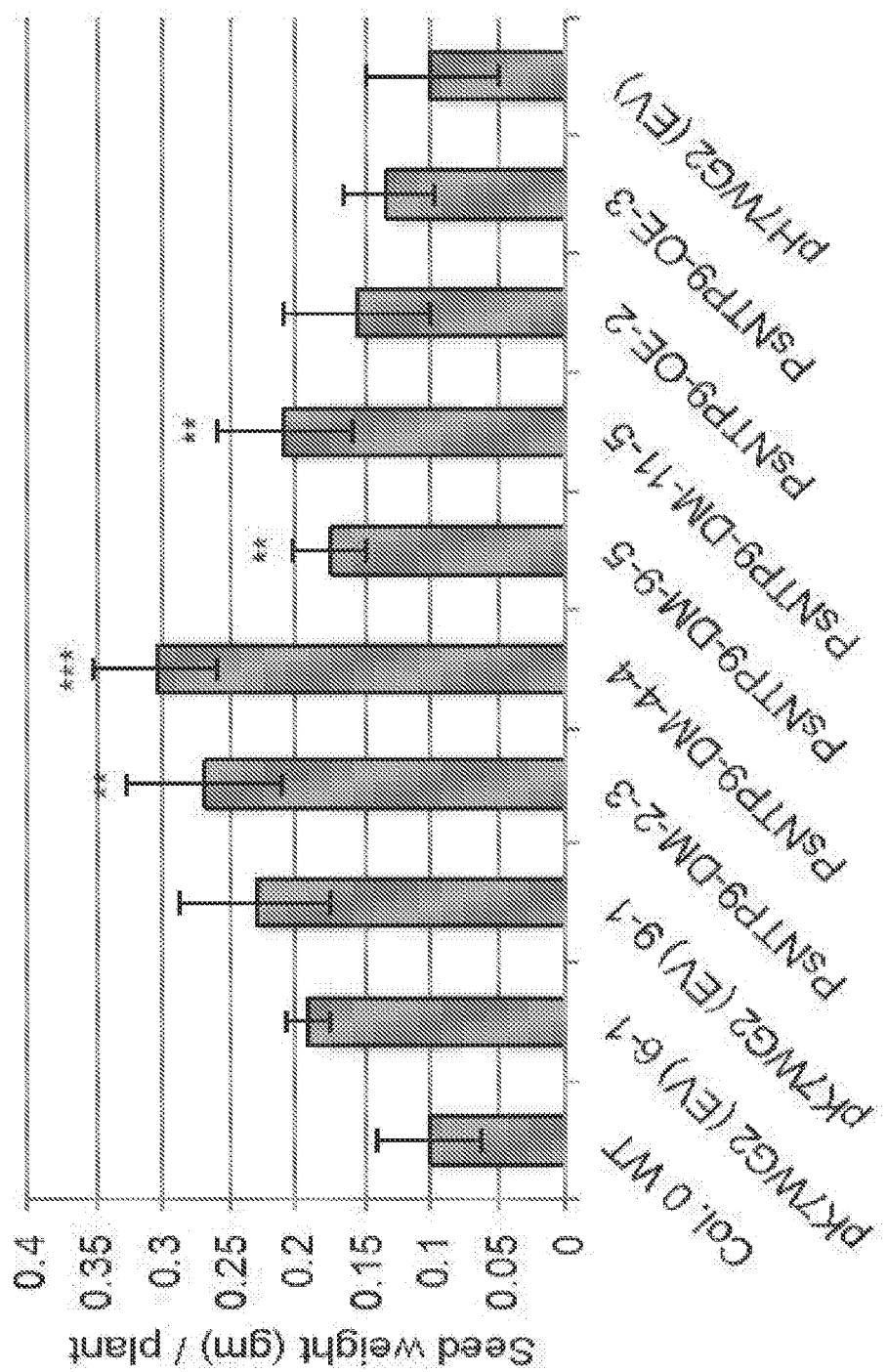
FIG. 18 is a bar chart showing average seed weight in grams (gm)/plant produced by mature *Arabidopsis* plants transformed with modified pea apyrase psNTP9 (psNTP9-DM2, psNTP9-DM4, psNTP9-DM9 and psNTP9-DM11), psNTP9 (OE-2 and OE-3=moderately expressing lines), Col-0 wild-type (WT) and empty vector (EV) controls. Error bars represent standard deviation and asterisks above the bars indicate mean values that are statistically significantly different from one another (Student's t-test,  P≤0.01; * P≤0.001; n=5).

FIG. 18 is a bar chart showing average seed weight in grams (gm)/plant produced by mature *Arabidopsis* plants. Average seed weight/plant produced by mature *Arabidopsis* plants is statistically significantly higher in transgenic lines transformed with modified pea apyrase psNTP9 (psNTP9-DM2, psNTP9-DM4, psNTP9-DM9 and psNTP9-DM11) compared to Col-0 wild-type (WT), empty vector (EV) control and transgenic lines transformed with psNTP9 (OE-2 and OE-3=moderately expressing lines) plants.

Figure 19:
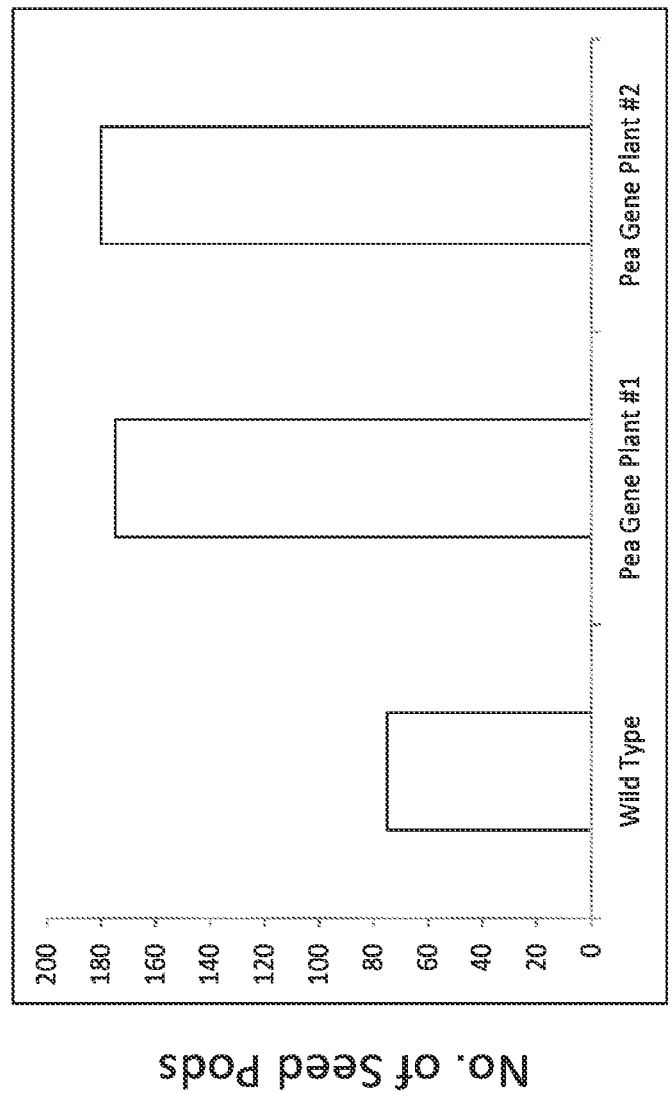
FIG. 19 is a bar chart showing the distribution of the total number of seed pods for the wild type plants and two soybean plants transformed with psNTP9.

FIG. 19 is a bar chart showing the distribution of the total number of seed pods for the wild type plants and two soybean plants transformed with psNTP9. The total number of seed pods is statistically significantly higher for both soybean plants transformed with psNTP9 compared to a wild-type control plant. Statistical significance was determined by chi square test based on equal distribution of seed pods. The actual length of three seed pods from soybean plants transformed with psNTP9 (2.3 inches, 2.1 inches and 2.1 inches) are larger compared to seed pods from three wild-type control plants (1.6 inches, 1.3 inches and 1.3 inches).

Figure 20:
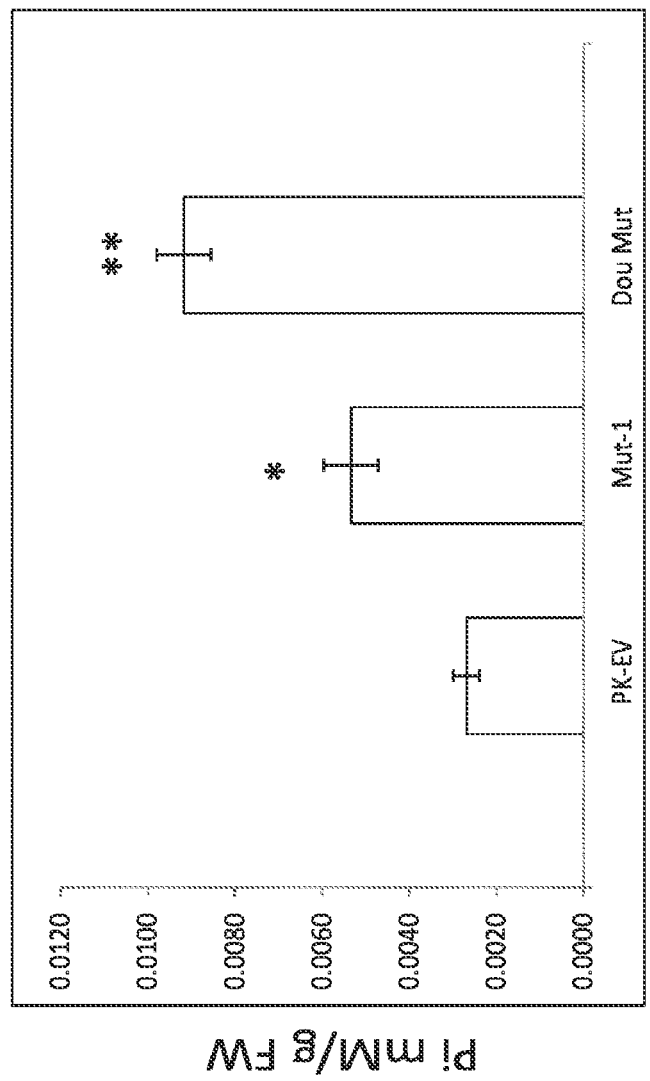
FIG. 20 is a bar chart showing the phosphate uptake for soybean hairy root cultures transformed with pea psNTP9 with a single (Mut-1) and double mutations (Dou Mut) compared to soybean culture transformed with an empty vector control (PK-EV). Error bars represent standard error and asterisks above the bars indicate mean values that are statistically significantly different from one another (Student's t-test **=P≤0.00001; *=P≤0.01; n≥5).

FIG. 20 is a bar chart showing the phosphate uptake for soybean hairy root cultures transformed with pea psNTP9 with a single (Mut-1) and double mutations (Dou Mut) compared to soybean culture transformed with an empty vector control (PK-EV). Phosphate uptake is statistically significantly increased in soybean hairy root cultures transformed with pea psNTP9 with a single mutation (Mut-1) and pea psNTP9 with a double mutation (Dou Mut) compared to empty vector control (PK-EV).

Soybeans produced from psNTP9 (soybean transgenic (for psNTP9) Line 16C and Line 14A) are considerably larger than those produced from wild-type soybeans (Williams-82). Comparison of the seed weight (seeds/g) also shows that soybeans produced from psNTP9 (soybean transgenic (for psNTP9) Line 16C (4.52 seeds/gram) and Line 14A (4.71 seeds/gram)) are considerably larger than those from wild-type soybeans (Williams-82; 9.09 seeds/gram (grown at Welch Greenhouse); 6.01 seeds/gram (from Missouri); and 5.97 seeds/gram (from ISU)). The standard seed number for Williams-82 is 5.85 seeds/gram.

Transgenic soybean plants from psNTP9 (soybean transgenic (for psNTP9)) are much larger and have many more branches, leaves and seed pods than control plants from wild-type soybeans (Williams-82).

The psNTP9 amino acid sequence is provided as SEQ ID NO:1, and a modified psNTP9 amino sequence is provided as SEQ ID NO:2. A comparison of SEQ ID NOs:1 and 2 show that the sequences are different in two amino acid positions: Amino acid 208 is serine in SEQ ID NO:1 and leucine in SEQ ID NO:2, and amino acid 216 is proline in SEQ ID NO:1 and arginine in SEQ ID NO:2. The psNTP9 DNA sequence is provided as SEQ ID NO:3, and the modified psNPT9 DNA sequence is provided as SEQ ID NO:4. A comparison of SEQ ID NOs:3 and 4 show that the sequences are different in two nucleotide positions: Nucleotide 623 is cytosine in SEQ ID NO:3 and thymine in SEQ ID NO:4, and nucleotide 647 is cytosine in SEQ ID NO:3 and guanine in SEQ ID NO:4.

Ectopic expression of the natural version and modified versions of the pea apyrase, psNTP9, improves growth and yield in plants in a variety of plant species. The present disclosure includes increased root growth and leaf size as well as increased silique number and seed yield of mature plants at different levels of nutrients. One aspect of the disclosure is that plants expressing the pea apyrase psNTP9, or modified versions of psNTP9, show increased phosphate uptake.

Phosphate uptake is increased in both cotton and soybean hairy root cultures ectopically expressing psNTP9 compared to control transformed with empty vector as measured by total inorganic phosphate content per equal weight of tissue. Primary roots grow longer in 3-week old seedlings grown in the absence of phosphate fertilizer for both Col-0 and WS ecotypes of Arabidopsis thaliana in lines ectopically expressing psNTP9 compared to wild-type controls. Leaf area is increased in 3-week old seedlings grown in the absence of phosphate fertilizer for both Col-0 and WS ecotypes of *A. thaliana* in lines ectopically expressing psNTP9 compared to wild-type controls. There are more siliques produced *A. thaliana* (ecotype Col-0) plants ectopically expressing psNTP9 grown in half and full-fertilizer conditions compared to wild-type controls.

There are more seeds as judged by total seed weight produced by *A. thaliana* (ecotype Col-0) plants ectopically expressing psNTP9 grown in half and full-fertilizer conditions compared to wild-type controls. There are more seed pods produced by soybean plants ectopically expressing psNTP9 grown in full-fertilizer conditions compared to wild-type controls. There are larger seed pods produced by soybean plants ectopically expressing psNTP9 grown in full-fertilizer conditions compared to wild-type controls. Phosphate uptake was increased in soybean hairy root cultures ectopically expressing modified versions of psNTP9 compared to control transformed with empty vector as measured by total phosphate content per equal weight of tissue.

Example 2

In another study, expression of the pea apyrase gene psNTP9 conferred improved drought tolerance in transgenic *A. thaliana* compared to wild-type and empty vector plants.

Protocol: Wild-type (Col-0) and transgenic seeds of *A. thaliana* were sterilized and sowed on ½ MS media. The transgenic seeds were taken from the same lines used in the *Arabidopsis* yield assays. The lines were: EV-1=Empty Vector control line; Col-0=wild-type control line; HE-1, HE-2, HE-3=High Expresser lines ectopically expressing psNTP9; ME-1=Moderate Expresser line ectopically expressing psNTP9.

Seeds were planted and grown in soil to obtain seedlings after 10 days. For drought stress, 10-day-old *Arabidopsis* plants were subjected to drought stress (withheld water) conditions for 21 days. The well-watered plants were treated as control. Eight pots containing 5 plants of each line (40 plants) were used in each biological repeat. The drought treated plants were re-watered after 21 days of drought stress treatment. The survival rates of drought stressed plants were recorded after re-watering for 2 days later. Survival rates were calculated by counting the number of green, healthy plants. The aerial parts of the drought stress treated plants after re-watering for 2 days were weighed and recorded along with the control plants (well-watered plants). To measure water content, the aerial parts of the soil-grown plants were detached and weighed immediately (0 minutes). Thereafter, the plants were allowed to dry naturally under ambient conditions (at room temperature and humidity). Fresh weight of each plant was measured at indicated time points (15, 30, 45, 60, 120, 180 and 240 minutes). Water content was calculated as the percentage of the fresh weight at each indicated time point. To measure relative water loss content, the aerial parts of the soil-grown plants were detached and weighed immediately (0 minutes). Thereafter, the plants were allowed to dry naturally under ambient conditions (at room temperature and humidity). Fresh weight of each plant was measured at indicated time points (15, 30, 45, 60, 120, 180 and 240 minutes). Relative water loss rate was expressed as percent change in the fresh weight (FW) at each indicated time point (Cha et al., 2015; Shi et al., 2015).

When exposed to drought stress for 21 days, the transgenic *Arabidopsis* plants with over-expressed psNTP9 are able to flower and are larger, more verdant with more branches and leaves, and produced healthier siliques compared to the wild-type and empty vector control *Arabidopsis* plants. The survival rates for the transgenic plants (HE-1 84.17% (101/120); HE-2 87.5% (105/120); HE-3 81.67% (98/120); ME-1 85.83% (103/120)) are much higher than the wild-type (37.5% (45/120)) and empty vector (32.5% (39/120)) control plants. As demonstrated in the induced-drought study, transgenic *A. thaliana* plants ectopically expressing psNTP9 had improved drought tolerance compared to wild-type and empty vector control *Arabidopsis* plants.

Figure 21:
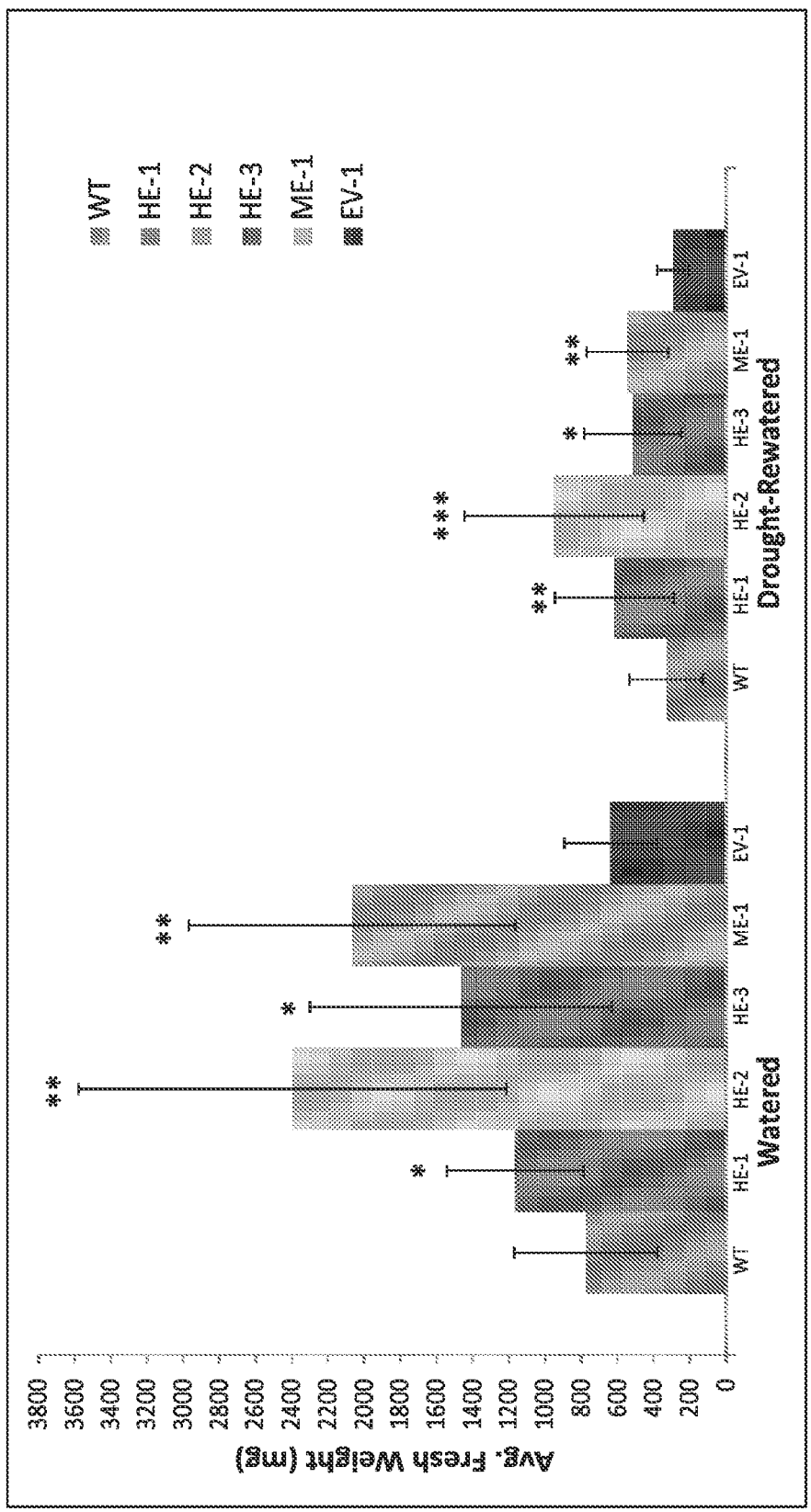
FIG. 21 is a bar chart showing average fresh weight of the aerial parts of well-watered and drought re-watered (2 days after re-watering) wild-type (WT), transgenic (HE-1, HE-2, HE-3 and ME-1) and empty vector (EV-1) *Arabidopsis* plants. Each bar represents means of three biological replicates. Error bars represent standard deviation and asterisks above the bars indicate mean values that are statistically significantly different from one another (Student's t-test, *=P≤0.05; =P≤0.005; *=P≤0.0005; n>10 for watered plants; n>20 for drought re-watered plants).

FIG. 21 is a bar chart showing average fresh weight of the aerial parts of well-watered and drought re-watered (2 days after re-watering) *Arabidopsis* plants. Fresh weight of aerial parts are statistically significantly higher in lines transformed with psNTP9 (HE=highly expressing lines; ME=moderately expressing lines) compared to Col-0 wild-type control (WT) and empty vector control (EV) plants when well-watered and following drought stress treatment 2 days after re-watering.

Figure 22:
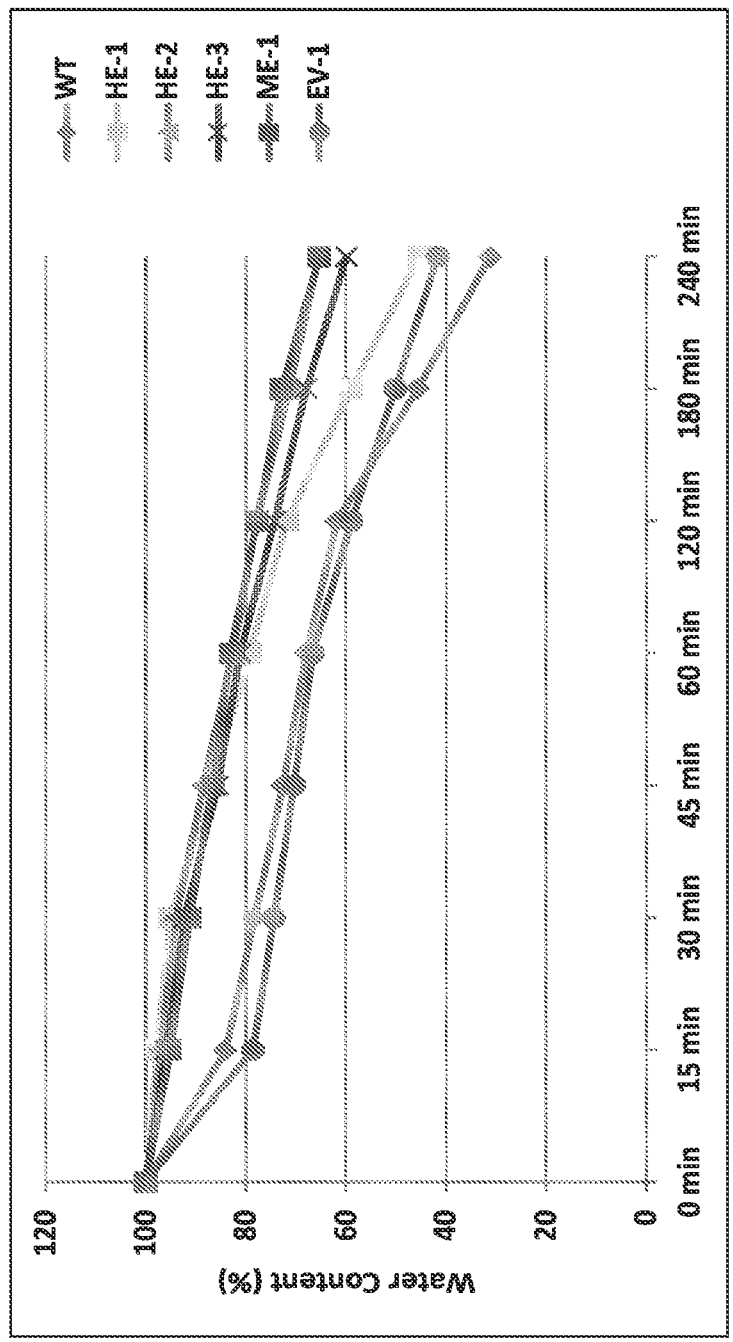
FIG. 22 is a graph showing water content (%) over time of Col-0 wild-type (WT), empty vector control (EV) and transgenic lines expressing psNTP9 (HE=highly expressing lines; ME=moderately expressing lines) *Arabidopsis* plants. The values represent means of three biological replicates (n>9).
Figure 23:
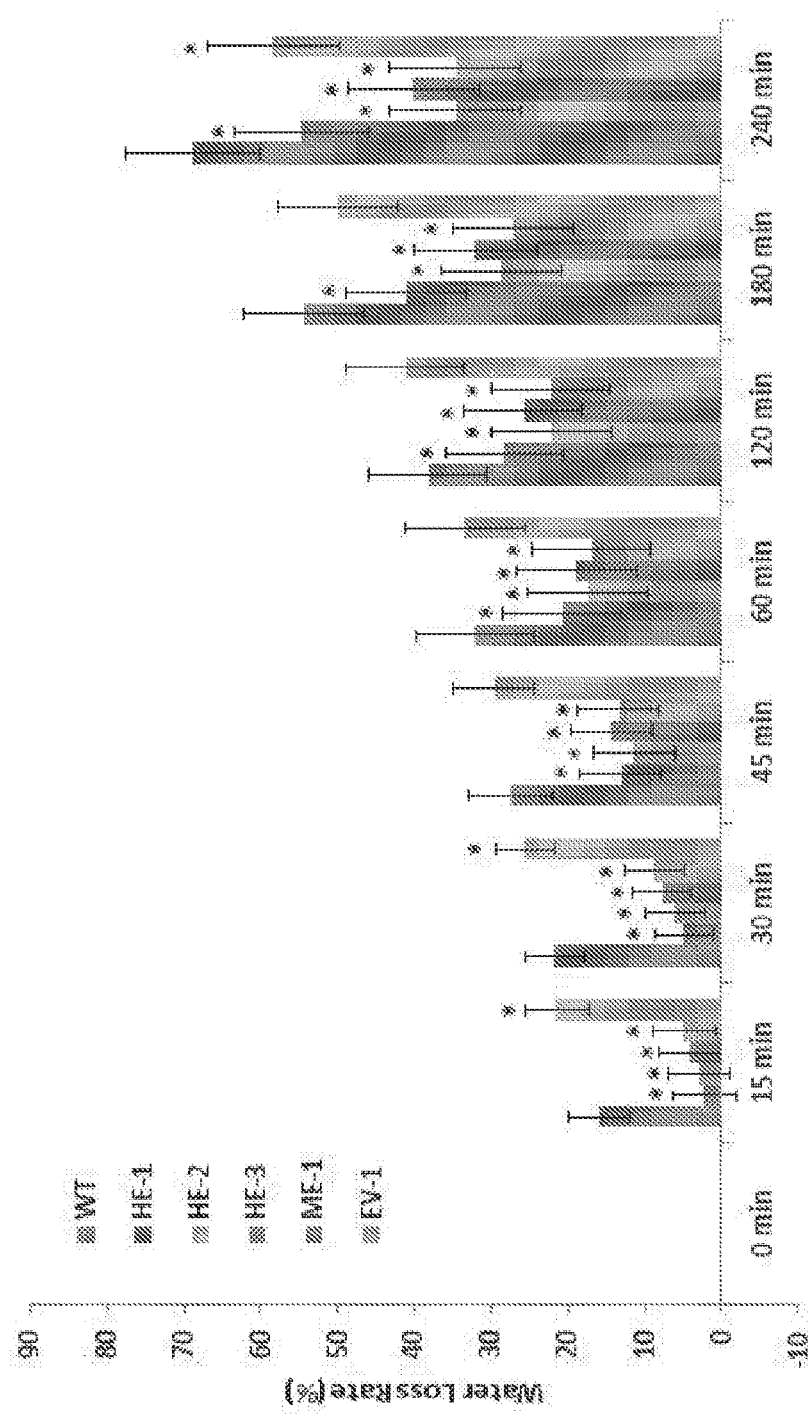
FIG. 23 is a bar graph showing relative water loss rate (%) of *Arabidopsis* plants that include Col-0 wild-type (WT), empty vector control (EV) and transgenic lines expressing psNTP9 (HE=highly expressing lines; ME=moderately expressing lines). Each bar represents means of three biological replicates. Error bars represent standard deviation and asterisks above the bars indicate mean values that are statistically significantly different from one another (Student's t-test, * P≤0.0005; n>9). The lanes from left to right for each time period correspond to WT, HE-1, HE-2, HE-3, ME-1 and EV-1, respectively.

FIG. 22 is a graph showing water content (%) over time of Col-0 wild-type (WT), empty vector control (EV) and transgenic lines expressing psNTP9 (HE=highly expressing lines; ME=moderately expressing lines) *Arabidopsis* plants. The transgenic lines show higher water content compared to the WT and EV control lines. FIG. 23 is a bar graph showing relative water loss rate (%) of *Arabidopsis* plants that include Col-0 wild-type (WT), empty vector control (EV) and transgenic lines expressing psNTP9 (HE=highly expressing lines; ME=moderately expressing lines). The transgenic lines show statistically significantly decreased water loss compared to the wild-type control plants.

In another drought stress study, 4-week-old *Arabidopsis* plants (wild-type plants, Col-0 and Col-0 plants ectopically expressing psNTP9) were subjected to drought stress (withheld water) conditions for 21 days. The well-watered plants were treated as control. Thirty-five plants of each line were used. The drought treated plants were re-watered after 21 days of drought stress treatment. The survival rates of drought stressed plants were recorded after re-watering for 2 days. Survival rates were calculated by counting the number of green, healthy plants. The aerial parts of the drought stress treated plants after re-watering for 2 days were weighed and recorded along with the control plants (well-watered plants) (Cha et al., 2015; Shi et al., 2015).

Figure 24:
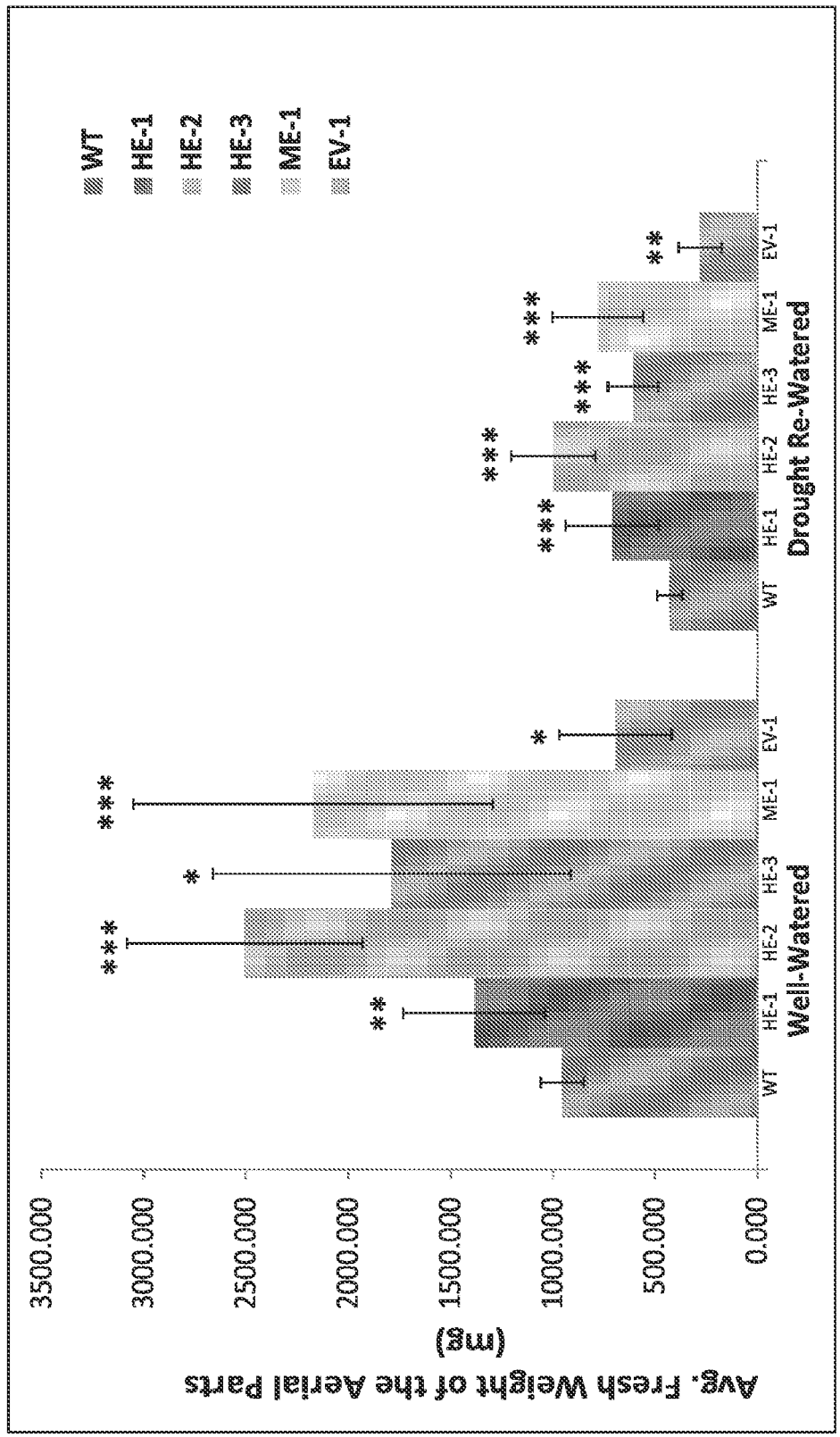
FIG. 24 is a bar chart showing fresh weight of the aerial parts of well-watered plants and the drought re-watered *Arabidopsis* plants that include Col-0 wild-type (WT), empty vector control (EV) and transgenic lines expressing psNTP9 (HE=highly expressing lines; ME=moderately expressing lines) after 51 days. Each bar represents means of three biological replicates. Error bars represent standard deviation and asterisks above the bars indicate mean values that are statistically significantly different from one another (Student's t-test, *=P≤0.05; =P≤0.005; *=P≤0.0005; n=10 for watered plants; n>8 for drought re-watered plants).

The survival rates for the transgenic plants (HE-1 74.28% (26/35); HE-2 82.85% (29/35); HE-3 68.57% (24/35); ME-1 77.14% (27/35)) are much higher than the wild-type (31.43 (11/35)) and empty vector 22.85 (8/35)) control plants. FIG. 24 is a bar chart showing fresh weight of the aerial parts of well-watered plants and the drought re-watered *Arabidopsis* plants (after 51 days). Fresh weight of aerial parts are statistically significantly higher in lines transformed with psNTP9 (HE=highly expressing lines; ME=moderately expressing lines) compared to Col-0 wild-type control (WT) and empty vector control (EV) plants when well-watered and when drought stress treated followed by 2 days re-watering.

Another study was performed to analyze the behavior of transgenic soybean plants under drought conditions. Wild-type plants and T3 plants from each transgenic line ectopically expressing psNTP9 (14A, 16C and 17B) were grown in 2-L plastic pots for 26 days (V3 Stage-Vegetative Stage, Three trifoliate stages) in the Growth Chamber (controlled conditions). Prior to the initiation of stress, the plants were saturated with water and then irrigation was stopped. Plants were assessed for tolerance to water deficit stress by withholding irrigation for 8 days (depending on the conditions). Plants were monitored daily for wilting. Recovery after water stress was assessed after 3 days of re-watering.

Phenotypic analysis of wild-type (Williams 82) soybean plants after 8 days of drought showed 2/14 plants with symptoms of wilting, 6/14 completely dried and 6/14 dried/semi-dried. Phenotypic analysis of Williams 82 soybean transgenic plants expressing psNTP9 (Line 14A) after 8 days of drought showed 5/16 plants with symptoms of wilting, 2/16 completely dried and 9/16 dried/semi-dried. Phenotypic analysis of Williams 82 soybean transgenic plants expressing psNTP9 (Line 16C) after 8 days of drought showed 6/16 plants with symptoms of wilting, 5/16 completely dried and 5/16 dried/semi-dried. Phenotypic analysis of Williams 82 soybean transgenic plants expressing psNTP9 (Line 17B) after 8 days of drought showed 3/13 plants with symptoms of wilting, 2/13 completely dried and 8/13 dried/semi-dried. Line 14A, 16C and 17B plants all showed improved drought resistance compared to wild-type control plants.

Survival rates for wild-type (Williams 82) soybean plants after 8 days of drought followed by 3 days of re-watering was 50%. Survival rates for Williams 82 soybean transgenic plants expressing psNTP (Line 14A, 16C and 17B) after 8 days of drought followed by 3 days of re-watering were 93.75%, 81.25% and 84.61%, respectively, compared to 50% for wild-type control plants. Surviving transgenic plants were bigger with more leaves than surviving wild-type control plants.

Example 3

In another study, it was demonstrated that expression of pea apyrase gene (psNTP9) conferred improved stress tolerance to *A. thaliana* plants as determined by the growth of primary and lateral roots. *Arabidopsis* plants over-expressing psNTP9 grew longer primary roots and had more lateral roots than the controls and moderately expressing lines in ½ MS+200 mM mannitol (osmotic medium).

Wild-type (WT) and transgenic seeds of *A. thaliana* were sterilized and sowed on ½ MS. The transgenic seeds were taken from the same lines used in the *Arabidopsis* yield assays. The lines were: EV-1 and EV-2=Empty Vector control lines; WT=wild-type control line; OE-1, OE-2 and OE-3=Over Expresser Lines (also referred to as HE-1, HE-2, HE-3=High Expresser lines); ME-1, ME-2, ME-3 and ME-4=Moderate Expresser Lines ectopically expressing psNTP9.

The plates were held at 4° C. for 3 days before transferring to the growth chamber. The 4-day old seedlings were transferred and vertically plated on ½ MS medium supplemented with 200 mM mannitol (osmotic medium). After 10 days of treatment, the samples were observed for the length of the primary root, number of lateral roots, root hair density and the length of the root hairs. Root hair density was determined as the number of root hairs in each of the five roots observed with a microscope (40×). Root hairs were counted 5 mm away from the root-tip. The length of the root hair was measured for each of the five roots. The length of the root hair was measured for 3 predominantly growing root hairs for each root (Ma et al., 2001).

Figure 25:
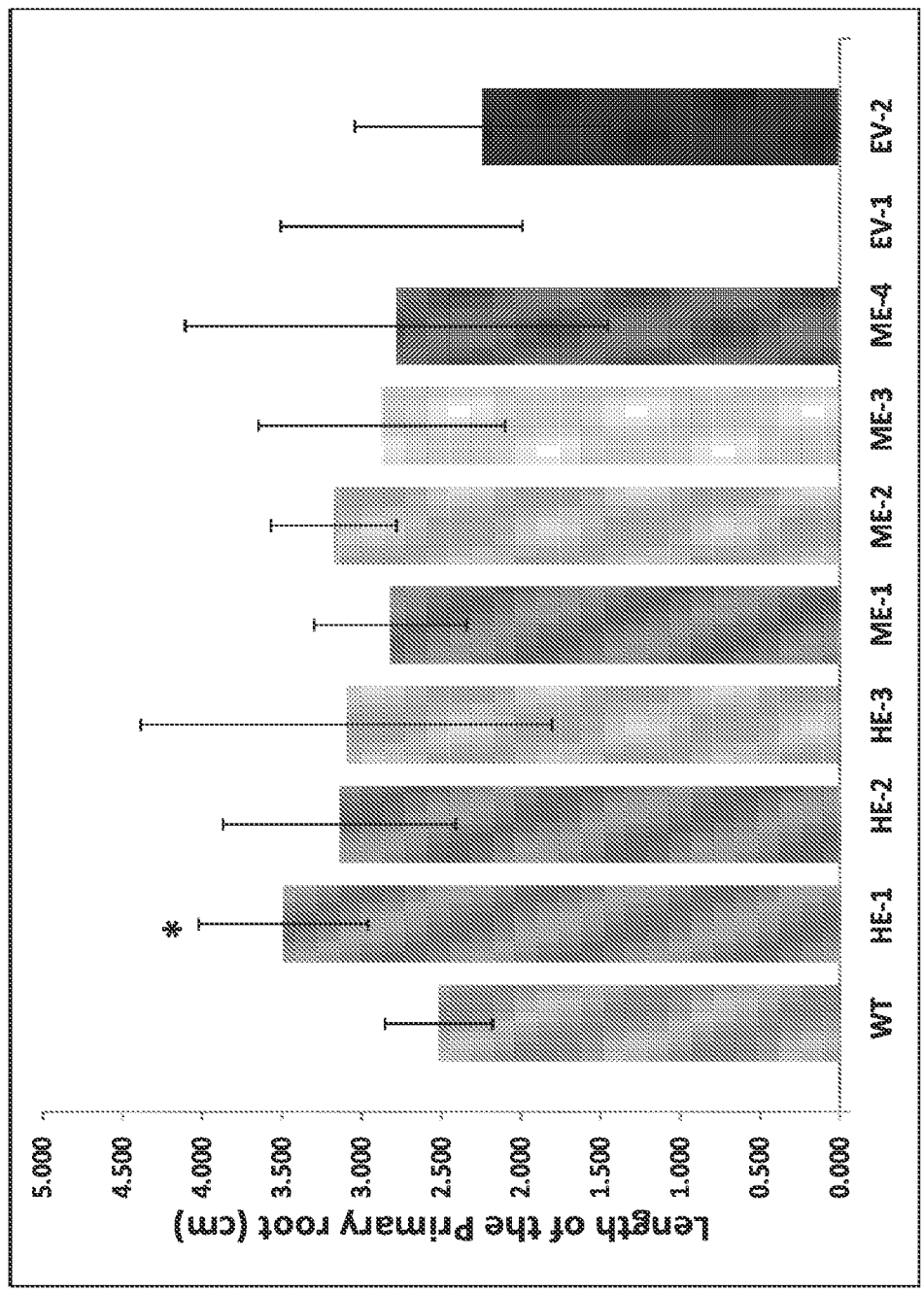
FIG. 25 is a bar chart showing average primary root length in centimeters for wild-type (control) and transgenic (OE, ME) and empty vector (EV) *Arabidopsis* seeds after 10 days growth on ½ MS with 200 mM mannitol (osmotic medium). OE refers to the over-expressing transgenic lines HE-1, HE-2 and HE-3. ME refers to the moderately expressing lines ME-1, ME-2, ME-3 and ME-4. EV refers to the empty vector lines EV-1 and EV-2. Error bars represent standard deviation and asterisks above the bars indicate mean values that are statistically significantly different from one another (Student's t-test, * P≤0.05, n=5).

The psNTP9 lines grew longer primary roots than the wild-type and empty vector control lines. FIG. 25 is a bar chart showing average primary root length in centimeters for the WT and transgenic seeds after 10 days growth on ½ MS+200 mM mannitol (osmotic medium). The primary root of HE-1 is statistically significantly longer than the ME, WT and the EV controls on the osmotic medium.

Figure 26:
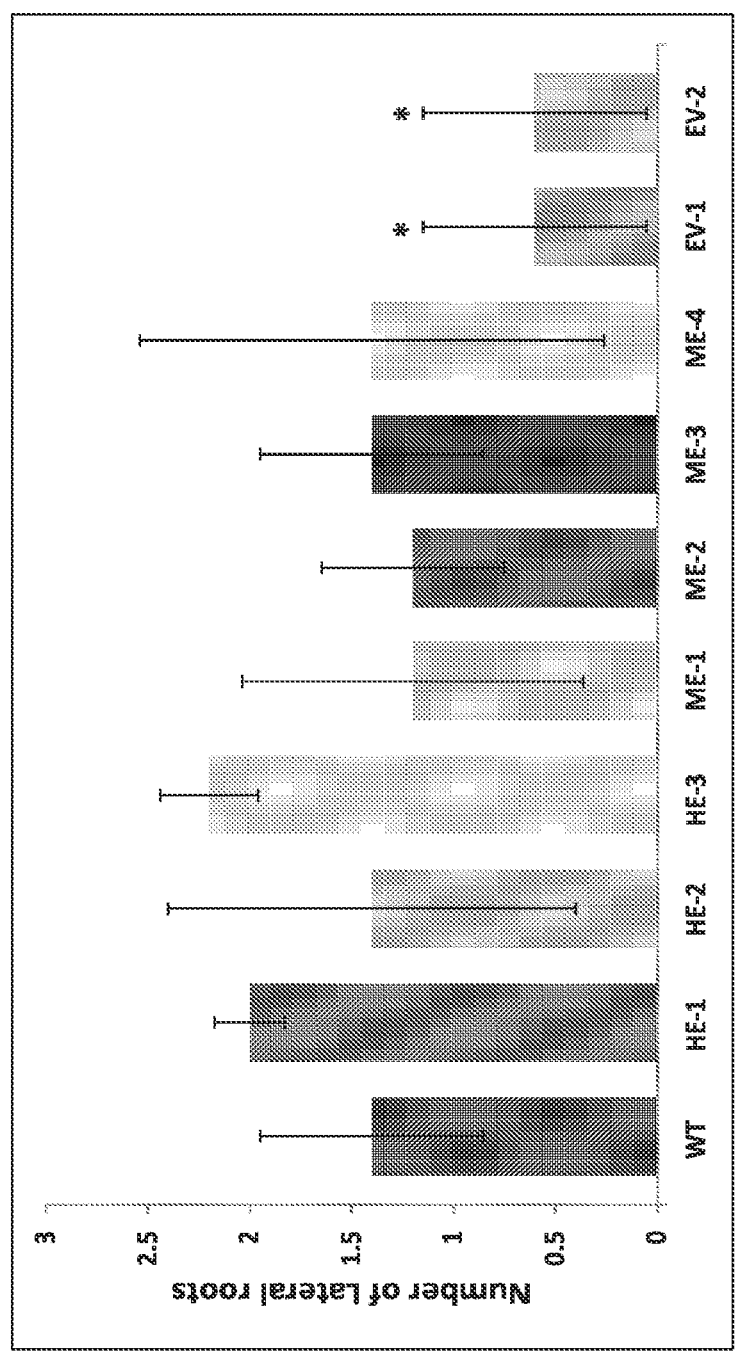
FIG. 26 is a bar chart showing average number of lateral roots observed for wild-type (control) and transgenic (OE and ME) and empty vector (EV) *Arabidopsis* seeds after 10 days growth on ½ MS with 200 mM mannitol (osmotic medium). Error bars represent standard deviation and asterisks above the bars indicate mean values that are statistically significantly different from one another (Student's t-test, * P≤0.05, n=5).

FIG. 26 is a bar chart showing average number of lateral roots observed for the WT and transgenic seeds after 10 days growth on ½ MS+200 mM mannitol (osmotic medium). The HE lines produced a greater number of lateral roots than the ME, WT and the EV controls on the osmotic medium.

Figure 27:
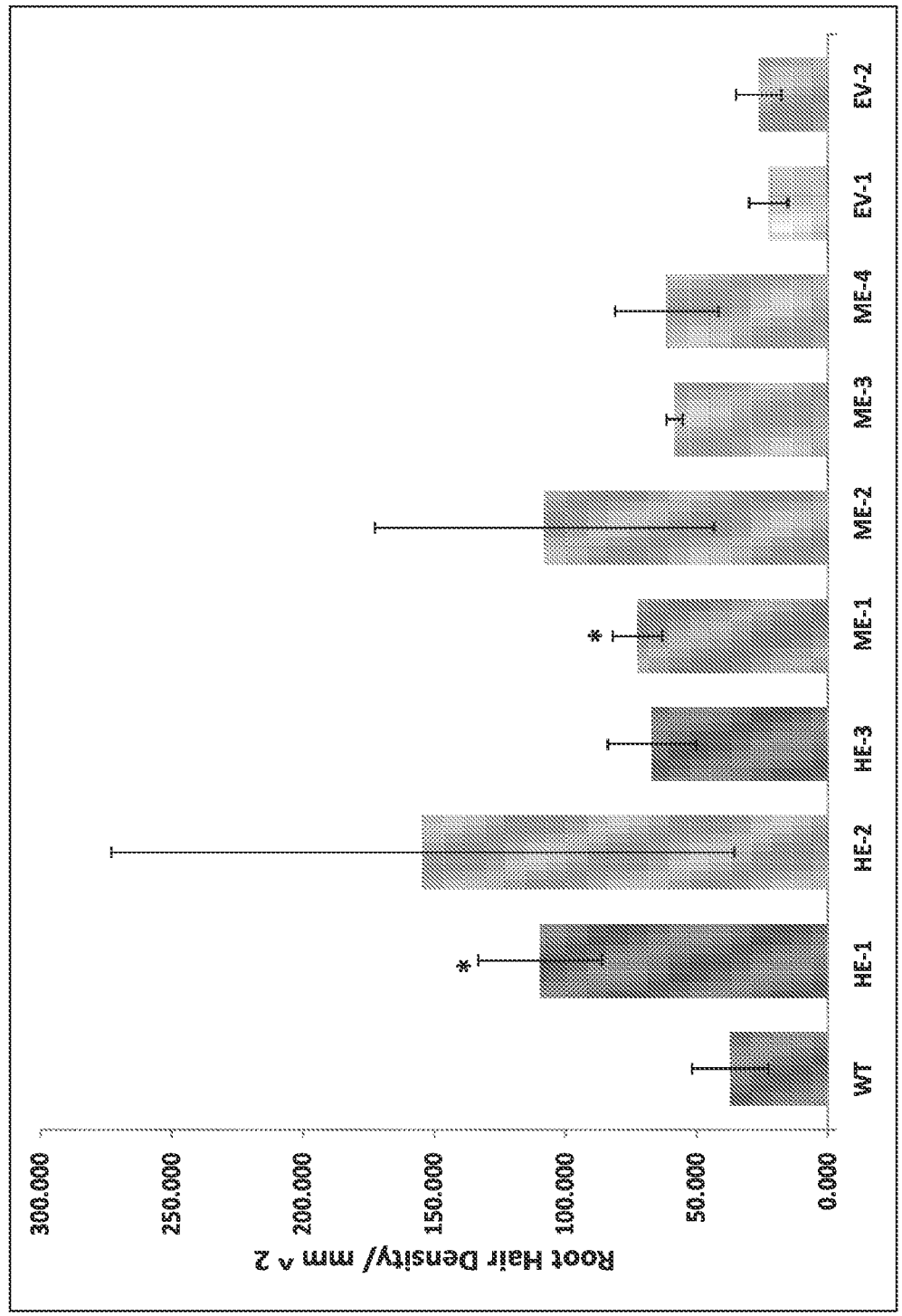
FIG. 27 is a bar chart showing root hair density for wild-type (WT), transgenic (HE-1, HE-2, HE-3, ME-1, ME-2, ME-3, and ME-4) and empty vector (EV-1 and EV-2) *Arabidopsis* plants after 10 days growth on ½ MS with 200 mM mannitol (osmotic medium). Error bars represent standard deviation and asterisks above the bars indicate mean values that are statistically significantly different from one another (Student's t-test, * P≤0.05, n=5).

FIG. 27 is a bar chart showing root hair density (number of root hairs/mm$^2$) for the WT and transgenic seeds after 10 days growth on ½ MS+200 mM mannitol (osmotic medium). The HE-1 and ME-1 lines had a statistically significant increase in root hair density compared to the WT and the EV controls on the osmotic medium.

Figure 28:
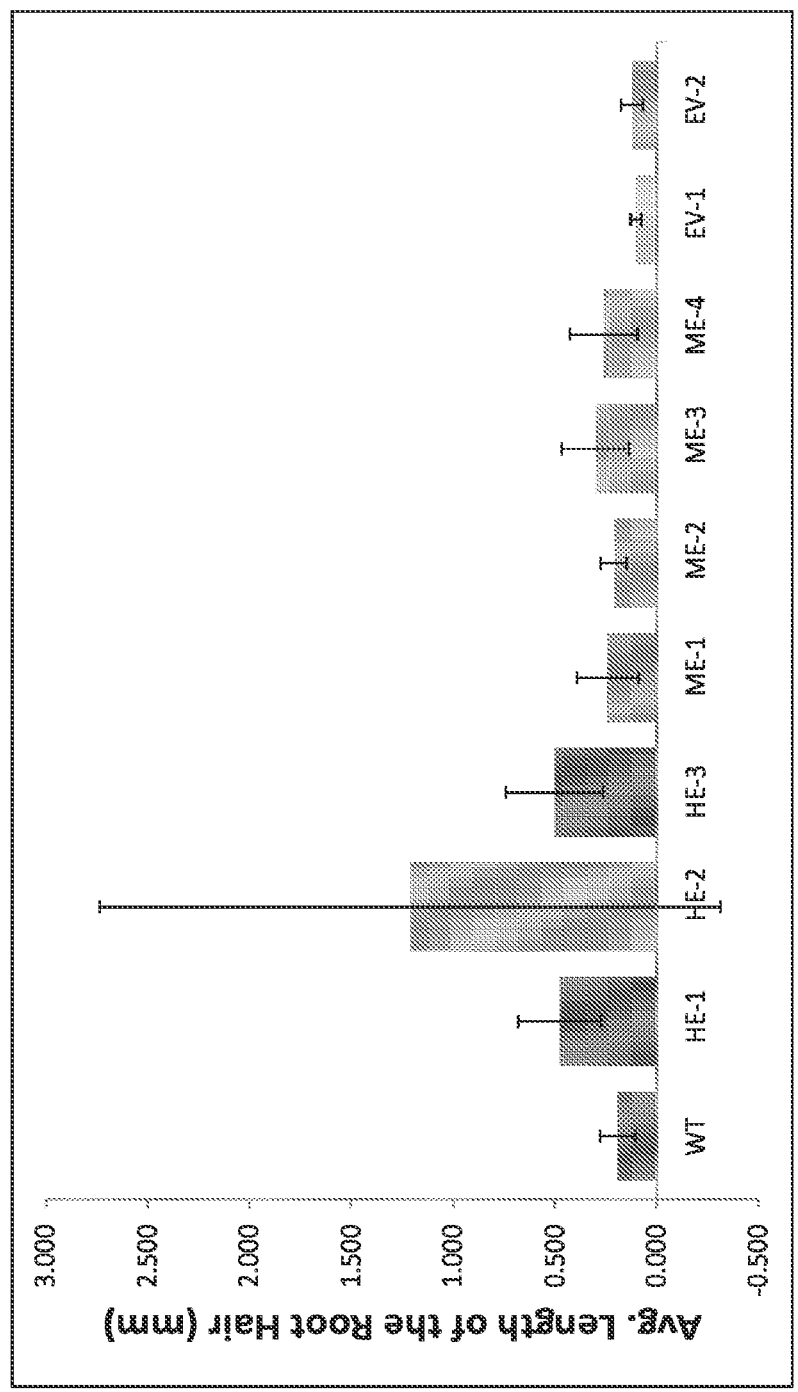
FIG. 28 is a bar chart showing average root hair length in millimeters observed for wild-type (WT), transgenic (HE-1, HE-2, HE-3, ME-1, ME-2, ME-3, and ME-4) and empty vector (EV-1 and EV-2) *Arabidopsis* plants after 10 days growth on ½ MS with 200 mM mannitol (osmotic medium). Error bars represent standard deviation and asterisks above the bars indicate mean values that are statistically significantly different from one another (Student's t-test, * P≤0.05, n=5).

FIG. 28 is a bar chart showing the length of the root hair in millimeters observed for the WT and transgenic seeds after 10 days growth on ½ MS+200 mM mannitol (osmotic medium). The HE lines had increased root hair length compared to the ME, WT and the EV controls on the osmotic medium.

Figure 29:
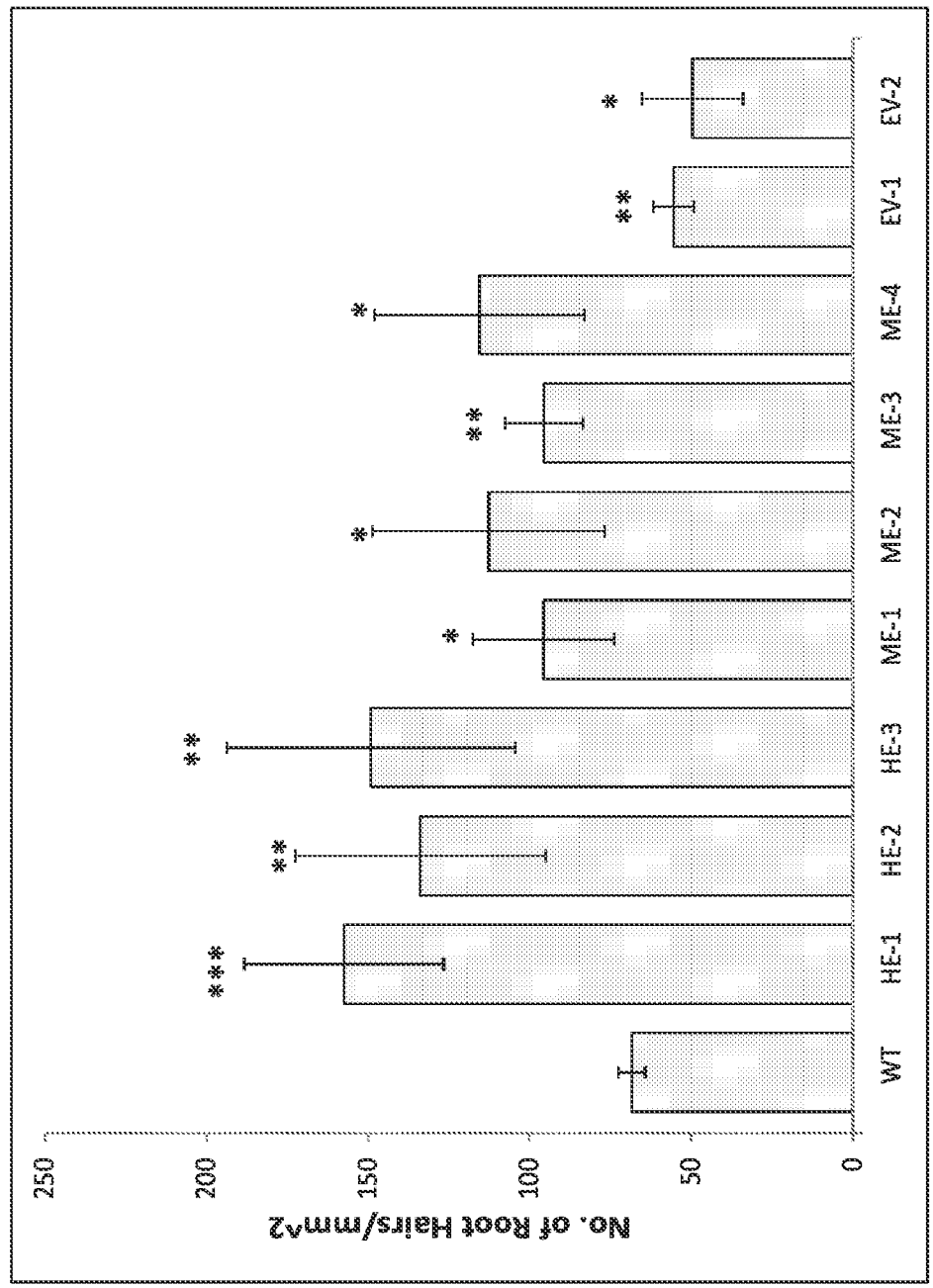
FIG. 29 is a bar graph showing root hair density (average number of root hairs/mm) in lines transformed with psNTP9 (HE=highly expressing lines; ME=moderately expressing lines), Col-0 wild-type control (WT) and empty vector control (EV) *Arabidopsis* plants. Error bars represent standard deviation and asterisks above the bars indicate mean values that are statistically significantly different from one another (Student's t-test, *=P≤0.05; =P≤0.005; *=P≤0.0005; n=5).
Figure 30:
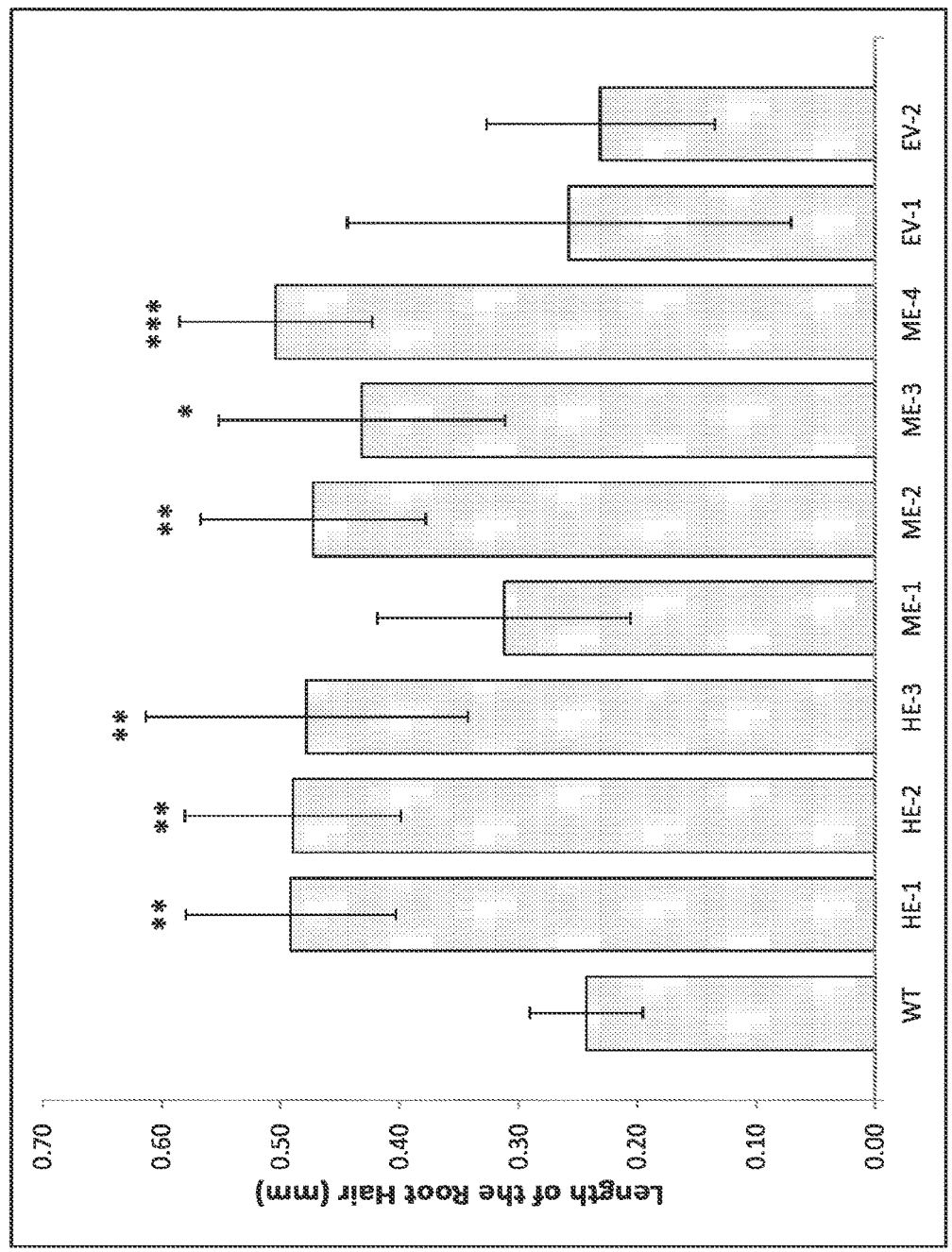
FIG. 30 is a bar graph showing root hair length (mm) in lines transformed with psNTP9 (HE=highly expressing lines; ME=moderately expressing lines), Col-0 wild-type control (WT) and empty vector control (EV) *Arabidopsis* plants. Error bars represent standard deviation and asterisks above the bars indicate mean values that are statistically significantly different from one another (Student's t-test, *=P≤0.05; =P≤0.005; *=P≤0.0005; n=5).

In addition there is an increase in the number and length of root hairs for the transgenic lines compared to the wild-type control. FIG. 29 is a bar graph showing root hair density (average number of root hairs/mm) for *Arabidopsis* plants. Root hair density is statistically significantly higher in lines transformed with psNTP9 (HE=highly expressing lines; ME=moderately expressing lines) compared to Col-0 wild-type control (WT) and empty vector control (EV) plants. FIG. 30 is a bar graph showing root hair length (mm) for *Arabidopsis* plants. Root hair length is statistically significantly longer in lines transformed with psNTP9 (HE=highly expressing lines; ME=moderately expressing lines) except for ME-1 compared to Col-0 wild-type control (WT) and empty vector control (EV) plants.

Example 4

Yield data, root architecture and root nodules were also studied in soybean. For yield data, soybean seeds were sown on soil germination mix and allowed to germinate. After 2 weeks of germination, the plants were transplanted into 5 gallon pots with the re-potting mix. The plants were watered daily. The plants were allowed to grow until full maturity (R8 Stage-Reproductive Stage). After the pods were completely matured, they were allowed to dry for 3-4 weeks within the plants. The pods were harvested and the seeds were collected to analyze the data for the average number of pods per plant, average number of seeds per plant, average seed weight per plant and to analyze the data for number of seeds per gram weight. For seed germination, 75% Sunshine® MVP Seedling and Propagation; 25% Profile® Field and Fairway™ calcined clay (0.2-0.5 cm granules) and Osmocote® 14-14-14: 28 ml/10 L of the soil mix. For mature soybean plants (re-potting), 75% Pro-Mix® Biofungicide and wetting agent; 25% Turface® MVP and Osmocote® 14-14-14: 28 ml/10 L of the soil mix. In addition to the Osmocote® in the soil mix, the plants are fertilized every month by adding approximately 10 ml of Osmocote® on the surface of the soil (by sprinkling on the top) for a 5 gallon pot.

Figure 31:
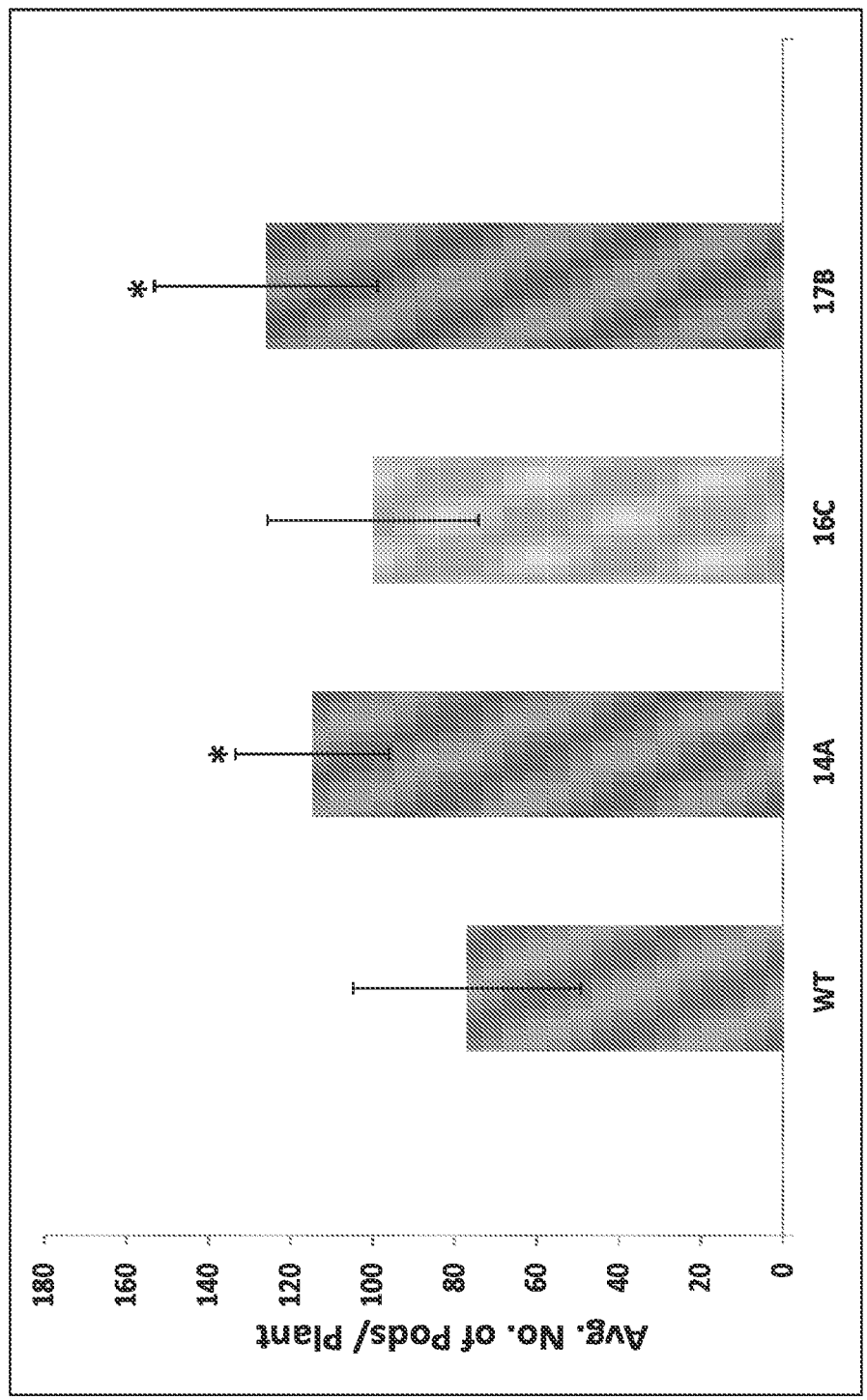
FIG. 31 is a bar chart showing average number of seed pods/plant for Williams 82 wild-type control soybean (WT) and T3 psNTP9 transgenic soybean (Line 14A, 17B and 16C) plants grown in a growth chamber. Error bars represent standard deviation and asterisks above the bars indicate mean values that are statistically significantly different from one another (Student's t-test, *=P≤0.05; n=6).
Figure 32:
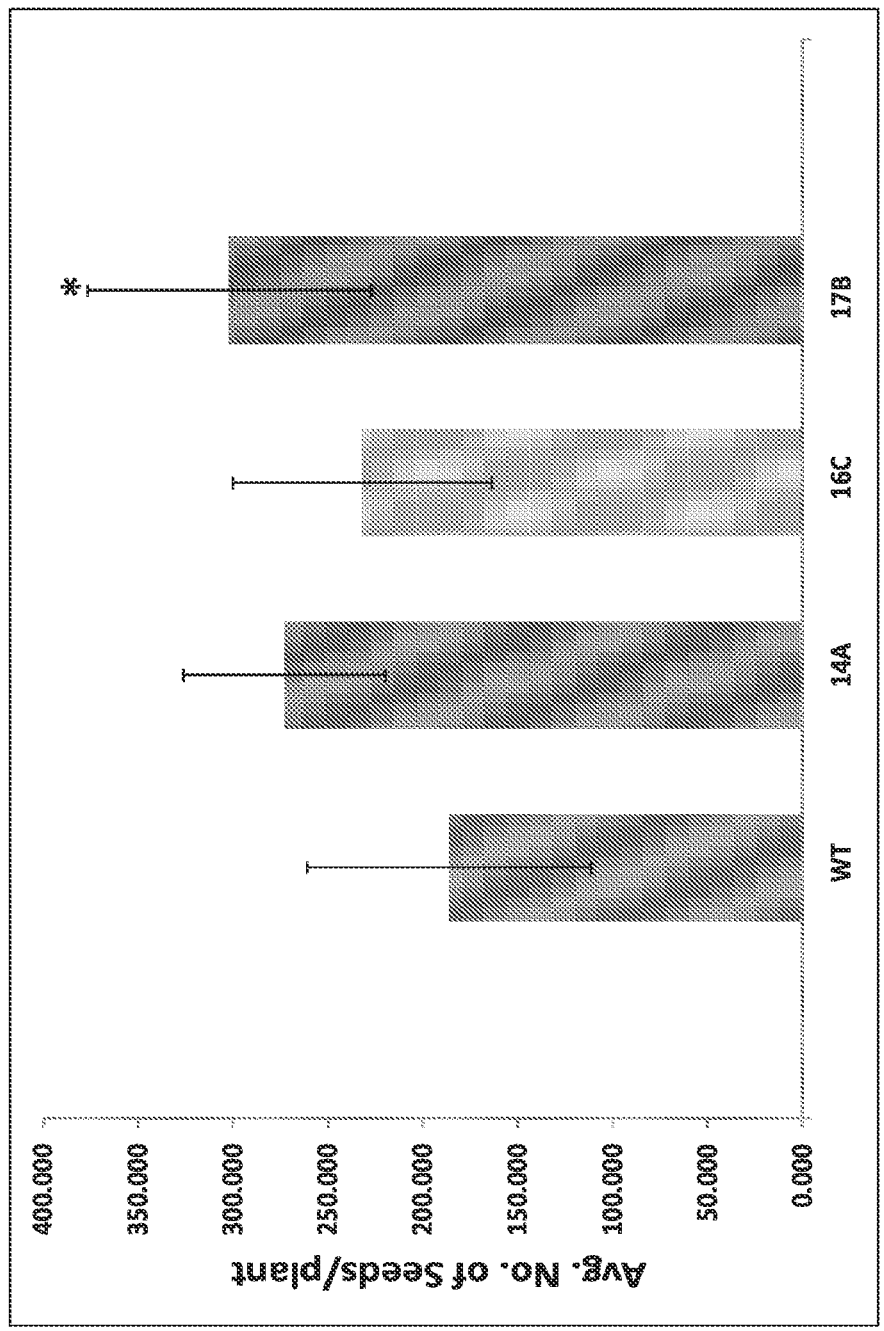
FIG. 32 is a bar chart showing average number of seeds/plant for Williams 82 wild-type control soybean (WT) and T3 psNTP9 transgenic soybean (Line 14A, 17B and 16C) plants grown in a growth chamber. Error bars represent standard deviation and asterisks above the bars indicate mean values that are statistically significantly different from one another (Student's t-test, *=P≤0.05; n=6).

FIG. 31 is a bar chart showing average number of seed pods/plant for Williams 82 wild-type control soybean (WT) and T3 psNTP9 transgenic soybean (Line 14A, 17B and 16C) plants grown in a growth chamber. The average number of seed pods/plant is statistically significantly higher in transgenic lines 14A and 17B compared to wild-type control. FIG. 32 is a bar chart showing average number of seeds/plant for Williams 82 wild-type control soybean (WT) and T3 psNTP9 transgenic soybean (Line 14A, 17B and 16C) plants grown in a growth chamber. The average number of seeds/plant is statistically significantly higher in transgenic line 17B compared to wild-type control.

Figure 33:
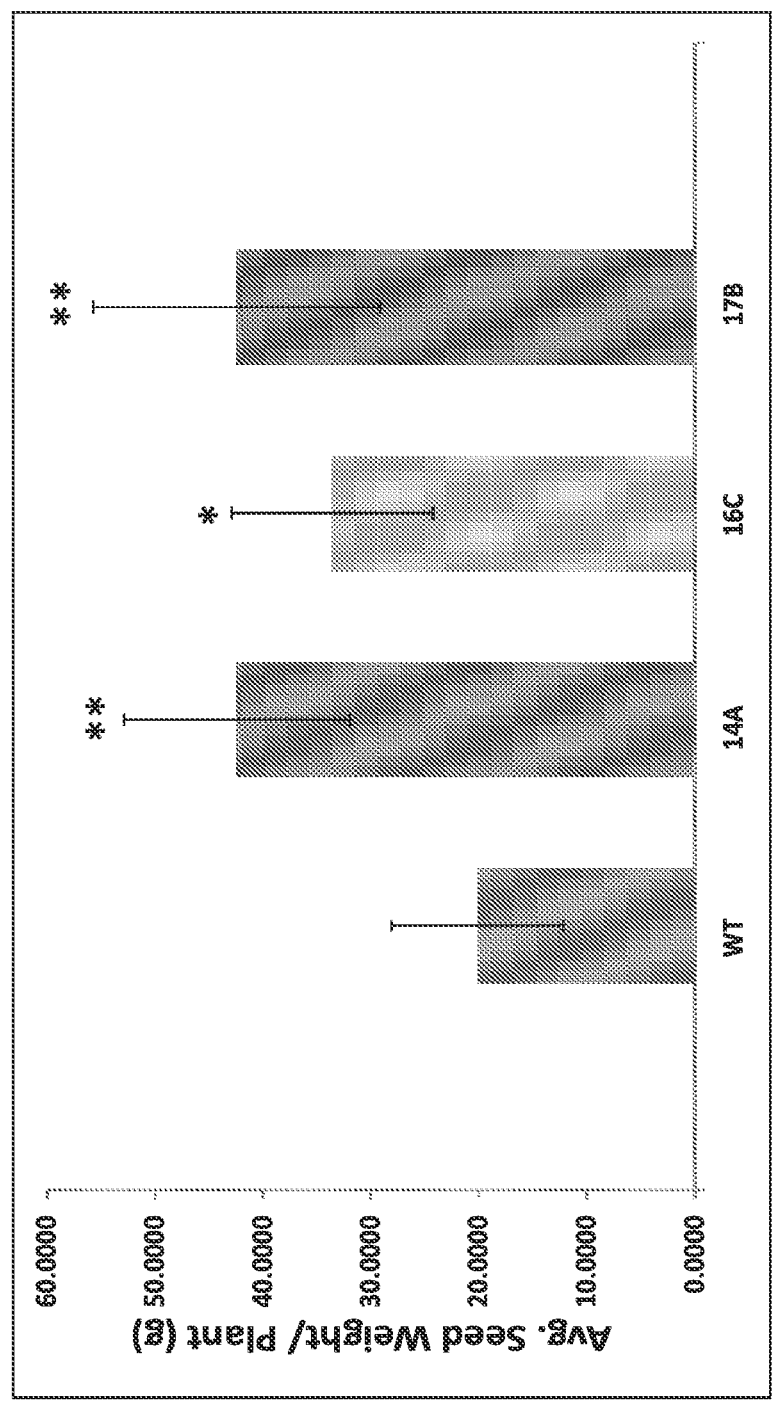
FIG. 33 is a bar chart showing average seed weight in grams (g)/plant for Williams 82 wild-type control soybean (WT) and T3 psNTP9 transgenic soybean (Line 14A, 17B and 16C) plants grown in a growth chamber. Error bars represent standard deviation and asterisks above the bars indicate mean values that are statistically significantly different from one another (Student's t-test, *=P≤0.05; **=P≤0.005; n=6).
Figure 34:
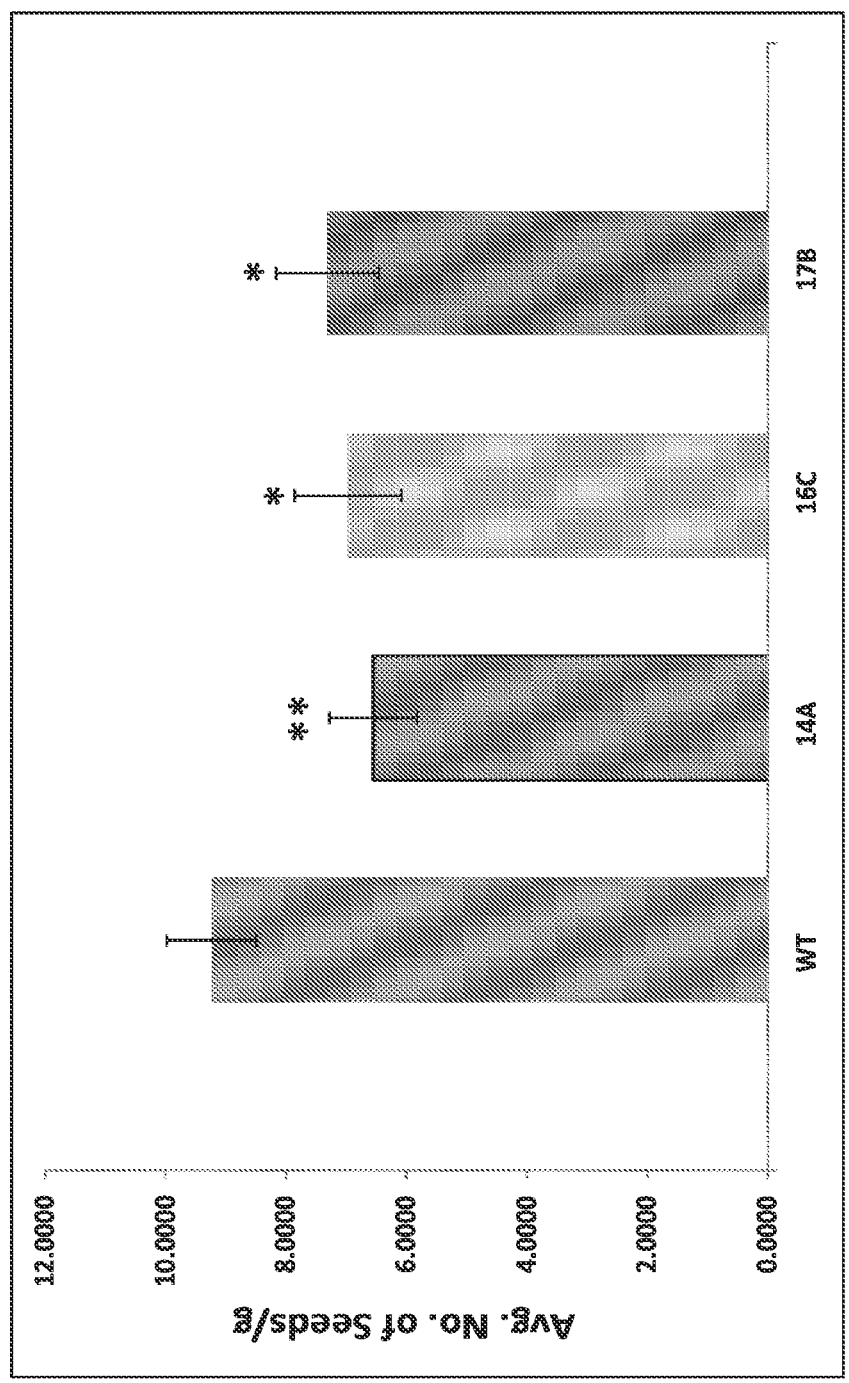
FIG. 34 is a bar chart showing average number of seeds/gram for Williams 82 wild-type control soybean (WT) and T3 psNTP9 transgenic soybean (Line 14A, 17B and 16C) plants grown in a growth chamber. Error bars represent standard deviation and asterisks above the bars indicate mean values that are statistically significantly different from one another (Student's t-test, *=P≤0.005; *=P≤0.0005; n=6).

FIG. 33 is a bar chart showing average seed weight in grams (g)/plant for Williams 82 wild-type control soybean (WT) and T3 psNTP9 transgenic soybean (Line 14A, 17B and 16C) plants grown in a growth chamber. The average seed weight in grams (g)/plant is statistically significantly higher in all transgenic lines compared to wild-type control. FIG. 34 is a bar chart showing average number of seeds/gram for Williams 82 wild-type control soybean (WT) and T3 psNTP9 transgenic soybean (Line 14A, 17B and 16C) plants grown in a growth chamber. The average number of seeds/gram is statistically significantly lower in all transgenic lines compared to wild-type control.

Figure 35:
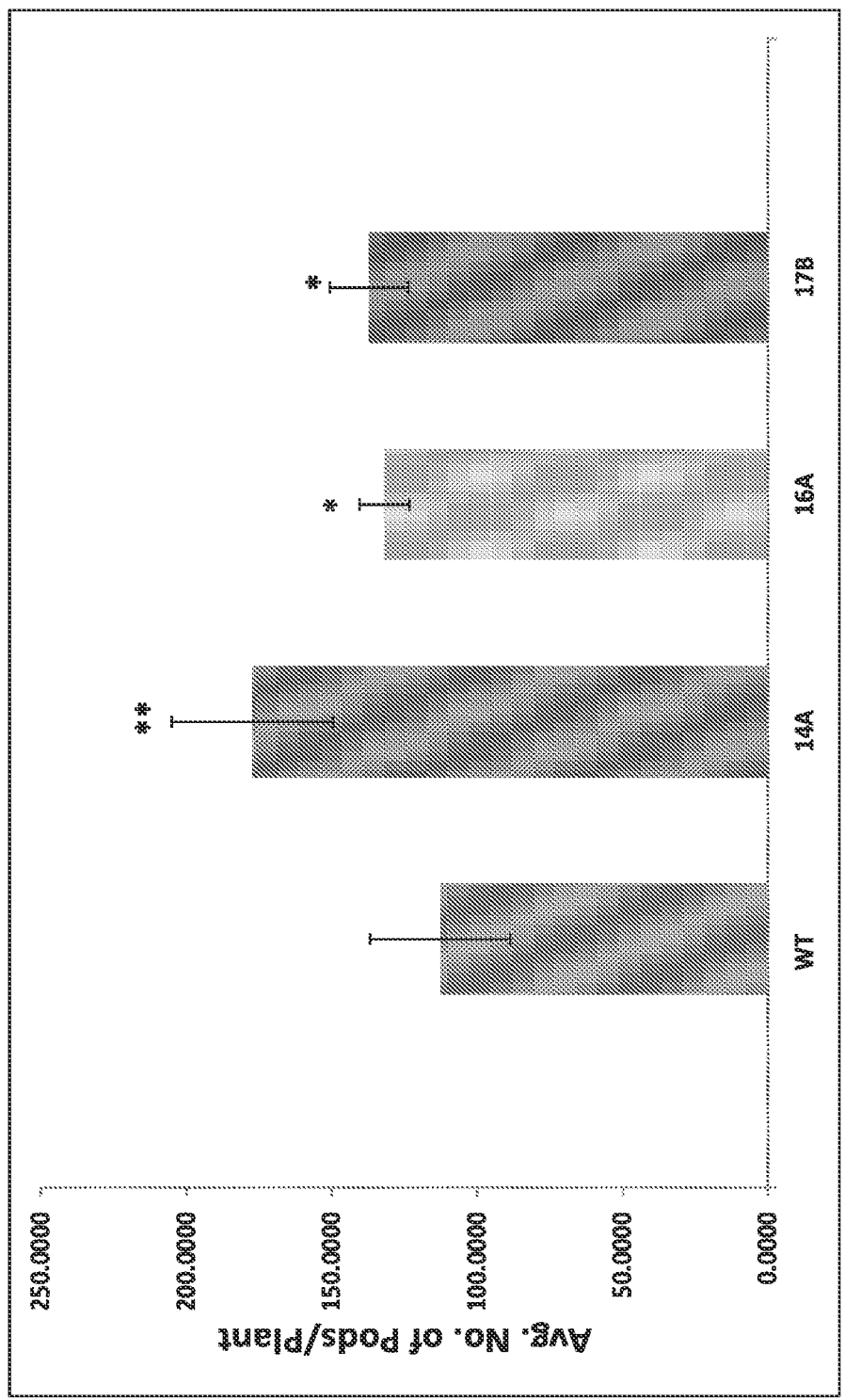
FIG. 35 is a bar chart showing average number of seed pods/plant for Williams 82 wild-type control soybean (WT) and T3 psNTP9 transgenic soybean (Line 14A, 17B and 16C) plants grown in the greenhouse. Error bars represent standard deviation and asterisks above the bars indicate mean values that are statistically significantly different from one another (Student's t-test, *=P≤0.05; **=P≤0.0005; n=16, 4, 10 and 6, respectively).
Figure 36:
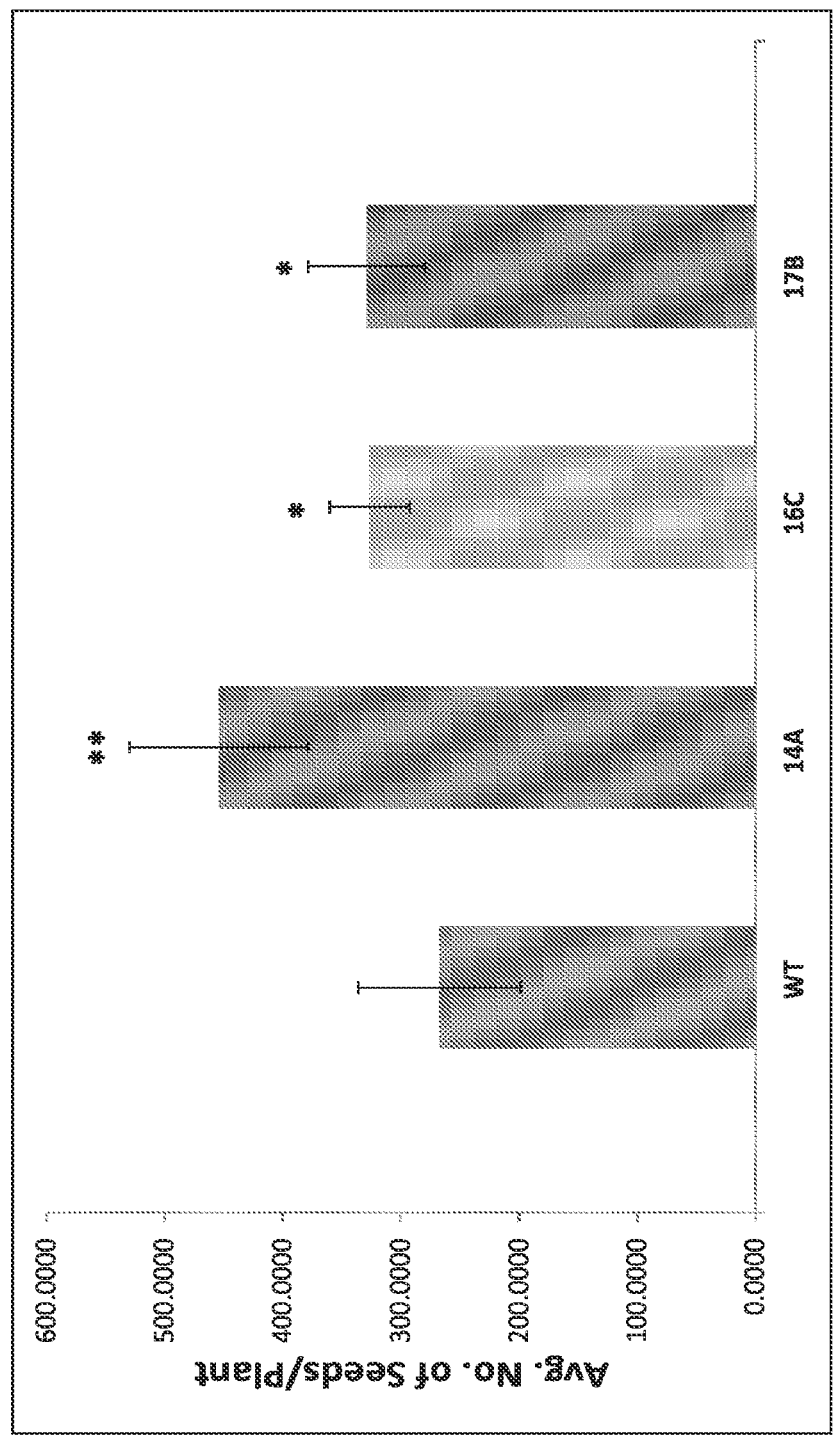
FIG. 36 is a bar chart showing average number of seeds/plant for Williams 82 wild-type control soybean (WT) and T3 psNTP9 transgenic soybean (Line 14A, 17B and 16C) plants grown in a greenhouse. Error bars represent standard deviation and asterisks above the bars indicate mean values that are statistically significantly different from one another (Student's t-test, *=P≤0.05; **=P≤0.0005; n=16, 4, 10 and 6, respectively).

FIG. 35 is a bar chart showing average number of seed pods/plant for Williams 82 wild-type control soybean (WT) and T3 psNTP9 transgenic soybean (Line 14A, 17B and 16C) plants grown in the greenhouse. The average number of seed pods/plant is statistically significantly higher in all transgenic lines compared to wild-type control. FIG. 36 is a bar chart showing average number of seeds/plant for Williams 82 wild-type control soybean (WT) and T3 psNTP9 transgenic soybean (Line 14A, 17B and 16C) plants grown in a greenhouse. The average number of seeds/plant is statistically significantly higher in all transgenic lines compared to wild-type control.

Figure 37:
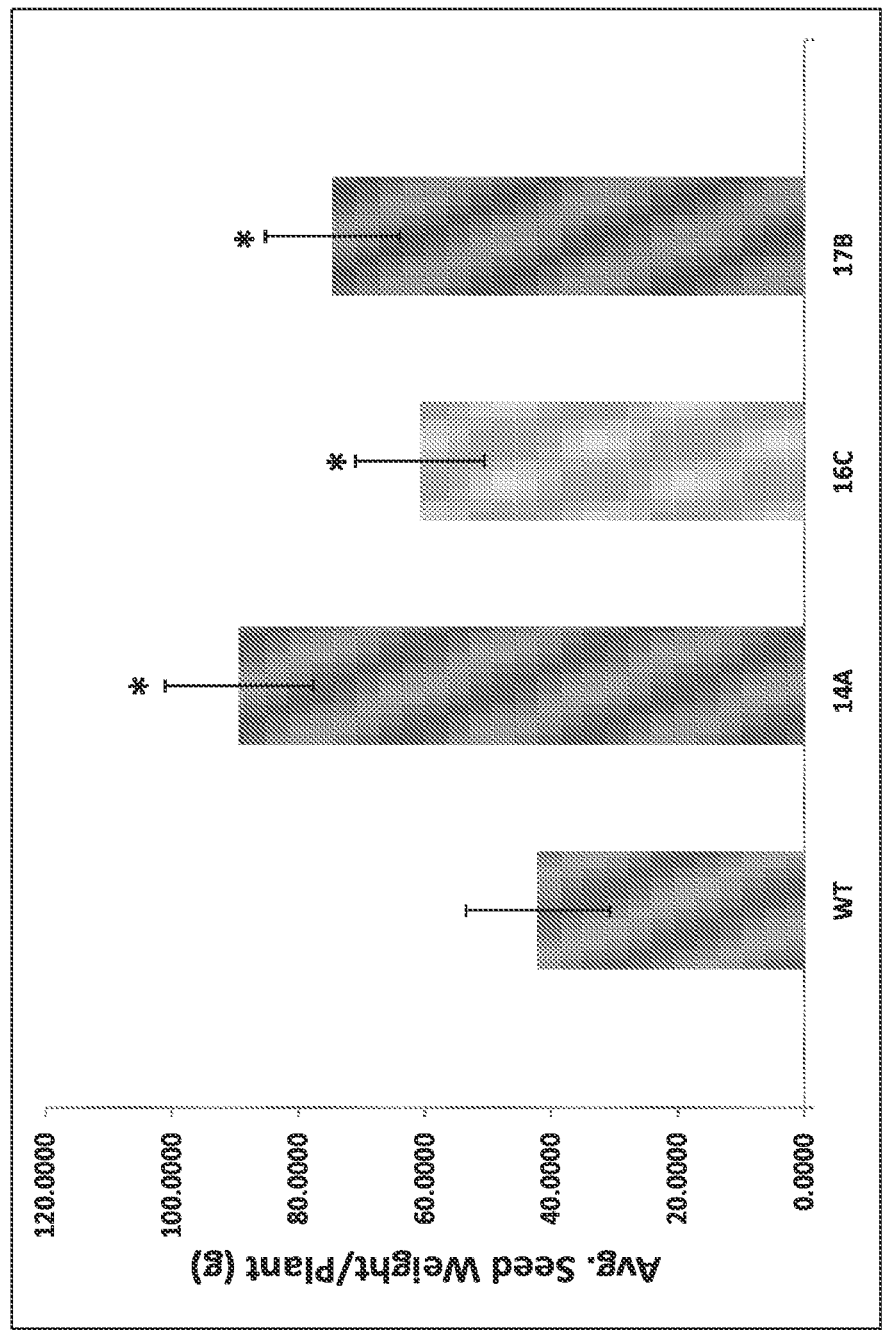
FIG. 37 is a bar chart showing average seed weight in grams (g)/plant for Williams 82 wild-type control soybean (WT) and T3 psNTP9 transgenic soybean (Line 14A, 17B and 16C) plants grown in a greenhouse. Error bars represent standard deviation and asterisks above the bars indicate mean values that are statistically significantly different from one another (Student's t-test, *=P≤0.0005; n=16, 4, 10 and 6, respectively).
Figure 38:
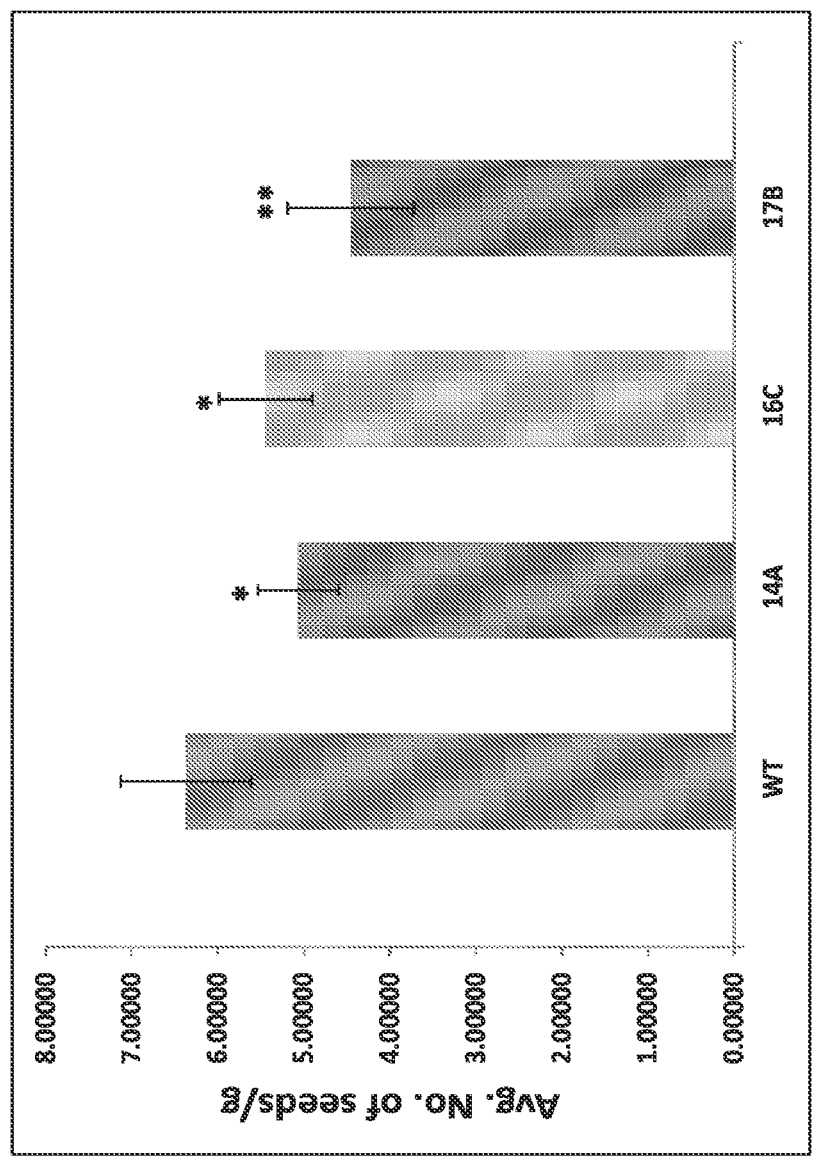
FIG. 38 is a bar chart showing average number of seeds/gram for Williams 82 wild-type control soybean (WT) and T3 psNTP9 transgenic soybean (Line 14A, 17B and 16C) plants grown in a greenhouse. Error bars represent standard deviation and asterisks above the bars indicate mean values that are statistically significantly different from one another (Student's t-test, *=P≤0.0005; n=16, 4, 10 and 6, respectively).

FIG. 37 is a bar chart showing average seed weight in grams (g)/plant for Williams 82 wild-type control soybean (WT) and T3 psNTP9 transgenic soybean (Line 14A, 17B and 16C) plants grown in a greenhouse. The average seed weight/plant is statistically significantly higher in all transgenic lines compared to wild-type control. FIG. 38 is a bar chart showing average number of seeds/gram for Williams 82 wild-type control soybean (WT) and T3 psNTP9 transgenic soybean (Line 14A, 17B and 16C) plants grown in a greenhouse. The average number of seeds/gram is statistically significantly lower in all transgenic lines compared to wild-type control.

For root architecture and root nodule studies, T3 seeds of soybean ectopically expressing psNTP9 (14A, 16C and 17B) and WT seeds were coated with Rhizobia (GUARD-N inoculant-Homesteader Hobbies). Slurry was prepared with the commercially available Rhizobia and planted in soil containing mycorrhizae (Durst and Bosworth, 1986; Park et 2010). The seeds were protected from the direct sunlight until the seedlings germinated (48-72 hours), and then moved to a greenhouse. After two weeks, the plantlets were re-potted into 5 gallon pots. The plants were grown in a greenhouse for three months. After three months, the plants were harvested for the root nodules to compare between the WT and transgenic plants. Three to six plants of each line were harvested to study the root architecture and the root nodule formation. The roots were cleaned and weighed separately to analyze and compare the bio-mass of the transgenics and wild-type soybean plants. Similarly, the root nodules were harvested and weighed separately to analyze and compare the bio-mass of the transgenics and wild-type soybean plants.

Figure 39:
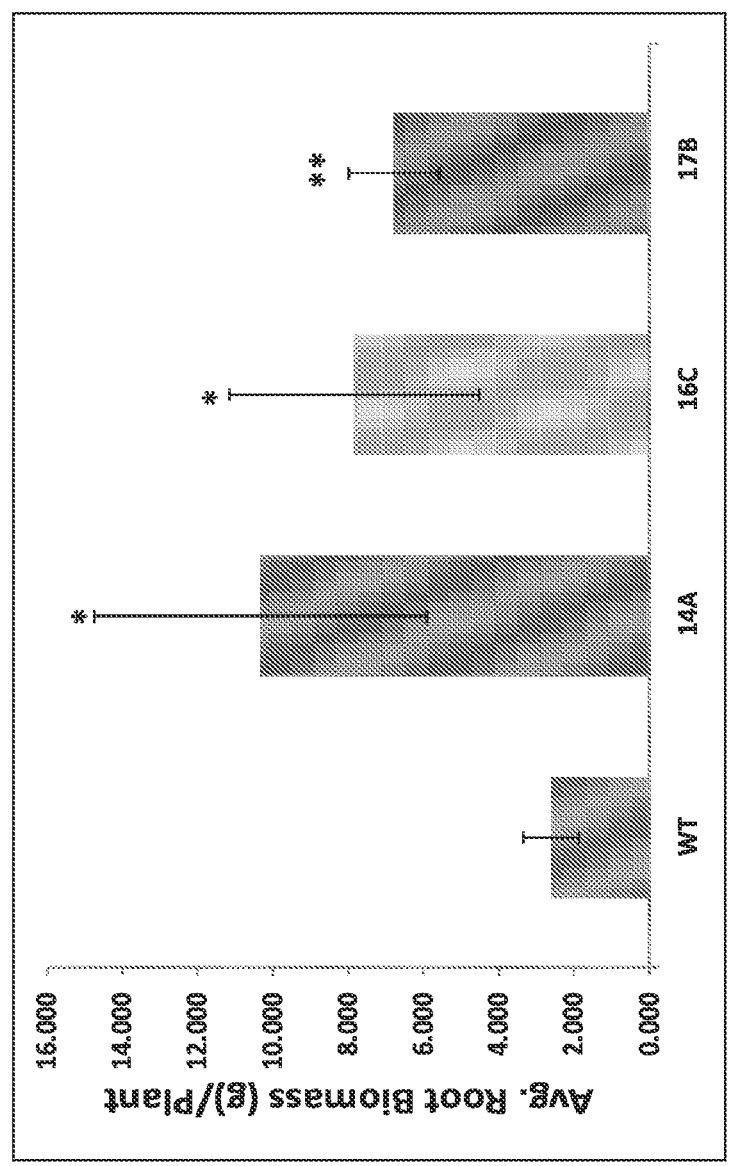
FIG. 39 is a bar graph showing root biomass for 3-month-old Williams 82 wild-type control soybean (WT) and psNTP9 transgenic soybean (Line 14A, 17B and 16C) plants. Error bars represent standard deviation and asterisks above the bars indicate mean values that are statistically significantly different from one another (Student's t-test, *=P≤0.005; **=P≤0.0005; n=6, 3, 6 and 4, respectively).

Root architecture is much more extensively developed for the 3-month-old psNTP9 transgenic soybean (Line 14A, 17B and 16C) plants compared to the Williams 82 wild-type control soybean (WT) plants. FIG. 39 is a bar graph showing root biomass for 3-month-old Williams 82 wild-type control soybean (WT) and psNTP9 transgenic soybean (Line 14A, 17B and 16C) plants. Root biomass is statistically significantly higher in all transgenic lines compared to wild-type control.

Figure 40:
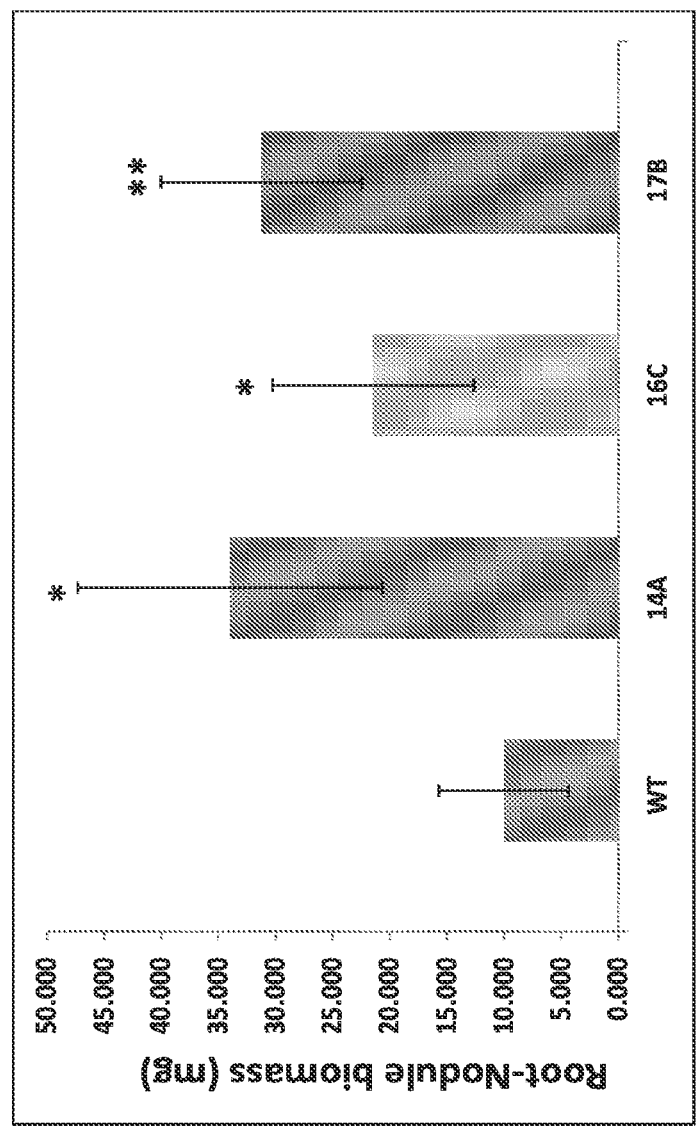
FIG. 40 is a bar graph showing root nodule biomass for 3-month-old Williams 82 wild-type control soybean (WT) and psNTP9 transgenic soybean (Line 14A, 17B and 16C) plants. Error bars represent standard deviation and asterisks above the bars indicate mean values that are statistically significantly different from one another (Student's t-test, *=P≤0.05; **=P≤0.005; n=5, 3, 5 and 4, respectively).
Figure 41:
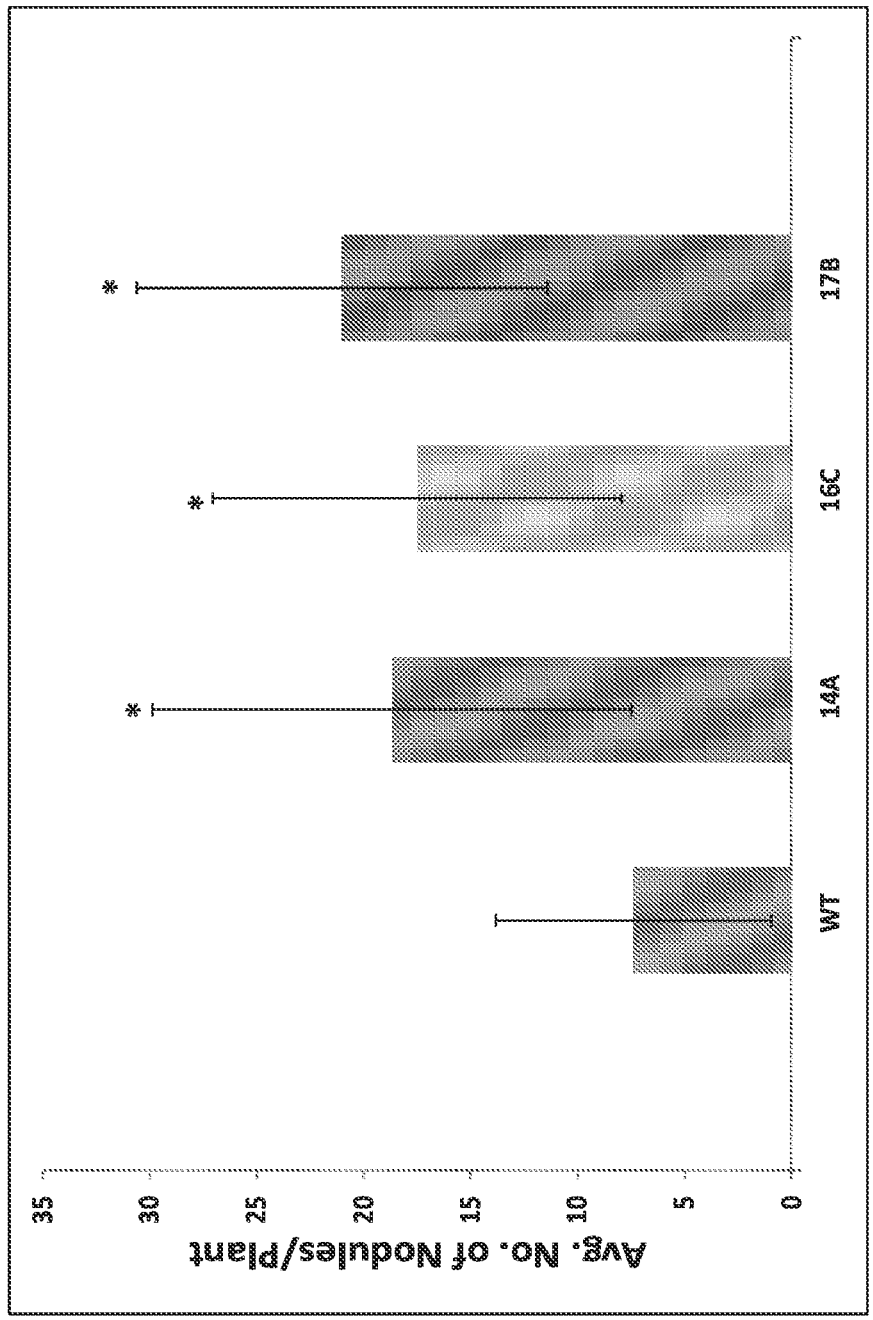
FIG. 41 is a bar graph showing average number of root nodules/plant for 3-month-old Williams 82 wild-type control soybean (WT) and psNTP9 transgenic soybean (Line 14A, 17B and 16C) plants. Error bars represent standard deviation and asterisk above the bars indicate mean values that are statistically significantly different from one another (Student's t-test, *=P≤0.05; n=8, 6, 8 and 7, respectively).

There is also an increase in the number and size of nodules for the transgenic lines compared to the wild-type control. FIG. 40 is a bar graph showing root nodule biomass for 3-month-old Williams 82 wild-type control soybean (WT) and psNTP9 transgenic soybean (Line 14A, 17B and 16C) plants. Root nodule biomass is statistically significantly higher in all transgenic lines compared to wild-type control. FIG. 41 is a bar graph showing average number of root nodules/plant for 3-month-old Williams 82 wild-type control soybean (WT) and psNTP9 transgenic soybean (Line 14A, 17B and 16C) plants. The average number of root nodules/plant is statistically significantly higher in all transgenic lines compared to wild-type control.

Example 5

Growth studies were also conducted in soybean, canola and corn transformed with pea apyrase (psNTP9), and the pea apyrase DM (Double Mutation). The psNTP9, DM (Double Mutation) and Empty Vector (Vector Only) were inserted separately into the binary vector pK7WG2. The over-expression vectors and the empty vector control were then separately transformed into Agrobacterium rhizogenes strain ARQUA-1, which were further used for hairy root transformation. The sterilized seeds were germinated on MS medium. The abaxial sides of soybean cotyledons, stem and leaves of canola and the stem of corn were wounded and infected with the cultures of transgenic A. rhizogenes strain ARQUA-1. The wounded cotyledons, stem and leaves were cultured on MS solid medium supplemented with 3% sucrose, 20 mg/L kanamycin, 400 mg/L Timentin® and 0.8% agar for the selection. The hairy roots that survived on the selection medium were sub-cultured separately on the selection medium. The expression levels of the corresponding genes in hairy roots were verified through RT-PCR analysis. The selected hairy roots were cultured on MS liquid culture supplemented with 3% sucrose, 20 mg/L kanamycin and 400 mg/L Timentin®.

Figure 42:
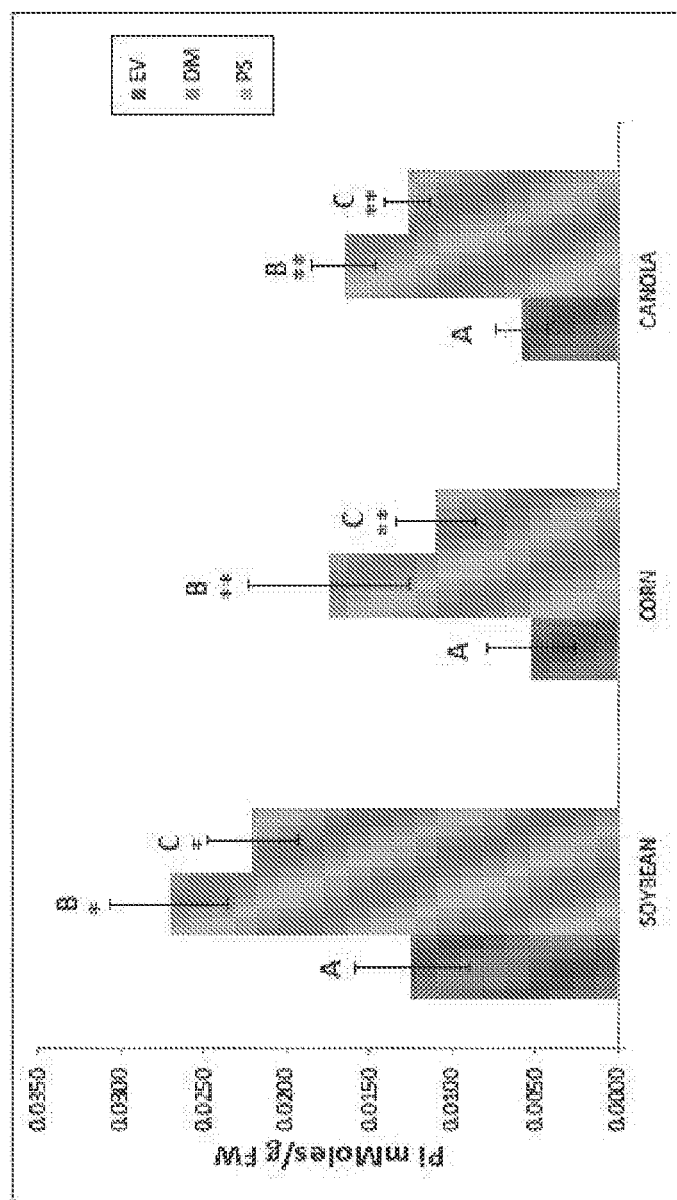
FIG. 42 is a bar chart showing phosphate uptake (Pi content based on fresh weight) for soybean, corn and canola hairy root cultures transformed with pea apyrase psNTP9 (PS), modified pea apyrase psNTP9 with double mutation (DM) and empty vector control (EV). Each bar represent means of three biological replicates. Error bars represent standard deviation and asterisks and letters above the bars indicate mean values that are statistically significantly different from one another (Student's t-test, *=P≤0.005; **=P≤0.00005; n>4 for soybean; n>8 for corn; n>6 for canola).
Figure 43:
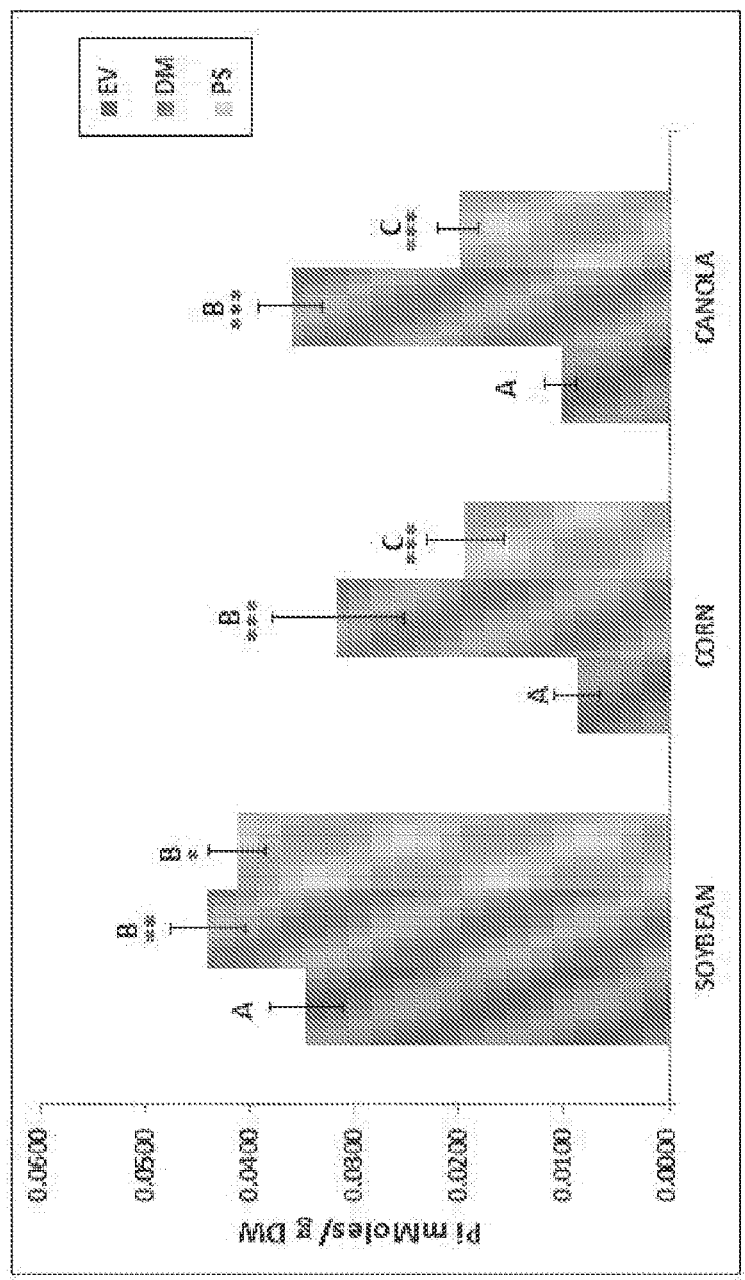
FIG. 43 is a bar chart showing phosphate uptake (Pi content based on dry weight) for soybean, corn and canola hairy root cultures transformed with pea apyrase psNTP9, modified pea apyrase psNTP9 with double mutation (DM) and empty vector control (EV). Error bars represent standard deviation and asterisks and letters above the bars indicate mean values that are statistically significantly different from one another (Student's t-test, $*=P\leq0.005$; $=P\leq0.0005$; $*=P\leq0.0005$; n>4 for soybean; n>9 for corn; n>6 for canola).

FIG. 42 is a bar chart showing phosphate uptake (Pi content based on fresh weight) for soybean, corn and canola hairy root cultures transformed with pea apyrase psNTP9 (PS), modified pea apyrase psNTP9 with double mutation (DM) and empty vector control (EV). Phosphate uptake is statistically significantly higher in all three PS hairy root culture systems compared to the EV controls. Phosphate uptake is statistically significantly higher in all three DM hairy root culture systems compared to both PS and EV controls. FIG. 43 is a bar chart showing phosphate uptake (Pi content based on dry weight) for soybean, corn and canola hairy root cultures transformed with pea apyrase psNTP9, modified pea apyrase psNTP9 with double mutation (DM) and empty vector control (EV). Phosphate uptake is statistically significantly higher in all three PS hairy root culture systems compared to the EV controls. Phosphate uptake is statistically significantly higher in all three DM hairy root culture systems compared to both PS and EV controls.

Time course growth studies were also performed in soybean plants. The psNTP9, DM (Double Mutation) and Empty Vector (Vector Only) were inserted separately into the binary vector pK7WG2. The over-expression and the empty vector control were then separately transformed into *Agrobacterium rhizogenes* strain ARQUA-1, which were further used for hairy root transformation. The sterilized soybean seeds were germinated on MS medium. The abaxial sides of cotyledons were wounded and infected with the cultures of transgenic *A. rhizogenes* strain ARQUA-1. The wounded cotyledons were cultured on MS solid medium supplemented with 3% sucrose, 20 mg/L kanamycin, 400 mg/L Timentin® and 0.8% agar for the selection. The hairy roots that survived on the selection medium were sub-cultured separately on the selection medium. The expression levels of the corresponding genes in hairy roots were verified through RT-PCR analysis. The selected hairy roots were cultured on MS liquid culture supplemented with 3% sucrose, 20 mg/L kanamycin and 400 mg/L Timentin®.

A known weight of the hairy root tissues from four different lines expressing Double Mutation (DM-1, DM-2, DM-3 and DM-4), and three different lines expressing psNTP9 (PS-1, PS-2 and PS-3) and two different lines expressing the vector only (EV-1 and EV-2) were inoculated separately into 50 ml of MS liquid medium containing 30 g/L sucrose with 400 mg/L Timentin®, and were incubated at 24° C. on an orbital shaker at approximately 80 rpm. Root growth was assayed essentially as described by Dunlop and Curtis (1991) and Kajikawa et al., (2010). Briefly, the root tissues were aseptically removed from the liquid culture, and the liquid medium on their surface was blotted thoroughly by sterilized absorbent filter papers. The blotted tissues were weighed in an Eppendorf tube aseptically, and then transferred back into the liquid medium. The liquid medium was refreshed once a week. For each line two replicates were used.

Figure 44:
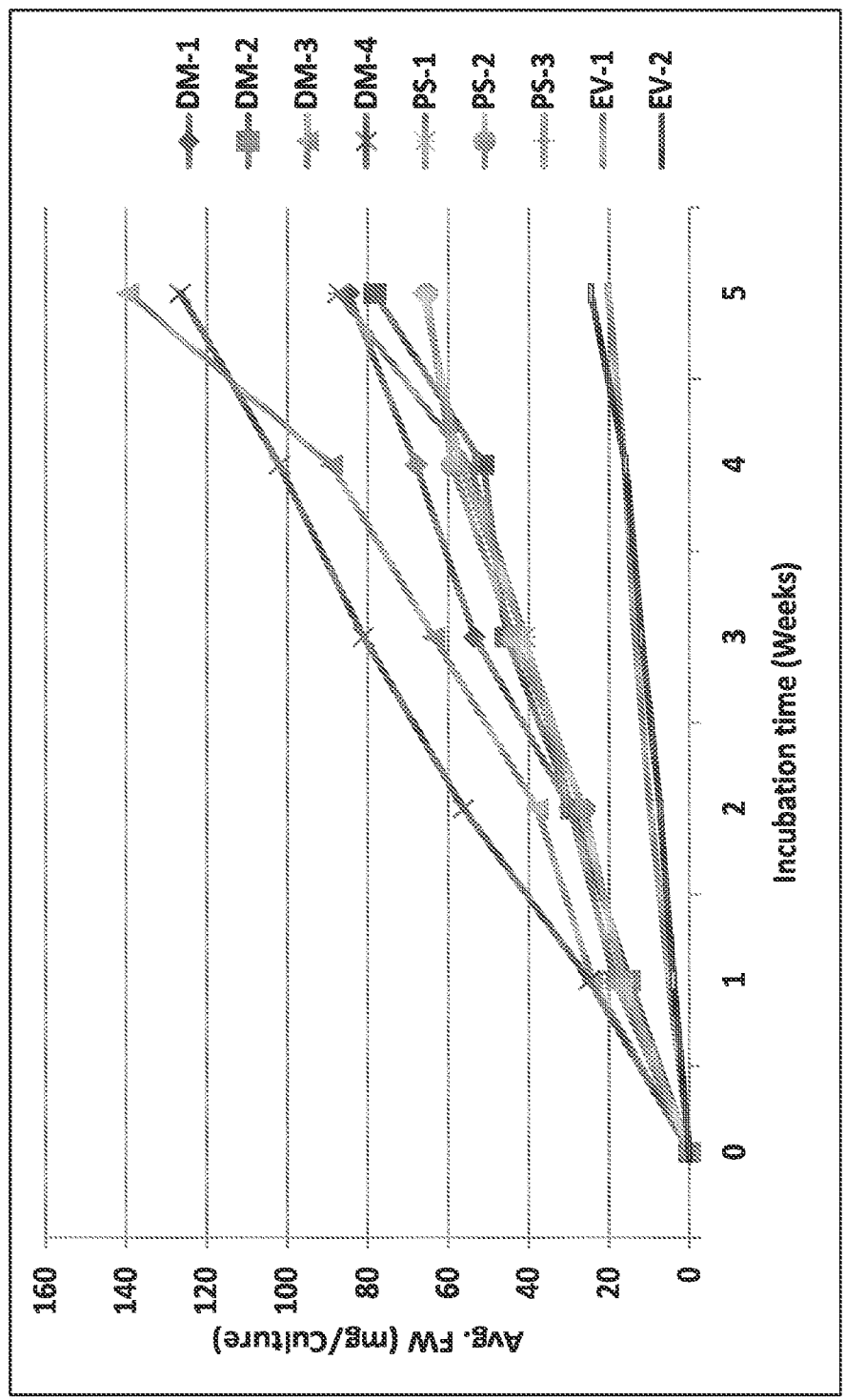
FIG. 44 is a graph showing growth rate (average fresh weight of tissue mg/culture) for soybean cultures transformed with pea apyrase psNTP9, modified pea apyrase psNTP9 with double mutation (DM) and empty vector control (EV).
Figure 45:
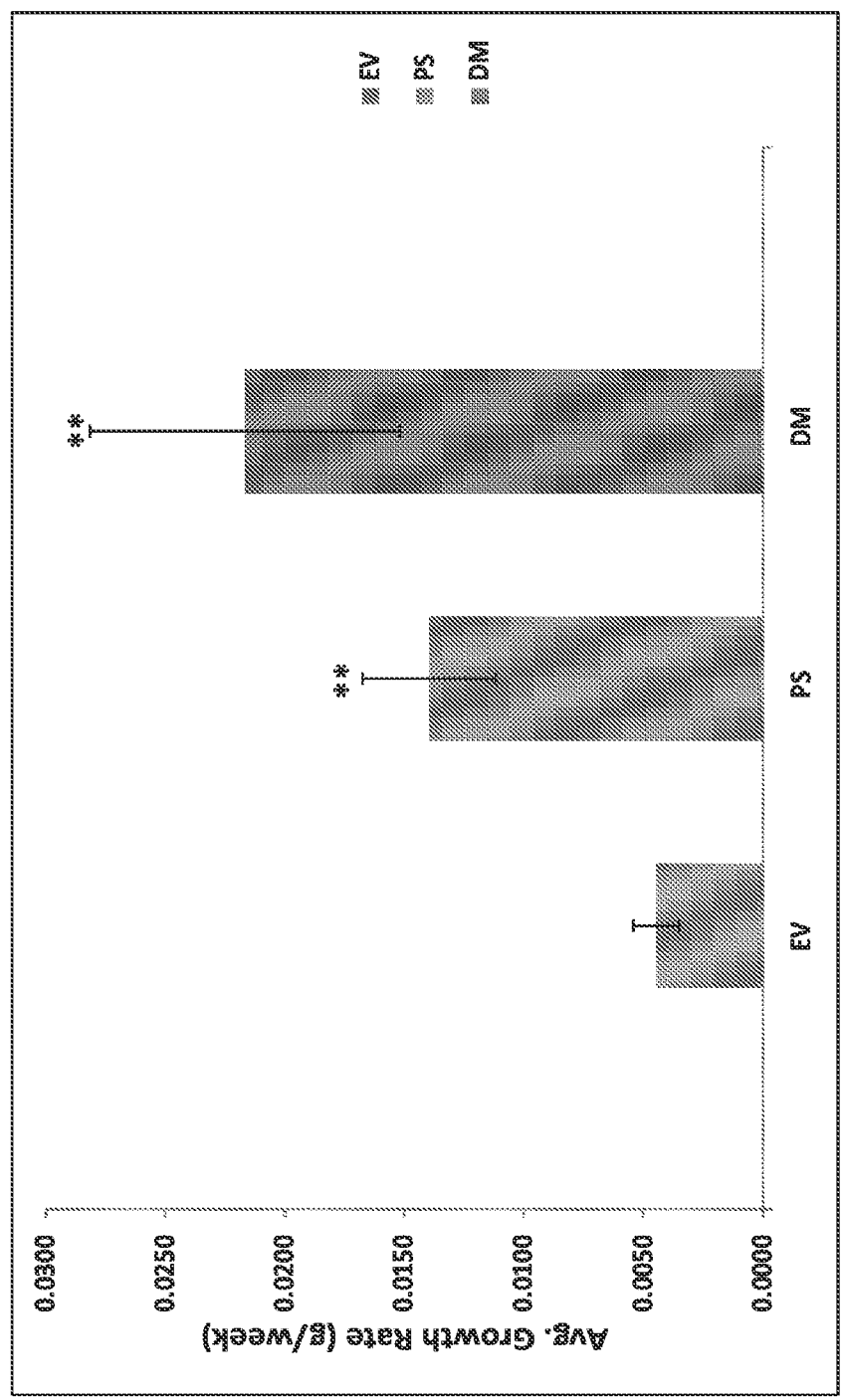
FIG. 45 is a bar graph showing average growth rates (g/week) for soybean hairy root cultures transformed with pea apyrase psNTP9 (PS), modified pea apyrase psNTP9 with double mutation (DM) and empty vector control (EV). Error bars represent standard deviation and asterisks above the bars indicate mean values that are statistically significantly different from one another (Student's t-test, $*=P\leq0.005$; n=2 for EV; n=3 for PS; n=4 for DM).

FIG. 44 is a graph showing growth rate (average fresh weight of tissue mg/culture) for soybean cultures transformed with pea apyrase psNTP9, modified pea apyrase psNTP9 with double mutation (DM) and empty vector control (EV). All of the transformed soybean lines had an increased growth rate compared to the empty vector controls. FIG. 45 is a bar graph showing average growth rates (g/week) for soybean hairy root cultures transformed with pea apyrase psNTP9 (PS), modified pea apyrase psNTP9 with double mutation (DM) and empty vector control (EV). Growth rates are statistically significantly higher for PS and DM hairy root cultures compared to the EV control.

Example 6

WT (Col-0) and homozygous T3 *Arabidopsis* transgenic seeds ectopically expressing psNTP9 (HE-1, HE-2 and HE-3, highly expressing lines, ME-1 and ME-2, moderately expressing lines) and empty vector controls (EV-1 and EV-2) were surface sterilized, and sowed on ½ MS medium supplemented with 0 mM mannitol (control) or 200 mM mannitol (osmotic stress medium). The plates were held at 4° C. for 3 days before being transferred to a growth chamber. The germination status of the WT and the transgenics were monitored and scored every 12 hours for 2 days on these media. Seeds were considered germinated when the radicle had emerged 1 mm In each study, approximately 100 seeds per line were sown, and two studies were carried out using independent seed lots (Tan et al., 2015).

Figure 46:
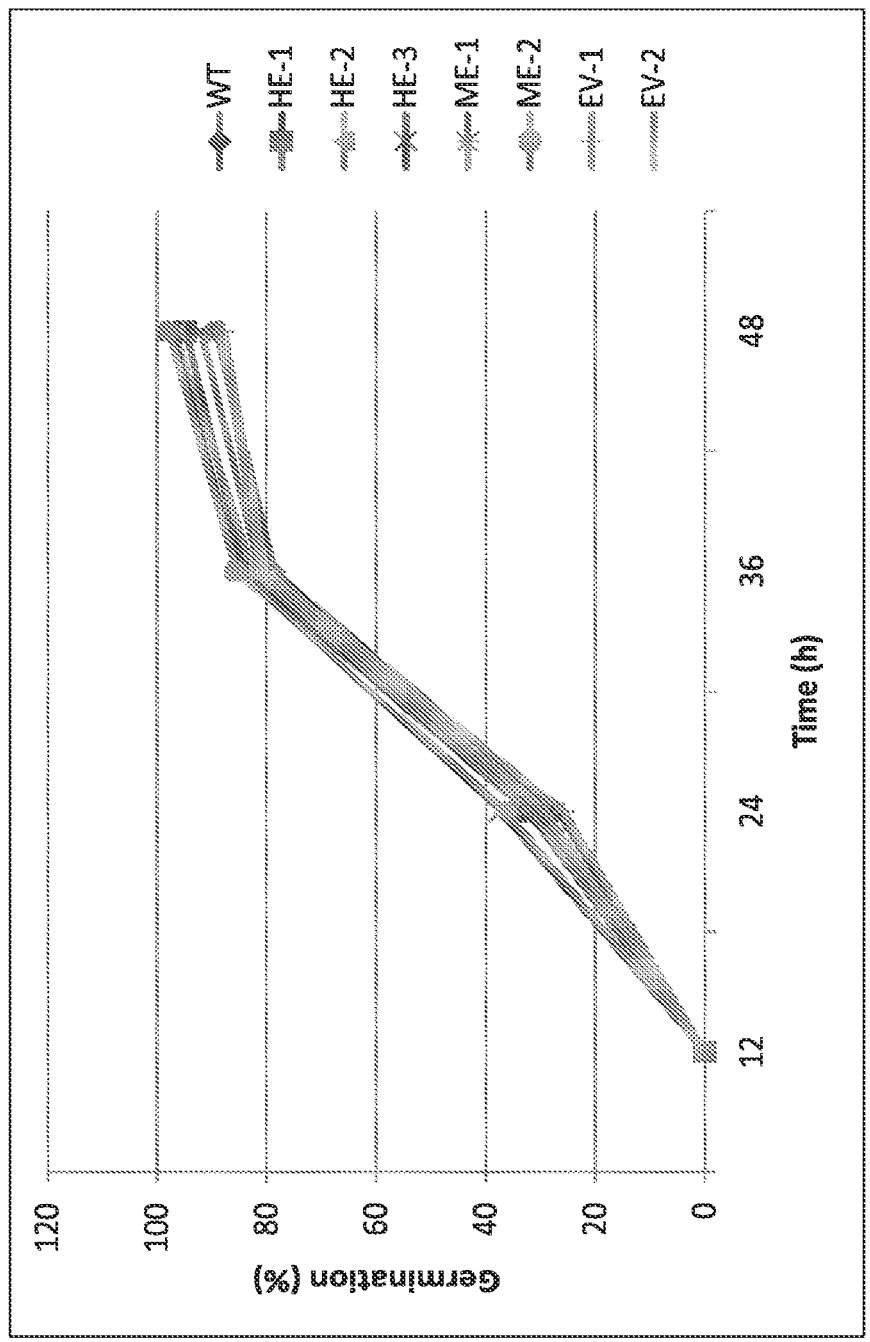
FIG. 46 is a graph showing the germination response (%) versus time (hours) of wild-type (WT), transgenic (HE-1, HE-2, HE-3, ME-1 and ME-2) and empty vector (EV-1 and EV-2) *Arabidopsis* plants after 12 hours, 24 hours, 36 hours, and 48 hours on ½ MS (nutrient medium).
Figure 47:
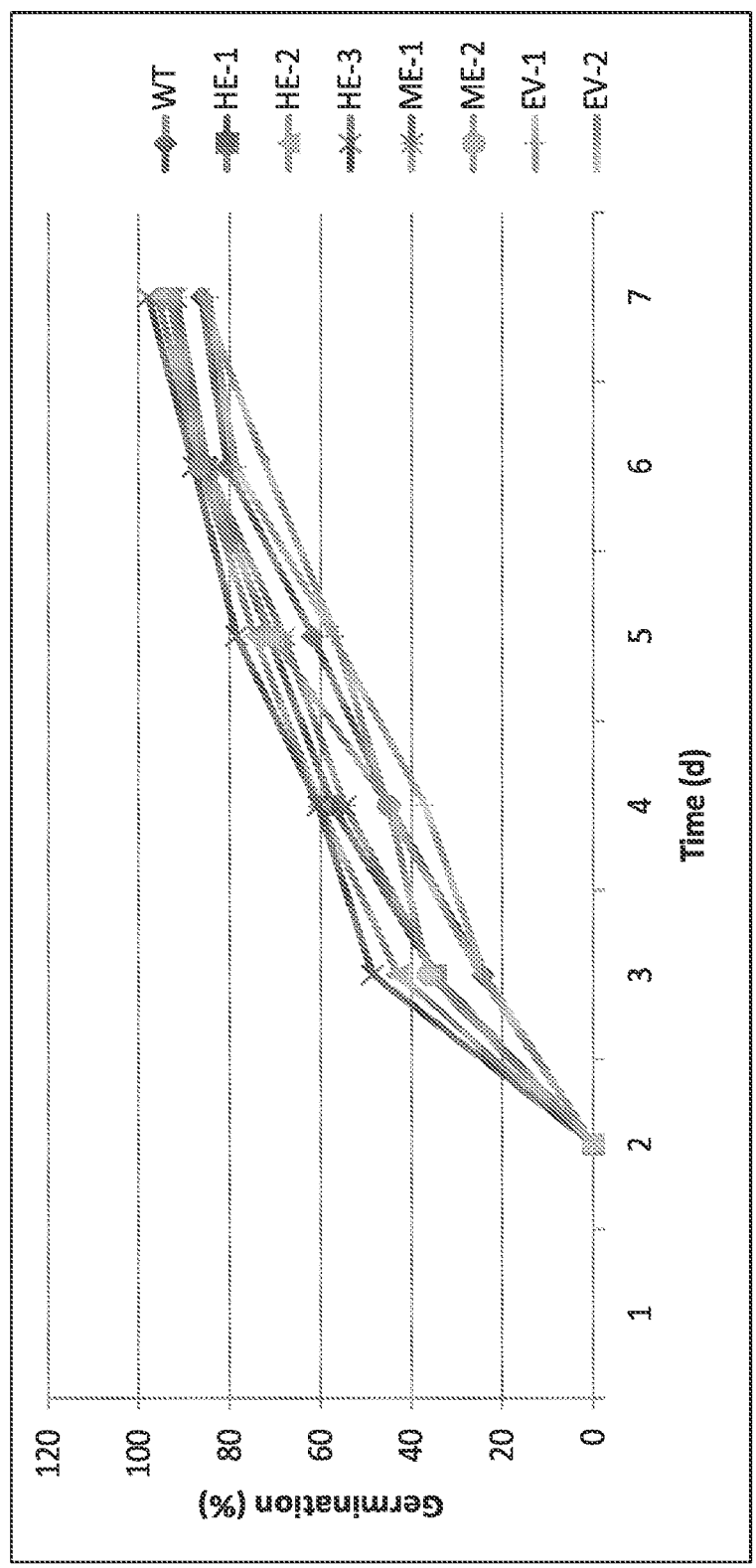
FIG. 47 is a graph showing the germination response (%) versus time (days) of wild-type (WT), transgenic (HE-1, HE-2, HE-3, ME-1 and ME-2) and empty vector (EV-1 and EV-2) *Arabidopsis* plants after 1 day, 2 days, 3 days, 4 days, 5 days, 6 days and 7 days on ½ MS with 200 mM mannitol (osmotic medium).

FIG. 46 is a graph showing the germination response (%) versus time (hours) of Col-0 wild-type (WT), empty vector control (EV1 and EV-2), transgenic highly expressing lines (HE-1, HE-2 and HE-3), and the moderately expressing lines (ME-1 and ME-2) expressing psNTP9 in *Arabidopsis* plants after 12 hours, 24 hours, 36 hours and 48 hours on ½ MS (nutrient medium). The germination (%) of HE lines are increased when compared to the ME, WT and the EV controls on ½ MS Medium. FIG. 47 is a graph showing the germination response (%) versus time (hours) of Col-0 wild-type (WT), empty vector control (EV1 and EV-2), transgenic highly expressing lines (HE-1, HE-2 and HE-3), and the moderately expressing lines (ME-1 and ME-2) expressing psNTP9 in *Arabidopsis* plants after 12 hours, 24 hours, 36 hours and 48 hours on ½ MS with 200 mM mannitol (osmotic medium). The germination (%) of HE lines are increased when compared to the ME, WT and the EV controls on ½ MS with 200 mM mannitol (osmotic medium).

Drought is one of the most important environmental constraints limiting plant growth and affecting agricultural productivity worldwide. As demonstrated in the induced-drought study and *Arabidopsis* root study, transgenic *A. thaliana* plants ectopically expressing psNTP9 had longer primary roots, more lateral roots and improved drought tolerance compared to wild-type plants. The transgenic *A. thaliana* plants ectopically expressing psNTP9 also had improved seed germination and seedling survival when exposed to osmotic and drought stress compared to wild-type plants.

Ectopic expression of the natural version and modified versions of the pea apyrase, psNTP9, improves root architecture and drought stress tolerance in plants in a variety of plant species, including *Arabidopsis thaliana*. This present disclosure includes increased root growth and improved drought resistance.

One aspect of the present disclosure is plants expressing the pea apyrase, psNTP9, or modified versions of psNTP9, show improved drought resistance, longer primary roots and more lateral roots than WT controls. Another aspect of the present disclosure is plants expressing the pea apyrase, psNTP9, or modified versions of psNTP9, show improved seed germination and seedling survival when exposed to osmotic and drought stress compared to wild-type plants.

Example 7

Design of Modified Apyrase Gene Using Helical Wheel: One approach for predicting calmodulin-binding domains in a protein is called the helical wheel. Many calmodulin-binding domains consist of approximately 15 amino acids in the primary amino acid sequence of a protein, and when the sequence of this domain is constructed into a helical wheel, half of the wheel is made up of mainly basic amino acids and the opposite half is made up of mainly hydrophobic amino acids.

One aspect of the present disclosure comprises plotting a translated nucleotide sequence of an apyrase gene on a helical wheel plot, identifying a region that appears to be a calmodulin binding region, selecting a nucleotide for modification to enhance the binding characteristics of the calmodulin binding region, preparing the modified gene, inserting the modified gene into plant tissue, wherein the resulting plant exhibits an improvement over the naturally occurring plant.

According to previous studies (O'Neil and Degrado, 1990; Chapman et al., 1991) the primary sequence in many of the calmodulin (CaM)-binding regions of the CaM-binding proteins characterized conform to the basic amphiphilic α-helix model (also called helical wheel model), with hydrophobic amino acids clustered on one side of the helix and basic (positively-charged) amino acids on the opposite side. FIG. 48A and FIG. 48B illustrate two sequences in psNTP9 that are similar to classical CaM-binding domains, but only one of them was demonstrated to actually be a CaM-binding domain (FIG. 48A), while the other one was shown not to bind CaM (FIG. 48B; Hsieh et al., 2000). The sequence that did bind to CaM (FIG. 48A) conformed closely to the amphilic α-helix model, while the one that did not (FIG. 48B) was less hydrophobic on one side of the helix and less basic on the other side than the sequence that did bind CaM. The inventor's reasoned that making the α-helix of FIG. 48B more hydrophobic on one side and more basic on the other side would make it more likely to bind CaM. This could be done by substituting a hydrophobic amino acid such as F, I, L, M, or Y for the S on the hydrophobic side, and substituting a basic amino acid such as K or R for the P on the basic amino acid side (standard single letter amino acid abbreviations). Following these guidelines any sequence that nearly fits to the amphiphilic α-helix model could be made more likely to bind CaM by directed amino acid substitutions, for example using gene editing technologies, including, but not limited to, CRISPR, Talens, Zinc Fingers, or other similar gene editing techniques.

For example, AtAPY1 and AtAPY2 have primary sequences that are 87% identical, but whereas AtAPY1 has a CaM-binding domain, AtAPY2 does not (Steinebrunner et al., 2000). The sequence 298 through 311 in AtAPY2 that does not bind CaM differs from the parallel region in AtAPY1 (297-310) that does bind CaM at only two positions underlined in FIG. 43C. By changing the E on the hydrophobic side (left side of the dividing line) to a hydrophobic amino acid and the D on the basic side (right side of the dividing line) this sequence in AtAPY2 could be converted to one that would bind CaM.

In the present disclosure, the non-calmodulin-binding sequence in psNTP9 (FIG. 48B) was modified to make it more likely to bind calmodulin, such that this apyrase would have an increased ability to interact with calcium-activated calmodulin, and that this change might increase the activity of psNTP9 in regulating plant growth and development. Two single nucleotide changes were made in the open reading frame of the psNTP9 transcript. These changes were translated into amino acid changes to make the sequence in FIG. 48B domain more likely to bind calmodulin. The first base pair change, when translated, replaced a proline residue (P) with an arginine residue (R), which made the basic half of the helical wheel more basic. The second base-pair change, when translated, replaced a serine residue (S) with a leucine (L), which made the hydrophobic half of the helical wheel more hydrophobic. The resulting amino acid and DNA sequences are shown in SEQ ID NOS:2 and 4, respectively.

It is contemplated that any embodiment disclosed herein can be implemented with respect to any method, kit, reagent, or composition of the present disclosure, and vice versa. Furthermore, compositions of the present disclosure can be used to achieve methods of the present disclosure.

It will be understood that particular embodiments described herein are shown by way of illustration and not as limitations. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of." As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

REFERENCES

Abramoff, et al. (2004). "Image Processing with ImageJ." *Biophotonics International* 11:36-42.

Alves de Paiva Rolla, et al. (2014). "Phenotyping soybean plants transformed with rd29A:AtDREB1A for drought tolerance in the greenhouse and field." *Transgenic Research* 23:75-87.

Barker. (2010). "Science and Technology of Organic Farming." CRC Press.

Cho, et al. (2000). "High-efficiency induction of soybean hairy roots and propagation of the soybean cyst nematode." *Planta* 210:195-204.

Clark, et al. (2014). "Breakthroughs spotlighting roles for extracellular nucleotides and apyrases in stress responses and plant growth and development." *Plant Science* 225: 107-116.

Clough, et al. (1998). "Floral dip: a simplified method for Agrobacterium-mediated transformation of *Arabidopsis thaliana*." *Plant J.* 16:735-743.

Dunlop and Curtis. (1991). "Synergistic response of plant hairy-root cultures to phosphate limitation and fungal elicitation." *Biotechnol. Prog.* 7:434-438.

Durst and Bosworth. (1986). "Inoculation of forage and grain legumes." *Agronomy Facts* 11. Penn State Department of Crop and Soil Sciences, Cooperative Extension. (cropsoil.psu.edu/extension/facts/agronomy-facts-11).

Haitao, et al. (2015). "Low Temperature-Induced 30 (LTI30) positively regulates drought stress resistance in *Arabidopsis*: effect on abscisic acid sensitivity and hydrogen peroxide accumulation." *Front. Plant Sci.* 6:893.

Hsieh, et al. (2000). "Regulation of a recombinant pea nuclear apyrase by calmodulin and casein kinase II." *Biochem. Biophys. Acta.* 1494:248-255.

Cha, et al. (2015), "A novel thiol-reductase activity of *Arabidopsis* YUC6 confers drought tolerance independently of auxin biosynthesis." *Nat. Commun.* 6:8041.

Chapman, et al. (1991). "Characterization of the calmodulin binding domain of neuromodulin." *J. Biol. Chem.* 266: 207-213.

Kim (2013). "*Agrobacterium rhizogenes*-induced cotton hairy root culture as an alternative tool for cotton functional genomics." *Methods in Molecular Biology* (Clifton, NJ) 958:179-187.

Kajikawa, et al. (2010). "Establishment of a transgenic hairy root system in wild and domesticated watermelon (*Citrullus lanatus*) for studying root vigor under drought." *Plant Cell Rep.* 29:771-778.

Knowles. (2011). "The GDA1 CD39 superfamily: NTP-Dases with diverse functions." *Purinergic Signal.* 7: 1-45.

Luth, et al. (2015). "*Agrobacterium* Protocols: Soybean [*Glycine max* (L.) Mem]." *Methods in Molecular Biology* (Clifton, N.J.) 1223:275-284.

Ma, et al. (2001). "Regulation of root hair density by phosphorus availability in *Arabidopsis thaliana*." *Plant Cell and Environment* 24:459-467.

O'Neil and DeGrado. (1990). "How calmodulin binds its targets: sequence independent recognition of amphiphilic α-helices." *Trends Biochem. Sci.* 15:59-64.

Park, et al. (2010). "Inoculants and soil amendments for organic growers." *Fact Sheet SAG*-17-10 The Ohio State University Extension. (ohioline.osu.edu/sag-fact/pdf/0017.pdf).

Paz, et al. (2006). "Improved cotyledonary node method using an alternative explant derived from mature seed for efficient *Agrobacterium*-mediated soybean transformation." *Plant Cell Rep.* 25:206-213.

Ren, et al. (2012). "*Brassica napus* PHR1 gene encoding a MYB-like protein functions in response to phosphate starvation." *PLoS One* 7: e44005.

Root Architecture studies: plantscience.psu.edu/research/labs/roots/methods/methods-info/root-hairs/root-hair-imaging-protocol/b.-root-image-capture-for-root-hair-length-density.

Smith, et al. (2015). "Mycorrhizal associations and phosphorus acquisition: from cells to ecosystems." *Annual Plant Reviews* 48:409-440.

Steinebrunner, et al. (2000). "Molecular and biochemical comparison of two different apyrases from *Arabidopsis thaliana*." *Plant Physiol. Biochem.* 38:913-922.

Tan, et al. (2015). "Overexpression of MpCYS2, a phytocystatin gene from *Malus prunifolia* (Willd.) Borkh., confers drought tolerance and protects against oxidative stress in *Arabidopsis*." *Plant Cell Tiss Org. Cult.* 123:15-27.

Thomas, et al. (1999). "Apyrase functions in phosphate transport and mobilizes phosphate from extracellular ATP." *Plant Physiol.* 119:543-551.

Wu, et al. (2007). "Apyrases (NTPDases) play key role in growth control in *Arabidopsis*." *Plant Physiol.* 144:961-975.

Zhang, et al. (2006). "*Agrobacterium*-mediated transformation of *Arabidopsis thaliana* using the floral dip method." *Nature Protocols* 1:641-646.

The invention claimed is:

1. An apyrase coding sequence encoding the polypeptide sequence of SEQ ID NO:2.

2. A modified apyrase gene comprising the nucleotide sequence of SEQ ID NO:4.

3. A recombinant DNA molecule comprising a heterologous promoter functional in a plant cell, operably linked to a nucleic acid sequence encoding a polypeptide that has the polypeptide sequence of SEQ ID NO:2.

4. The DNA molecule of claim 3, wherein the nucleic acid sequence is SEQ ID NO:4.

5. A polypeptide having the amino acid sequence of SEQ ID NO:2.

* * * * *

SEQUENCE LISTING

<160> NUMBER OF SEQ ID NOS: 4

<210> SEQ ID NO 1
<211> LENGTH: 455
<212> TYPE: PRT
<213> ORGANISM: Pisum sativum

<400> SEQUENCE: 1

```
Met Glu Leu Leu Ile Lys Leu Ile Thr Phe Leu Leu Phe Ser Met Pro
1               5                   10                  15

Ala Ile Thr Ser Ser Gln Tyr Leu Gly Asn Asn Leu Leu Thr Ser Arg
                20                  25                  30

Lys Ile Phe Leu Lys Gln Glu Glu Ile Ser Ser Tyr Ala Val Val Phe
            35                  40                  45

Asp Ala Gly Ser Thr Gly Ser Arg Ile His Val Tyr His Phe Asn Gln
        50                  55                  60

Asn Leu Asp Leu Leu His Ile Gly Lys Gly Val Glu Tyr Tyr Asn Lys
65                  70                  75                  80

Ile Thr Pro Gly Leu Ser Ser Tyr Ala Asn Asn Pro Glu Gln Ala Ala
                85                  90                  95

Lys Ser Leu Ile Pro Leu Leu Glu Gln Ala Glu Asp Val Val Pro Asp
            100                 105                 110

Asp Leu Gln Pro Lys Thr Pro Val Arg Leu Gly Ala Thr Ala Gly Leu
        115                 120                 125

Arg Leu Leu Asn Gly Asp Ala Ser Glu Lys Ile Leu Gln Ser Val Arg
    130                 135                 140

Asp Met Leu Ser Asn Arg Ser Thr Phe Asn Val Gln Pro Asp Ala Val
145                 150                 155                 160

Ser Ile Ile Asp Gly Thr Gln Glu Gly Ser Tyr Leu Trp Val Thr Val
                165                 170                 175

Asn Tyr Ala Leu Gly Asn Leu Gly Lys Lys Tyr Thr Lys Thr Val Gly
            180                 185                 190

Val Ile Asp Leu Gly Gly Gly Ser Val Gln Met Ala Tyr Ala Val Ser
        195                 200                 205

Lys Lys Thr Ala Lys Asn Ala Pro Lys Val Ala Asp Gly Asp Asp Pro
    210                 215                 220

Tyr Ile Lys Lys Val Val Leu Lys Gly Ile Pro Tyr Asp Leu Tyr Val
225                 230                 235                 240

His Ser Tyr Leu His Phe Gly Arg Glu Ala Ser Arg Ala Glu Ile Leu
                245                 250                 255

Lys Leu Thr Pro Arg Ser Pro Asn Pro Cys Leu Leu Ala Gly Phe Asn
            260                 265                 270

Gly Ile Tyr Thr Tyr Ser Gly Glu Glu Phe Lys Ala Thr Ala Tyr Thr
        275                 280                 285

Ser Gly Ala Asn Phe Asn Lys Cys Lys Asn Thr Ile Arg Lys Ala Leu
    290                 295                 300

Lys Leu Asn Tyr Pro Cys Pro Tyr Gln Asn Cys Thr Phe Gly Gly Ile
305                 310                 315                 320

Trp Asn Gly Gly Gly Gly Asn Gly Gln Lys Asn Leu Phe Ala Ser Ser
                325                 330                 335

Ser Phe Phe Tyr Leu Pro Glu Asp Thr Gly Met Val Asp Ala Ser Thr
            340                 345                 350

Pro Asn Phe Ile Leu Arg Pro Val Asp Ile Glu Thr Lys Ala Lys Glu
        355                 360                 365
```

```
Ala Cys Ala Leu Asn Phe Glu Asp Ala Lys Ser Thr Tyr Pro Phe Leu
    370                 375                 380

Asp Lys Lys Asn Val Ala Ser Tyr Val Cys Met Asp Leu Ile Tyr Gln
385                 390                 395                 400

Tyr Val Leu Leu Val Asp Gly Phe Gly Leu Asp Pro Leu Gln Lys Ile
            405                 410                 415

Thr Ser Gly Lys Glu Ile Glu Tyr Gln Asp Ala Ile Val Glu Ala Ala
                420                 425                 430

Trp Pro Leu Gly Asn Ala Val Glu Ala Ile Ser Ala Leu Pro Lys Phe
            435                 440                 445

Glu Arg Leu Met Tyr Phe Val
    450                 455

<210> SEQ ID NO 2
<211> LENGTH: 455
<212> TYPE: PRT
<213> ORGANISM: Artificial sequence
<220> FEATURE:
<223> OTHER INFORMATION: Synthetic sequence

<400> SEQUENCE: 2

Met Glu Leu Leu Ile Lys Leu Ile Thr Phe Leu Leu Phe Ser Met Pro
1               5                   10                  15

Ala Ile Thr Ser Ser Gln Tyr Leu Gly Asn Asn Leu Leu Thr Ser Arg
            20                  25                  30

Lys Ile Phe Leu Lys Gln Glu Ile Ser Ser Tyr Ala Val Val Phe
        35                  40                  45

Asp Ala Gly Ser Thr Gly Ser Arg Ile His Val Tyr His Phe Asn Gln
50                  55                  60

Asn Leu Asp Leu Leu His Ile Gly Lys Gly Val Glu Tyr Tyr Asn Lys
65                  70                  75                  80

Ile Thr Pro Gly Leu Ser Ser Tyr Ala Asn Asn Pro Glu Gln Ala Ala
                85                  90                  95

Lys Ser Leu Ile Pro Leu Leu Glu Gln Ala Glu Asp Val Val Pro Asp
            100                 105                 110

Asp Leu Gln Pro Lys Thr Pro Val Arg Leu Gly Ala Thr Ala Gly Leu
        115                 120                 125

Arg Leu Leu Asn Gly Asp Ala Ser Glu Lys Ile Leu Gln Ser Val Arg
130                 135                 140

Asp Met Leu Ser Asn Arg Ser Thr Phe Asn Val Gln Pro Asp Ala Val
145                 150                 155                 160

Ser Ile Ile Asp Gly Thr Gln Glu Gly Ser Tyr Leu Trp Val Thr Val
                165                 170                 175

Asn Tyr Ala Leu Gly Asn Leu Gly Lys Lys Tyr Thr Lys Thr Val Gly
            180                 185                 190

Val Ile Asp Leu Gly Gly Gly Ser Val Gln Met Ala Tyr Ala Val Leu
        195                 200                 205

Lys Lys Thr Ala Lys Asn Ala Arg Lys Val Ala Asp Gly Asp Asp Pro
210                 215                 220

Tyr Ile Lys Lys Val Val Leu Lys Gly Ile Pro Tyr Asp Leu Tyr Val
225                 230                 235                 240

His Ser Tyr Leu His Phe Gly Arg Glu Ala Ser Arg Ala Glu Ile Leu
                245                 250                 255

Lys Leu Thr Pro Arg Ser Pro Asn Pro Cys Leu Leu Ala Gly Phe Asn
            260                 265                 270
```

Gly Ile Tyr Thr Tyr Ser Gly Glu Glu Phe Lys Ala Thr Ala Tyr Thr
            275                 280                 285

Ser Gly Ala Asn Phe Asn Lys Cys Lys Asn Thr Ile Arg Lys Ala Leu
        290                 295                 300

Lys Leu Asn Tyr Pro Cys Pro Tyr Gln Asn Cys Thr Phe Gly Gly Ile
305                 310                 315                 320

Trp Asn Gly Gly Gly Asn Gly Gln Lys Asn Leu Phe Ala Ser Ser
                325                 330                 335

Ser Phe Phe Tyr Leu Pro Glu Asp Thr Gly Met Val Asp Ala Ser Thr
                340                 345                 350

Pro Asn Phe Ile Leu Arg Pro Val Asp Ile Glu Thr Lys Ala Lys Glu
            355                 360                 365

Ala Cys Ala Leu Asn Phe Glu Asp Ala Lys Ser Thr Tyr Pro Phe Leu
        370                 375                 380

Asp Lys Lys Asn Val Ala Ser Tyr Val Cys Met Asp Leu Ile Tyr Gln
385                 390                 395                 400

Tyr Val Leu Leu Val Asp Gly Phe Gly Leu Asp Pro Leu Gln Lys Ile
                405                 410                 415

Thr Ser Gly Lys Glu Ile Glu Tyr Gln Asp Ala Ile Val Glu Ala Ala
            420                 425                 430

Trp Pro Leu Gly Asn Ala Val Glu Ala Ile Ser Ala Leu Pro Lys Phe
        435                 440                 445

Glu Arg Leu Met Tyr Phe Val
    450                 455

<210> SEQ ID NO 3
<211> LENGTH: 1368
<212> TYPE: DNA
<213> ORGANISM: Pisum sativum

<400> SEQUENCE: 3
atggagctcc ttattaaact tatcactttt ctactatttt ctatgcctgc aatcacttcc      60
tcccaatact taggaaacaa cctactcacc agtagaaaga ttttcctaaa acaagaggaa     120
atttcctctt acgctgtcgt attcgatgct ggtagcactg tagtcgcat tcatgtttac      180 cattttaacc agaacttaga tcttcttcat attggcaaag gtgtcgagta ttataataag     240
ataacacctg gttgagttc atacgctaat aatccagaac aggctgcaaa atctctcatt     300
ccacttttag agcaagcaga agatgtcgtc cccgacgatc ttcaacccaa gacacccgtt     360
agacttgggg caactgccgg tttaaggctt ttgaatggag atgcttctga aaagatattg     420
caatcggtaa gggatatgct gagcaacaga agtaccttca cgttcaacc agacgcagtt      480 tctataattg atggaaccca agaaggttct tatctatggg tgacagttaa ctatgcattg     540
ggaaatttag ggaaaaagta cacaaaaaca gttggagtaa tagatcttgg aggtggatca     600
gttcaaatgg cgtatgcagt atcaaagaaa actgctaaaa atgctccaaa agttgcagat     660
ggagatgatc catacatcaa gaaggttgta ctcaagggaa taccatatga tctctatgtt     720
cacagttact tacacttcgg tagagaagca tctcgagcag agattttgaa gctcactcct     780
cgttctccta acccttgcct tttagctgga tttaatggaa tctatacata ttcaggagaa     840
gagtttaagg caactgctta cacttctggt gcaaacttta taaatgcaa aaacacaatt     900 cgtaaggctc ttaagttgaa ctatccttgt ccatatcaga attgcacttt tggtggaatt     960
tggaatggtg gaggaggaaa tggacagaaa aacctttttg cttcttcatc tttctttac    1020 ctacctgaag ataccggtat ggttgatgca agcacaccta atttcatact tcggccggtc    1080

```
gatattgaga ctaaagctaa agaagcttgc gcgttaaact tcgaggatgc gaaatctact    1140
tatccatttc ttgataagaa aaatgtagct tcatatgtat gcatggatct tatatatcag    1200
tatgtgttac tcgttgatgg atttggtctt gatccattgc aaaagattac atcagggaag    1260
gaaattgaat accaagatgc tattgtggaa gctgcatggc ctctaggcaa tgctgtagaa    1320
gccatatcag ctttacctaa atttgagcga ttgatgtatt ttgtttaa                1368

<210> SEQ ID NO 4
<211> LENGTH: 1368
<212> TYPE: DNA
<213> ORGANISM: Artificial sequence
<220> FEATURE:
<223> OTHER INFORMATION: Synthetic sequence

<400> SEQUENCE: 4
atggagctcc ttattaaact tatcactttt ctactatttt ctatgcctgc aatcacttcc      60
tcccaatact taggaaacaa cctactcacc agtagaaaga ttttcctaaa acaagaggaa     120
atttcctctt acgctgtcgt attcgatgct ggtagcactg gtagtcgcat tcatgtttac     180
cattttaacc agaacttaga tcttcttcat attggcaaag gtgtcgagta ttataataag     240
ataacacctg gtttgagttc atacgctaat aatccagaac aggctgcaaa atctctcatt     300
ccacttttag agcaagcaga agatgtcgtc cccgacgatc ttcaacccaa gacaccgtt     360 agacttgggg caactgccgg tttaaggctt ttgaatggag atgcttctga aaagatattg     420
caatcggtaa gggatatgct gagcaacaga agtaccttca acgttcaacc agacgcagtt     480
tctataattg atggaaccca agaaggttct tatctatggg tgacagttaa ctatgcattg     540
ggaaatttag ggaaaaagta cacaaaaaca gttggagtaa tagatcttgg aggtggatca     600
gttcaaatgg cgtatgcagt attaaagaaa actgctaaaa atgctcgaaa agttgcagat     660
ggagatgatc catacatcaa gaaggttgta ctcaagggaa taccatatga tctctatgtt     720
cacagttact tacacttcgg tagagaagca tctcgagcag agatttgaa gctcactcct     780 cgttctccta acccttgcct tttagctgga tttaatggaa tctatacata ttcaggagaa     840
gagtttaagg caactgctta cacttctggt gcaaacttta taaatgcaa aaacacaatt     900 cgtaaggctc ttaagttgaa ctatccttgt ccatatcaga attgcacttt ggtggaatt     960 tggaatggtg gaggaggaaa tggacagaaa aaccttttg cttcttcatc tttcttttac    1020
ctacctgaag ataccggtat ggttgatgca agcacaccta atttcatact tcggccggtc    1080
gatattgaga ctaaagctaa agaagcttgc gcgttaaact tcgaggatgc gaaatctact    1140
tatccatttc ttgataagaa aaatgtagct tcatatgtat gcatggatct tatatatcag    1200
tatgtgttac tcgttgatgg atttggtctt gatccattgc aaaagattac atcagggaag    1260
gaaattgaat accaagatgc tattgtggaa gctgcatggc ctctaggcaa tgctgtagaa    1320
gccatatcag ctttacctaa atttgagcga ttgatgtatt ttgtttaa                1368
```